(12) United States Patent
Deming et al.

(10) Patent No.: US 11,298,424 B2
(45) Date of Patent: Apr. 12, 2022

(54) NON-IONIC AND THERMORESPONSIVE DIBLOCK COPOLYPEPTIDE HYDROGELS FOR DELIVERY OF MOLECULES AND CELLS

(71) Applicant: The Regents of the University of California, Oakland, CA (US)

(72) Inventors: Timothy J. Deming, Los Angeles, CA (US); Michael V. Sofroniew, Los Angeles, CA (US); Shanshan Zhang, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 346 days.

(21) Appl. No.: 15/516,211

(22) PCT Filed: Oct. 1, 2015

(86) PCT No.: PCT/US2015/053585
§ 371 (c)(1),
(2) Date: Mar. 31, 2017

(87) PCT Pub. No.: WO2016/054432
PCT Pub. Date: Apr. 7, 2016

(65) Prior Publication Data
US 2017/0296672 A1    Oct. 19, 2017

Related U.S. Application Data

(60) Provisional application No. 62/058,595, filed on Oct. 1, 2014.

(51) Int. Cl.
| | |
|---|---|
| *A61K 47/42* | (2017.01) |
| *A61K 9/06* | (2006.01) |
| *C12N 11/04* | (2006.01) |
| *A61K 35/30* | (2015.01) |
| *A61K 35/12* | (2015.01) |
| *C12N 11/02* | (2006.01) |
| *G01R 33/46* | (2006.01) |
| *G02B 21/00* | (2006.01) |

(52) U.S. Cl.
CPC ............... *A61K 47/42* (2013.01); *A61K 9/06* (2013.01); *A61K 35/12* (2013.01); *A61K 35/30* (2013.01); *C12N 11/02* (2013.01); *C12N 11/04* (2013.01); *G01R 33/46* (2013.01); *G02B 21/0076* (2013.01)

(58) Field of Classification Search
CPC ................................. A61L 27/52; A61K 47/42
See application file for complete search history.

(56) References Cited

U.S. PATENT DOCUMENTS

| | | |
|---|---|---|
| 5,856,308 A | 1/1999 | St. Pierre et al. |
| 6,686,446 B2 | 2/2004 | Deming et al. |
| 7,279,458 B2 | 10/2007 | Fatheree et al. |
| 8,691,204 B2 | 4/2014 | Deming et al. |
| 9,017,730 B2 | 4/2015 | Bevilacqua et al. |
| 10,448,634 B2 | 10/2019 | Bevilacqua et al. |
| 2002/0032309 A1 | 3/2002 | Deming et al. |
| 2003/0147958 A1 | 8/2003 | Ahn et al. |
| 2005/0031522 A1 | 2/2005 | Delaney et al. |
| 2005/0042753 A1 | 2/2005 | Yang et al. |
| 2005/0079159 A1 | 4/2005 | Shastri et al. |
| 2006/0240092 A1 | 10/2006 | Breitenkamp et al. |
| 2007/0190110 A1 | 8/2007 | Pameijer et al. |
| 2008/0003288 A1 | 1/2008 | Bromberg et al. |
| 2008/0125581 A1 | 5/2008 | Deming et al. |
| 2008/0166388 A1 | 7/2008 | Palecek et al. |
| 2008/0243049 A1 | 10/2008 | Hardy |
| 2009/0208548 A1 | 8/2009 | Mason et al. |
| 2010/0003336 A1 | 1/2010 | Deming et al. |
| 2010/0222407 A1 | 9/2010 | Segura et al. |
| 2012/0093722 A1* | 4/2012 | Deming ............... A61K 9/0085 424/1.69 |

(Continued)

FOREIGN PATENT DOCUMENTS

| | | |
|---|---|---|
| WO | WO-01/94379 A2 | 12/2001 |
| WO | WO-2006/113667 A1 | 10/2006 |
| WO | WO-2008/070571 A2 | 6/2008 |

(Continued)

OTHER PUBLICATIONS

IMGT: Amino Acids, http://www.imgt.org/IMGTeducation/Aide-memoire/_UK/aminoacids/charge/, 6 pgs.*

(Continued)

*Primary Examiner* — Kyle A Purdy
(74) *Attorney, Agent, or Firm* — Foley Hoag LLP; David P. Halstead; Janine S. Ladislaw

(57) ABSTRACT

The present invention is directed to copolypeptide hydrogels (DCH) containing non-ionic hydrophilic residues ($DCH_{EO}$), incorporation of thermoresponsive elements into $DCH_{EO}$, to generate thermoresponsive DCH ($DCH_T$), and hydrogels that include a combination of $DCH_{EO}$ and $DCH_T$. The invention includes preparation, uses, compositions containing the hydrogels and methods of tuning the hydrogels. The hydrogels can be used to deliver an agent or cells to an organism.

15 Claims, 24 Drawing Sheets

(56) References Cited

U.S. PATENT DOCUMENTS

2020/0288709 A1 9/2020 Bevilacqua et al.

FOREIGN PATENT DOCUMENTS

| WO | WO-2009/025802 A1 | 2/2009 |
| WO | WO-2010/096572 A2 | 8/2010 |
| WO | WO-2012/027411 A2 | 3/2012 |
| WO | WO-2014/134203 A1 | 9/2014 |

OTHER PUBLICATIONS

U.S. Appl. No. 14/182,983, Pending.
U.S. Appl. No. 14/693,601, Pending.
AU 2011 293468 Examination Report dated Dec. 10, 2013.
Bani-Jaber et al., "Efficacy of the antimicrobial peptide nisin in emulsifying oil in water," J Food Sci, 65(3):502-6 (2000).
Bermudez et al., "Molecular weight dependence of polymersome membrane structure, elasticity, and stability," Macromol, 35:8203-8 (2002).
Boyce et al., "Guideline for hand hygiene in health-care settings," Morbidity and Mortality Weekly Report, 51(RR-16):1-54 (2002).
Brogden et al., "Antimicrobial peptides: Pore formers or metabolic inhibitors in bacteria?" Nat Rev Microbiol, 3(3):238-50 (2005).
Brooks et al., "Tat peptide-mediated cellular delivery: back to basics," Adv Drug Deliv Rev, 57:559-77 (2005).
CA 2,809,093 Examination Report dated Mar. 31, 2014.
Calnan et al., "Arginine-mediated RNA recognition: the arginine fork," Science, 252:1167-71 (1991).
CN 201180051224 Examination Report datd May 8, 2014.
Deming et al., "Methodologies for preparation of synthetic block copolypeptides: Materials with future promise in drug delivery," Adv Drug Deliver Rev, 54:1145-55 (2002).
Deming et al., "Polypeptide and polypeptide hybrid copolymer synthesis via NCA polymerization," ChemInform, 38(5):1-18 (2007).
Deming et al., "Synthetic polypeptides for biomedical applications," Prog Polym Sci, 32:858-75 (2007).
Deming, "Cobalt and iron initiators for the controlled polymerization of alpha-amino acid-N-carboxyhanhydrides," Macromol, 32:4500-2 (1999).
Deming, "Facile synthesis of block copolypeptides of defined architecture," Nature, 390:386-9 (1997).
Discher et al., "A. Polymer vesicles," Science, 297:967-73 (2002).
Discher et al., "Polymer vesicles in various media," Curr Opin Coll Interface Sci, 5:125-45 (2000).
Dondoni et al., "The emergence of thiol-ene coupling as a click process for materials and bioorganic chemistry," Angew Chern Int Ed Engl., 47(47):8995-7 (2008).
Eberlein et al., "Clinical use of polihexanide on acute and chronic wounds for antisepsis and docontamination," Skin Pharmacol Physiol, 23(Suppl.):45-51 (2010).
Epand et al., "Dual mechanism of bacterial lethality for a cationic sequence-random copolymer that mimics host-defense antimicrobial peptides," J Mol Biol, 379(1):38-50 (2008).
Futaki, "Membrane-permeable arginine-rich peptides and the translocation mechanisms," Adv Drug Deliv Rev, 57:547-58 (2005).
Gabriel et al., "Infectious Disease: Connecting innate immunity to biocidal polymers," Mater Sci Eng R Rep, 57(1-6):28-64 (2007).
Gilbert et al., "Cationic antiseptics: Diversity of action under a common epithet," J Applied Microbiol, 99(4):703-15 (2005).
Ginsburg et al., "Action of polylysine on the fibrinolytic reaction," Bulletin of the Research Council of Israel, 4:51-6 (1954).
Goodson et al., "Characterization of novel antimicrobial peptoids," Antimicrob Agents Chemother, 43(6):1429-34 (1999).
Hancock et al., "Cationic peptides: A new source of antibiotics," Trends Biotechnol, 16(2):82-8 (1998).
Hanson et al., "Nanoscale double emulsions stabilized by single-component block copolypeptides," Nature, 455:85-9 (2008).
Higgins et al., "Resistance to antibiotics and biocides among non-fermenting gram-negative bacteria," Clin Microbiol Infections, 7:308-15 (2001).
Ho et al., "Improving emulsifying activity of [var epsilon]-polylysine by conjugation with dextran through the Maillard reaction," Food Chem, 68(4):449-55 (2000).
Holowka et al., "Charged polypeptide vesicles with controllable diameter," J Am Chem Soc, 127(35):12423-8 (2005).
Hou et al., "The repair of brain lesion by implamantation of hyaluronic acid hydrogels modified with laminin," J Neurosci Meth, 148(1):60-70 (2005).
Ilker et al., "Tuning the hemolytic and antibacterial activities of amphiphilic polynorbornene derivatives," J Am Chem Soc, 126(48):15870-5 (2004).
Indian Office Action dated Feb. 22, 2013 issued in Application No. 1231/mumnp/2009.
International Search Report and a Written Opinion of the International Searching Authority issued in Application No. PCT/US2010/24603, dated Sep. 28, 2010.
International Search Report and Written Opinion issued by the International Searching Authority in corresponding International Application No. PCT/US2011/048869, dated Mar. 28, 2012.
Jenkins et al., "Interactions of polylysine with platelets," Blood, 37(4):395-412 (1971).
JP 2013-526108 Examination Report dated Jun. 10, 2014.
Kar et al., "Synthesis and characterization of poly-L-lysine-grafted silica nanoparticles synthesized via NCA polymerization and click chemistry," Langmuir, 26(8):5772-81 (2010).
Kim et al., "Pharmacodynamics of insulin in polyethylene glycol-coated liposomes," Int J Pharm, 180:75-81 (1999).
Kuroda et al., "The role of hydrophobicity in the antimicrobial and hemolytic activities of polymethacrylate derivatives," Chem, 15(5):1123-33 (2009).
Lam et al., "D-amino acids govern stationary phase cell wall remodeling in bacteria," Science, 325(5947):1552-5 (2009).
Landman et al., "Polymyxins revisited," Clin Microbiol Rev, 21(3):449-65 (2008).
Lin et al., "Chondroitinase ABC has a long-lasting effect on chondroitin sulphate glycosaminoglycan content in the injured rat brain," J Neurochem, 104(2):400-8 (2008).
Lio et al., "Topical antibacterial agents," Infect Dis Clin N Am, 23(4):945-63 (2009).
Liu et al., "De novo design, synthesis, and characterization of antimicrobial beta-peptides," J Am Chem Soc, 123(31):7553-9 (2001).
Liu et al., "Nontoxic membrane-active antimicrobial arylamide oligomers," Angew Chem Int Ed Engl, 43(9):1158-62 (2004).
Mackman et al., "Role of the Extrinsic Pathway of Blood Coagulation in Hemostasis and Thrombosis," Arterisocler Thromb Vase Biol, 27: 1687-1693 (2007).
Mitchell et al., "Polyarginine enters cells more efficiently than other polycationic homopolymers," J Peptide Res, 56:318-25 (2000).
Mosmann, "Rapid colorimetric assay for cellular growth and survival: Application to proliferation and cytotoxicity assays," J Immunol Meth, 65:55-63 (1983).
Murriel et al., "Influence of protein transduction on intracellular delivery of macromolecules," Expert Opin Drug Deliv, 3(6):739-46 (2006).
Nowak et al., "Rapidly recovering hydrogels scaffolds from self-assembling diblock copolypeptide amphiphiles," Nature, 417(6887):424-8 (2002).
Oie et al., "Microbial contamination of antiseptics and disinfectants," Am J Infect Control, 24(5):389-95 (1996).
Pakstis et al., "Effect of chemistry and morphology on the biofunctionality of self-assembling diblock copolypeptide hydrogels," Biomacromol, 5:312-8 (2004).
Picout et al., "Rheology of biopolymer solutions and gels," The Scientific World Journal, 3:1 105-21 (2003).
Porter et al., "Mimicry of host-defense peptides by unnatural oligomers: Antimicrobial betapeptides," J Am Chem Soc, 124(25):7324-30 (2002).
Proctor, "Blood substitutes and experimental models of trauma," J Trauma, 54:S106 (2003).

(56) References Cited

OTHER PUBLICATIONS

Rabinovici et al., "Liposome-encapsulated hemoglobin: an oxygen-carrying fluid," Circulatory Shock, 32:1 (1990).
Riess, "Oxygen carriers ("blood substitutes")—raison d'etre, chemistry, and some physiology," Chem Rev 101(9):2797-920 (2001).
Rothbard et al., "Adaptive translocation: The role of hydrogen bonding and membrane potential in the uptake of guanidinium-rich transporters into cells," Adv Drug Deliv Rev, 57:495-504 (2005).
Rothbard et al., "Conjugation of arginine oligomers to cyclosporin A facilitates topical delivery and inhibition of inflammation," Nat Med, 6:1253-7 (2000).
Rothbard et al., "Role of membrane potential hydrogen bonding in the mechanism of translocation of guanidinium-rich peptides into cells," J Am Chem Soc, 126:9506-7 (2004).
Sakai et al., "Anion-mediated transfer of polyarginine across liquid and bilayer membranes," J Am Chem Soc, 125:14348-56 (2003).
Salick et al., "Inherent antibacterial activity of a peptide-based beta-hairpin hydrogel," J Am Chem Soc, 129(47):14793-9 (2007).
Sela et al., "Biological properties of poly amino acids," Adv Protein Chem, 14:391-478 (1959).
SG 201310360-2 Examination Report dated Jun. 24, 2014.
Song et al., "Sustained local delivery of bioactive nerve growth factor in the central nervous system via tunable diblock copolypeptide hydrogel depots," Biomater, 33:9105-16 (2012).
Stickler et al., "Antiseptic and antibiotic resistance in gram-negative bacteria causing urinary tract infection," J Clin Pathol, 33(3):288-96 (1980).
Supplementary European Search Report dated Nov. 9, 2012.
Tew et al., "Antimicrobial activity of an abiotic host defense peptide mimic," Biochim Biophys Acta, 1758(9):1387-92 (2006).
Tian et al., "Hyaluronic acid-poly-D-lysine-based three-dimensional hydrogel for traumatic brain injury," Tissue Eng, 11 (3-4):513-25 (2005).
Torchilin et al., "TAT peptide on the surface of liposomes affords their efficient intracellular delivery even at low temperature and in the presence of metabolic inhibitors," Proc Natl Acad Sci USA, 98:9786-91 (2001).
Tseng et al., "Translocation of liposomes into cancer cells by cell-penetrating peptides Peenetratin and Tat: A kinetic and efficacy study," Mol Pharmacol, 62:864-72 (2002).
Wadia et al., "Transducible TAT-HA fusogenic peptide enhances escape of TAT-fusion proteins after lipid raft macropinocytosis," Nat Med, 10:310-5 (2004).
Wadia et al., "Transmembrane delivery of protein and peptide drugs by TAT-mediated transduction in the treatment of cancer," Adv Drug Deliv Rev, 57:579-596 (2005).
Wang et al., "Antimicrobial and hemolytic activities of copolymers with cationic and hydrophobic groups: A comparison of block and random copolymers," Macromol Biosci, 11(11):1499-504 (2011).
Wyrsta et al., "A parallel synthetic approach for the analysis of membrane interactive copolypeptides," J Am Chem Soc, 123(51):12919-20 (2001).
Wyrsta et al., "Synthesis and Studies of Polypeptide Materials: Self-assembled Block Copolypepetide Amphiphiles, DNA-condensing Block Copolypeptides and Membrane-interactive Random Copolypeptides," University of California, Santa Barbara, p. 125 (2002).
Yang et al., "Biocompatibility of amphiphilic diblock copolypeptide hydrogels in the central nervous system," Biomaterials, 30(15):2881-98 (2009).
Yeaman et al., "Mechanisms of antimicrobial peptide action and resistance," Pharmacol Rev, 55(1):27-55 (2003).
Zaiou et al., "Multifunctional antimicrobial peptides: Therapeutic targets in several human diseases," J Mol Med (Berl), 85(4):317-29 (2007).
Zasloff et al., "Antimicrobial peptides of multicellular organisms," Nature, 415(6870):389-95 (2002).
Zhang et al., "Design and synthesis of nonionic copolypeptide hydrogels with reversible thermoresponsive and tunable physical properties," Biomacromol, 16:1331-40 (2015).
Zhang et al., "Supramolecular hydrogels assembled from nonionic poly (ethylene glycol)-b-polypeptide diblocks containing oegylated poly-L-glutamate," Polym Chem, 5:3346-51 [e-pub] (2014).
Zhang et al., "Thermoresponsive copolypeptide hydrogel vehicles for central nervous system cell delivery," ACS Biomater Sci Eng, 1:705-17 (2015).
Zhang et al., "Tunable diblock copolypeptide hydrogel depots for local delivery of hydrophobic molecules in healthy and injured central nervous system," Biomater, 35:1989-2000 (2014).
Zhou et al., "High potency and broad-spectrum antimicrobial peptides synthesized via ring-opening polymerization of alpha-aminoacid-N-carboxyanhydrides," Biomacromolecules, 11(1):60-7 (2010).
Boateng et al., "Wound Healing Dressings and Drug Delivery Systems: A Review," J Pharm Sci, 97(8):2892-2923 (2008).
Tjong et al., "Prediction of Protein Solubility from Calculation of Transfer Free Energy," Biophys J, 95(6): 2601-2609 (2008).
U.S. Appl. No. 12/517,009, Abandoned.
U.S. Appl. No. 13/201,974, Granted.
U.S. Appl. No. 14/182,983, Abandoned.
U.S. Appl. No. 13/776,221, Granted.
U.S. Appl. No. 14/693,601, Granted.
U.S. Appl. No. 16/658,861, Pending.
International Search Report and Written Opinion for International Application No. PCT/US2018/053050 dated Jan. 21, 2019.
Pandey et al., "Glycopolypeptide-Grafted Bioactive Polyionic Complex Vesicles (PICsomes) and Their Specific Polyvalent Interactions," ACS Omega, 1(4):600-612 (2016).
Rodriguez et al., "Enzyme-triggered cargo release from methionine sulfoxide containing copolypeptide vesicles," Biomacromolecules, 14(10):3610-3614 (2013).
Sun et al., "Conformation-Directed Formation of Self-Healing Diblock Copolypeptide Hydrogels via Polyion Complexation," Journal of the American Chemical Society, 139(42):15114-15121 (2017).
Bellomo et al., "Stimuli-responsive polypeptide vesicles by conformation-specific assembly," Nat Mater 3:244-248 (2004).

* cited by examiner

Glutamate Derivatives
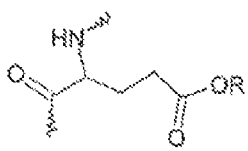
R = -(CH₂CH₂O)ₙCH₃
n = 1 - 4
Aspartate Derivatives
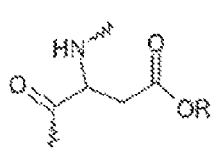
R = -(CH₂CH₂O)ₙCH₃
n = 1 - 4
Serine Derivatives
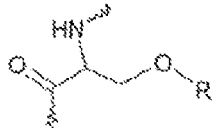
R = -(CH₂CH₂O)ₙCH₃, n = 1 - 4
-sugar
 sugar = gal, glc, man, etc.
Homocysteine Derivatives
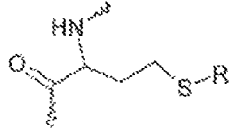
R = -(CH₂CH₂O)ₙCH₃, n = 1 - 6
Cysteine Derivatives
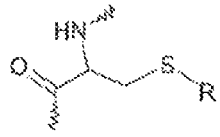
R = -(CH₂CH₂O)ₙCH₃, n = 1 - 9
-CH₂CHR'C(O)OR"
R' = -H, -CH₃
R" = -(CH₂CH₂O)ₙCH₃, n = 1 - 9
FIGURE 2

| SAMPLE NUMBER | SAMPLE NOTATION | POLYMER COMPOSITION | POLYMER STRUCTURE AT 25°C | 3% AT 25°C | 3% AT 40°C |
|---|---|---|---|---|---|
| 1 | DCHEO | (rac-EP2)₁₈₀L-30 | | Gel | Gel |
| 2 | - | (rac-EP2)₁₈₀EP2-30L-20 | | Liquid | Liquid |
| 3 | - | (rac-EP2)₁₈₀EP2-20L-30 | | Gel | Gel |
| 4 | - | (rac-EP2)₁₈₀L-30 | | Gel | Gel |
| 5 | - | (rac-EP2)₁₈₀L-20EP2-30 | | Liquid | Precipitate |
| 6 | - | (rac-EP2)₁₈₀L-30EP2-20 | | Gel | Precipitate |
| 7 | - | (rac-EP2)₁₈₀EP2-10 | | Gel | Gel |
| 8 | - | (rac-EP2)₁₈₀(EP2₀.₅L₀.₅)20 | | Liquid | Liquid |
| 9 | DCHT | (rac-EP2)₁₈₀(EP2₀.₅L₀.₅)30 | | Liquid | Gel |
| 10 | DCHT | (rac-EP2)₁₈₀(EP2₀.₅L₀.₅)40 | | Liquid | Gel |
| 11 | DCHT | (rac-EP2)₁₈₀(EP1₀.₁EP2₀.₄L₀.₅)20 | | Liquid | Gel |
| 12 | DCHT | (rac-EP2)₁₈₀(EP1₀.₂EP2₀.₃L₀.₅)30 | | Liquid | Gel |
| 13 | DCHT | (rac-EP2)₁₈₀(EP2₀.₅L₀.₅)40 | | Liquid | Gel |
| 14 | DCHT | (rac-EP2)₁₈₀(EP2₀.₅L₀.₅)50 | | Liquid | Gel |

FIGURE 3

FIFURE 10

NON-IONIC AND THERMORESPONSIVE DIBLOCK COPOLYPEPTIDE HYDROGELS FOR DELIVERY OF MOLECULES AND CELLS

CROSS-REFERENCE TO RELATED APPLICATIONS

This application is the United States National Stage application of PCT/US2015/053585, filed Oct. 1, 2015, which claims the benefit of priority to United States Provisional Patent Application Ser. No. 62/058,595, filed Oct. 1, 2014. PCT/US2015/053585 is hereby incorporated by reference in its entirety.

U.S. GOVERNMENT SUPPORT

This application was made with Government support under Grant No. R01NS084030, awarded by the National Institutes of Health. The Government has certain rights in the invention.

BACKGROUND OF THE INVENTION

Area of the Art

The field of the currently claimed embodiments of this invention relates to compositions, compositions comprising hydrogels and methods for the delivery of agents and cells into an organism or tissue via the use of compositions and compositions comprising hydrogels.

Description of the Background Art

Site-specific and locally restricted delivery of potentially therapeutic molecules is increasingly recognized as an important approach to treating certain types of disorders in the central nervous system (CNS) [1, 2]. Transplantation of neural stem cells (NSC) is also steadily gaining traction as a potential means of facilitating neural repair and replacing lost connections after CNS injury, stroke or disease [3-7]. Biomaterial carriers have the potential to significantly enhance the efficacy of both of these approaches by providing controlled, temporary and locally restricted delivery of bioactive molecules that can be targeted at either host or graft-derived cells, thereby facilitating the appropriate integration of graft with host. Hydrogels that can be injected as local depots represent a promising means of achieving sustained local delivery of different types of molecules in the CNS [8]. Hydrogels that are suitable for CNS applications need to exhibit physical properties such as rigidity, porosity and surface chemistry that are compatible with CNS tissue, as well as being able to deliver a variety of functional components [9]. Because the types of physical properties and functional components that will be required are incompletely characterized for CNS tissue in the context of injury or disease, there is a need for versatile materials that can be easily tuned to meet the requirements of specific applications and modified n accordance with practical experience.

SUMMARY OF THE INVENTION

Diblock copolypeptide hydrogels (DCH), composed of discrete ionic and hydrophobic segments, are amphiphilic synthetic materials with many features that make them attractive for CNS applications that are likely to require progressive adjustment and fine-tuning of material properties [10]. Aa combination of chemical synthesis and structural characterization was used to establish a detailed understanding of DCH structure-property relationships that allows a high level of control over gel stiffness, gel porosity, gel functionality and media stability, and many of these properties can be adjusted independently of each other [11-13]. DCH physical properties can be varied by altering copolymer chain length, architecture or composition [10] and therefore have the potential for continual refinement and incremental optimization in response to experimental or clinical experience.

DCH are physically associated gels that can be deformed by applied stress and injected through small-bore cannulae, after which they rapidly re-assemble into rigid gel networks [12]. After injection in vivo, ionic DCH self-assemble into discrete, well formed deposits of rigid gel networks that integrate well with host CNS tissue, cause no detectable toxicity or adverse inflammatory reaction, and are fully degraded after several months in vivo [9]. Both in vitro and in vivo evidence that ionic DCH can serve as depots for sustained local release of both hydrophilic and hydrophobic effector molecules for investigative and potential therapeutic applications in the CNS has been reported [14, 15]. The release time of hydrophilic molecules dissolved in DCH is dependent on DCH physical properties such as stiffness (storage modulus, G'), viscosity (G") and charge [14]. Hydrophobic molecules can be dissolved in DCH at concentrations many orders of magnitude higher than their solubility in water or buffer, and the loading capacity and release rate of hydrophobic molecules can be altered in a predictable manner by variation of DCH hydrophobic segments [15]. DCH depots injected in vivo into healthy or injured CNS can provide several weeks of sustained delivery inside the blood brain barrier of bioactive proteins, such as nerve growth factor (NGF) [14] or of hydrophobic molecules, such as tamoxifen, which is widely employed to regulate the expression of specialized transgene constructs [15]. These observations indicate that ionic DCH depots can efficiently provide sustained, local delivery within the CNS of a broad spectrum of bioactive and potentially therapeutic molecules, ranging from diverse proteins to small hydrophobic drug candidates.

The present invention is directed to extending the utility of DCH in two ways by developing DCH that support the survival of suspended cells as vehicles for cell transplantation, and by incorporating thermoresponsive elements. Compositions of polyelectrolyte ionic DCH, $K_{180}L_{20}$ and $E_{180}L_{20}$, show that highly charged DCH are prohibitively cytotoxic to cell suspensions in vitro. DCH thus needed to be redesigned to improve their cell compatibility, and efforts focused on the development of non-ionic DCH, since non-ionic polymers and hydrogels are well known to be less toxic to cells in vitro [16, 17]. The present invention is related to the design, preparation, testing and characterization of non-ionic DCH, called $DCH_{EO}$. $DCH_{EO}$ successfully support cell survival equally well in comparison with culture media in vitro and after grafting in vivo. In other embodiments, the invention relates to the design and incorporation of thermoresponsive elements into $DCH_{EO}$, to generate thermoresponsive DCH, called $DCH_T$, which undergo liquid to hydrogel transitions between room temperature and body temperature, and also retain all of the favorable features of prior ionic DCH and the cytocompatibility of non-ionic $DCH_{EO}$.

Some embodiments of the current invention include a composition comprising: an aqueous medium; and a copolypeptide hydrogel forming composition, wherein the copolypeptide composition comprises at least one hydrophilic polypeptide or copolypeptide segment and at least one hydrophobic polypeptide or copolypeptide segment, wherein the hydrophilic polypeptide or copolypeptide segment contains less than 50 mol % ionic amino acid residues. In some embodiments, this composition can further comprise a second copolypeptide hydrogel forming composition, wherein said second copolypeptide composition comprises at least one hydrophilic polypeptide or copolypeptide segment and at least one thermoresponsive polypeptide or copolypeptide segment, wherein said second copolypeptide composition undergoes a temperature induced transition between a liquid and a transparent hydrogel in said aqueous medium. Some embodiments of the current invention include a composition comprising: an aqueous medium; and a copolypeptide hydrogel forming composition, wherein said copolypeptide composition comprises at least one hydrophilic polypeptide or copolypeptide segment and at least one thermoresponsive polypeptide or copolypeptide segment, wherein said copolypeptide composition undergoes a temperature induced transition between a liquid and a transparent hydrogel in said aqueous medium.

Some embodiments of the current invention include a method of delivering an agent or a cell into an organism comprising the steps of: a) creating a mixture comprising: the agent or the cell, an aqueous medium, and a copolypeptide hydrogel forming composition, wherein said copolypeptide composition comprises at least one hydrophilic polypeptide or copolypeptide segment and at least one hydrophobic polypeptide or copolypeptide segment and wherein the hydrophilic polypeptide or copolypeptide segment contains less than 50 mol % ionic amino acid residues; and b) introducing the mixture into the organism. In some embodiments, this method can further comprise: a second copolypeptide hydrogel forming composition, wherein said second copolypeptide composition comprises at least one hydrophilic polypeptide or copolypeptide segment and at least one thermoresponsive polypeptide or copolypeptide segment, and wherein said second copolypeptide composition undergoes a temperature induced transition between a liquid and a transparent hydrogel in said aqueous medium.

Some embodiments of the current invention include a method of delivering an agent or a cell into an organism comprising the steps of: a) creating a mixture comprising: the agent or the cell, an aqueous medium, and a copolypeptide hydrogel forming composition, wherein said copolypeptide composition comprises at least one hydrophilic polypeptide or copolypeptide segment and at least one thermoresponsive polypeptide or copolypeptide segment, and wherein said copolypeptide composition undergoes a temperature induced transition between a liquid and a transparent hydrogel in said aqueous medium; and b) introducing the mixture into the organism.

DESCRIPTION OF THE FIGURES

FIG. 2 shows examples of preferred thermoresponsive residues

FIG. 3 is a schematic representations, structures, and properties of non-ionic DCH compositions. Amphiphilic, non-ionic DCH samples were designed with average total lengths of ca. 210 to 230 residues, and contained a rac-$E^{P2}$ hydrophilic domain (blue) with a disordered conformation, as well as an α-helical hydrophobic (red) or thermoresponsive (red and blue) domain. The samples with thermoresponsive domains composed of statistical sequences of thermoresponsive ($E^{P2}$ or $E^{P1}/E^{P2}$) and hydrophobic (L or A) residues were found to form $DCH_T$. rac-$E^{P2}$=poly(γ-[2-(2-methoxyethoxy)ethyl]-rac-glutamate); $E^{P1}$=poly(γ-(2-methoxyethyl)-L-glutamate); $E^{P2}$=poly(γ-[2-(2-methoxyethoxy)ethyl]-L-glutamate); L=poly(L-leucine); A=poly(L-alanine). $DCH_{EO}$=non-ionic, oligoethylene oxide based diblock copolypeptide hydrogel; $DCH_T$=non-ionic, thermoresponsive diblock copolypeptide that is liquid below ca. 30° C. and forms a hydrogel at temperatures greater than ca. 30° C.; Liquid=sample flows when inverted; Gel=sample does not flow when inverted; Precipitate=sample is insoluble in aqueous media.

DETAILED DESCRIPTION OF THE INVENTION

Figure 1:
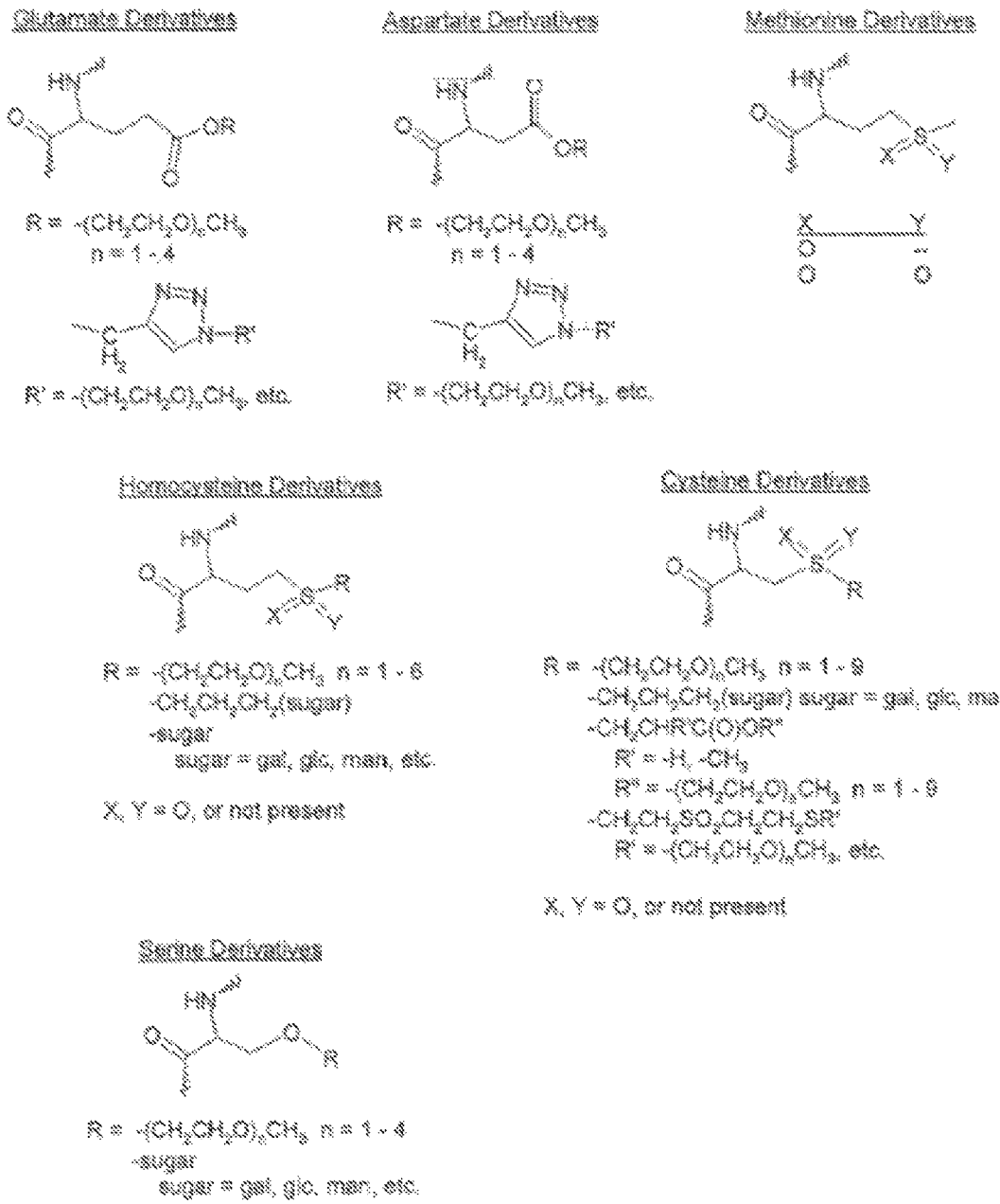
FIG. 1 shows examples of preferred non-ionic residues

The following description is provided to enable any person skilled in the art to make and use the invention and sets forth the best modes contemplated by the inventor of carrying out his invention. Various modifications, however, will remain readily apparent to those skilled in the art, since the general principles of the present invention have been defined herein specifically to provide example embodiments.

Embodiment 1: Use of Non-Ionic Copolypeptide Hydrogels for Cell Suspension, and Cell and Molecule Delivery The utility of copolypeptide hydrogels (DCH) is extended by new DCH compositions that contain less than 50 mol % ionic residues. All previously reported compositions of ionic DCH, e.g. $K_{180}L_{20}$ and $E_{180}L_{20}$, exclusively contain charged hydrophilic residues, and have also been found to be cytotoxic to cell suspensions in vitro. Although some copolypeptide compositions with non-ionic hydrophilic residues have been previously found to be unable to form hydrogels, the present invention is the result of efforts to develop new DCH, either non-ionic, or partially ionic, where the amount of charged groups in the copolypeptides was decreased substantially compared to known ionic DCH. Embodiments of the present invention are directed to new copolypeptide compositions that are able to form non-ionic DCH, called $DCH_{EO}$, as well as partially ionic DCH. These are the first non-ionic and partially ionic synthetic copolypeptide compositions that are able to form hydrogels in water, and have many potential uses. In other studies, reported separately, $DCH_{EO}$ was found to successfully support cell survival in vitro and after grafting in vivo.

A breakthrough in this example is the development of a design element that allows for non-ionic and partially ionic DCH formation, namely that a predominantly non-ionic hydrophilic segment in a DCH composition must possess a disordered chain conformation (i.e. neither predominantly α-helical nor β-sheet forming) in order to promote hydrogel formation. Current studies show that use of ordered hydrophilic segments (i.e. α-helical) in block copolypeptide assemblies, either non-ionic or <50 mol % ionic, generally results in formation of rigid sheets that form suspensions or precipitates, but will not form transparent hydrogels. One embodiment of this invention utilizes poly(γ-[2-(2-methoxyethoxy)ethyl]-rac-glutamate), (rac-$E^{P2}$), as a hydrophilic segment to successfully prepare non-ionic DCH. This segment was chosen since this polypeptide is non-ionic, highly water soluble, and, most importantly, possesses a disordered chain conformation due to its racemic residue composition.

$DCH_{EO}$ can be prepared using a variety of natural and unnatural amino acid building blocks, including chemically modified amino acids, L-amino acids, D-amino acids and mixtures of D- and L-amino acids. They can also be diblock architectures, as well as triblock or multiblock architectures. Compositional parameters of this invention are include, for example, that the copolypeptide compositions (i) contain at least one hydrophilic polypeptide or copolypeptide segment (for example, where water solubility of chains corresponding to the composition of this segment, at lengths of more than 80 residues, is greater than 0.1 mg/mL at 20° C.), (ii) where the sum of the lengths of all hydrophilic segments in a copolymer composition is greater than 80 residues, (iii) where the combined composition of all hydrophilic segments contains greater than 50 mol % non-ionic amino acid residues (i.e. amino acids with uncharged side-chains at pH=7 in water) and has a predominantly disordered chain conformation in water at 20° C. (less than 50% α-helical or β-sheet conformation content), (iv) contain at least one hydrophobic polypeptide or copolypeptide segment (for example, where water solubility of chains corresponding to the composition of this segment, at lengths of more than 10 residues, is less than 0.1 mg/mL at 20° C.), (v) where at least one hydrophobic segment has a predominantly α-helical or β-sheet chain conformation in water at 20° C. (for example, greater than 50% α-helical or β-sheet conformation content), and (vi) where the sum of the lengths of all hydrophobic segments in a copolymer composition is greater than 15 residues, and (vii) where the entire copolypeptide in aqueous medium, at a concentration of <10 wt %, forms a hydrogel.

In some embodiments of the compositions described above: (i) the sum of the lengths of all hydrophilic segments in a copolymer composition is between 120 and 600 residues, (ii) the sum of the lengths of all hydrophobic segments in a copolymer composition is between 20 and 100 residues, (iii) the copolymer contains 1 hydrophilic segment and 1 hydrophobic segment; (iv) the copolymer contains 2 hydrophilic segments and 1 hydrophobic segment; (iv) amino acid residues in a hydrophobic segment may include leucine, alanine, phenylalanine, methionine, tyrosine, tryptophan, valine, isoleucine, serine, cysteine, glutamine, asparagine, γ-alkyl glutamate esters (e.g. γ-benzyl-glutamate), β-alkyl aspartate esters (e.g. β-benzyl-aspartate), ε-modified lysines (e.g. ε-trifluoroacetyl-lysine) and their mixtures; (v) a hydrophobic segment possesses a predominantly α-helical conformation in water; (vi) non-ionic amino acid residues in a hydrophilic segment may include, but are not limited to, the examples shown in Figures and Tables (Non-ionic residues), and their mixtures; (vii) other amino acid residues in a hydrophilic segment, if present, may include, but are not limited to, lysine, glutamate, aspartate, arginine, ornithine, homoarginine, sulfonium derivatives of methionine, and their mixtures, (viii) the entire copolypeptide in aqueous medium, at a concentration of <4 wt. %, forms a hydrogel. Individual partially ionic DCH or $DCH_{EO}$ compositions can also be physically blended with other $DCH_{EO}$ or ionic DCH compositions in any proportion to yield new transparent hydrogel compositions of matter, which allows fine tuning of the resulting hydrogel properties.

Protein and peptide based hydrogels are used for many applications, ranging from personal care products, food and cosmetic thickeners to support matrices for drug delivery and tissue replacement. The non-ionic and partially ionic DCH compositions described here offer many advantages over most other hydrogels since many molecular variables can be used to adjust their physical properties. While the stiffness of most hydrogels is mainly adjusted either by polymer concentration or crosslink density, DCH stiffness can also be tuned by these parameters, or by altering amino acid composition, hydrophilic to hydrophobic ratio, molecular weight, or block architecture of the polymers. This ability to tune properties in different ways offers a facile means to adjust gel stiffness independently of concentration or crosslink density by altering the stiffness of scaffold fibrils.

The ability to control nanoscale and bulk properties by molecular design, combined with DCH injectability and abundant sites for functionalization, also makes DCH innovative candidates for use as biomaterials. DCH are unique biomaterials in that they are able to form hydrogels at low concentrations in water (<10 wt %), are fully synthetic, are composed entirely of amino acids connected by natural peptide bonds, are biodegradable, and their amphiphilic nature allows them to serve as effective carriers for delivery of both hydrophilic and hydrophobic molecules. DCH can also be injected through small-bore cannulae, after which they rapidly re-assemble into rigid gel networks allowing for minimally invasive delivery. The combination of all these properties makes ionic DCH promising synthetic biomaterial tools for experimental investigations in vitro and in vivo, and in therapeutic strategies for treatment of medical disorders or injury.

One significant limitation of ionic DCH is that they have been found to be highly toxic to cells in vitro, which prevents their use for in vitro cell culture and as vehicles for cell transplantation. Due to minimal toxicity, non-ionic $DCH_{EO}$ exhibit numerous advantageous properties over ionic DCH, or other biomaterials, for use in vitro cell culture and in vivo delivery of cells, either alone or in combination with hydrophilic and hydrophobic molecules encapsulated within the gels, for both as tools for experimental investigations and for potential therapeutic strategies. Example potential areas for their use are as depots for local delivery of therapeutics in chronic wounds, for use in prevention/treatment of STDs and HIV infections, for applications in the eyes or lungs, in the brain for treatment of glioblastoma multiforme, or for more general local delivery in tumors. Other potential uses are for cell expansion/cell culture in vitro, drug testing in 3D in vitro cell cultures, or for grafting cells in vivo, such as delivery of neural stem cells into the CNS, as reported separately.

Examples of preferred non-ionic residues are shown in FIG. 1.

Examples of hydrogel forming non-ionic and partly ionic $DCH_{EO}$ compositions are shown below in Table 1.

TABLE 1

Examples of hydrogel forming non-ionic and partly ionic $DCH_{EO}$ compositions

| Sample Number | Polymer Composition | Polymer Structure |
| --- | --- | --- |
| 1 | $(rac\text{-}E^{P3})_{180}L_{20}$ | 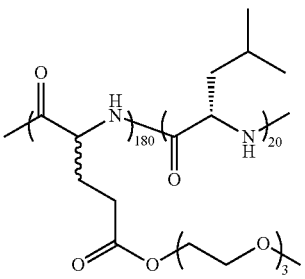 |
| 2 | $(rac\text{-}E^{P3})_{180}L_{30}$ | 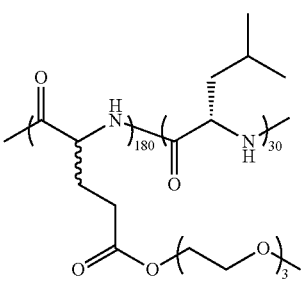 |

TABLE 1-continued
Examples of hydrogel forming non-ionic and partly ionic $DCH_{EO}$ compositions
| Sample Number | Polymer Composition | Polymer Structure |
|---|---|---|
| 3 | $(rac-E^{P2})_{180}L_{20}$ | 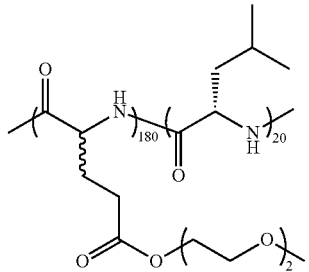 |
| 4 | $(rac-E^{P2})_{180}L_{30}$ | 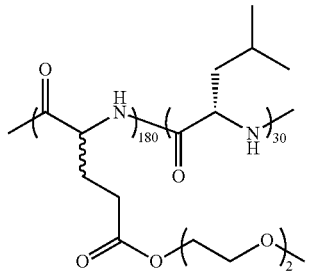 |
| 5 | $(rac-E^{P2})_{180}A_{30}$ | 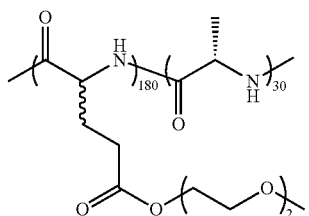 |
| 6 | $(rac-E^{P2})_{180}A_{40}$ | 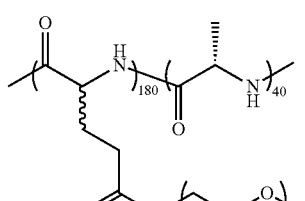 |
| 7 | $(rac-C_H^{P4})_{180}L_{20}$ | 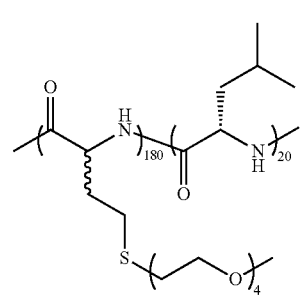 |

TABLE 1-continued

Examples of hydrogel forming non-ionic and partly ionic $DCH_{EO}$ compositions

| Sample Number | Polymer Composition | Polymer Structure |
|---|---|---|
| 8 | $(rac\text{-}C_H^{P4})_{180}L_{30}$ | |
| 9 | $(rac\text{-}C_H^{P4})_{180}L_{40}$ | |
| 10 | $(rac\text{-}C_H^{P2})_{180}L_{30}$ | |
| 11 | $(rac\text{-}C_H^{P3})_{180}L_{30}$ | |
| 12 | $(rac\text{-}C_H^{P3})_{180}L_{40}$ | |

TABLE 1-continued

Examples of hydrogel forming non-ionic and partly ionic $DCH_{EO}$ compositions

| Sample Number | Polymer Composition | Polymer Structure |
|---|---|---|
| 13 | $(rac\text{-}C_H^{P3})_{180}A_{40}$ | |
| 14 | $(rac\text{-}C_{gal}^{O2})_{180}L_{20}$ | |
| 15 | $(rac\text{-}C_{gal}^{O2})_{180}L_{30}$ | |
| 16 | $(K_{0.1}\text{-stat-}(rac\text{-}C_H^{P3})_{0.9})_{180}L_{30}$ | |

TABLE 1-continued

Examples of hydrogel forming non-ionic and partly ionic $DCH_{EO}$ compositions

| Sample Number | Polymer Composition | Polymer Structure |
|---|---|---|
| 17 | $(K_{0.3}\text{-stat-}(rac\text{-}C_H^{P3})_{0.7})_{180}L_{30}$ | |
| 18 | $(K_{0.45}\text{-stat-}(rac\text{-}C_H^{P3})_{0.55})_{180}L_{30}$ | |
| 19 | $(K_{0.1}\text{-stat-}(rac\text{-}C_H^{P3})_{0.9})_{180}A_{40}$ | |
| 20 | $(K_{0.1}\text{-stat-}(rac\text{-}C_H^{P3})_{0.9})_{180}(L_{0.5}\text{-stat-}A_{0.5})_{30}$ | |

Examples of non-hydrogel forming non-ionic and partly ionic compositions are shown below in Table 2.
TABLE 2
Examples of non-hydrogel forming non-ionic and partly ionic compositions
| Sample Number | Polymer Composition | Polymer Structure |
| --- | --- | --- |
| 1 | $K^{P2}_{100}L_{20}$ | 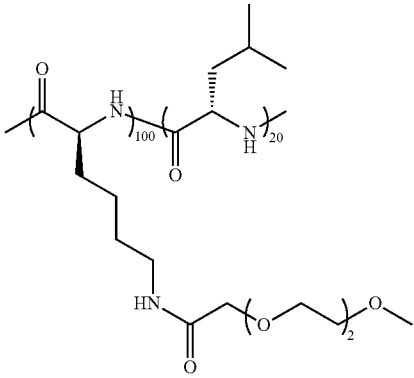 |
| 2 | $K^{P2}_{150}L_{20}$ | 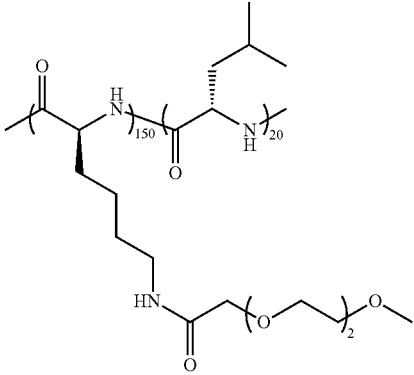 |
| 3 | $K^{P2}_{150}L_{40}$ | 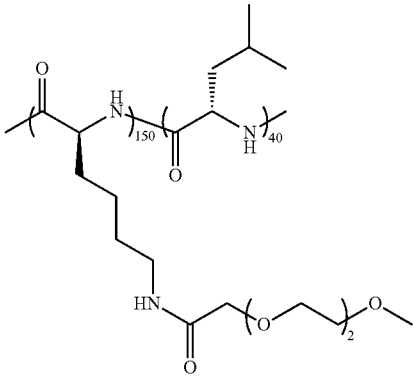 |

TABLE 2-continued
Examples of non-hydrogel forming non-ionic and partly ionic compositions
| Sample Number | Polymer Composition | Polymer Structure |
|---|---|---|
| 4 | $K^{P2}_{200}L_{20}$ | 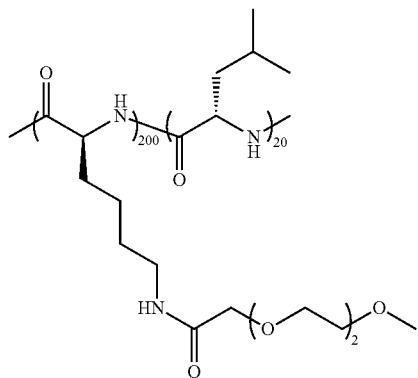 |
| 5 | $K^{P2}_{200}L_{40}$ | 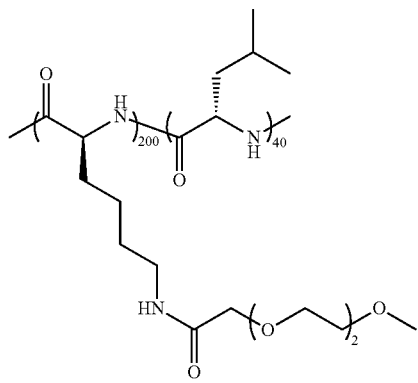 |
| 6 | $(K^{P2}_{0.5}\text{-stat-}K_{0.5})_{170}L_{30}$ | 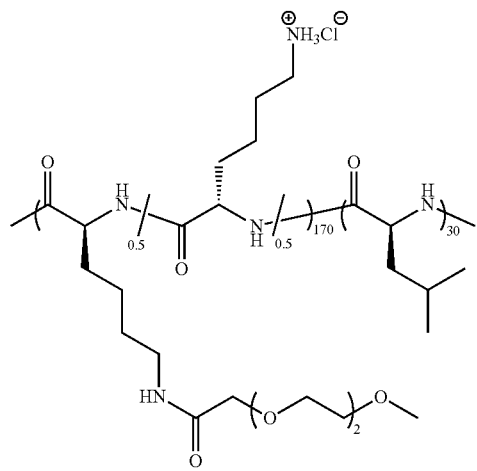 |

TABLE 2-continued
Examples of non-hydrogel forming non-ionic and partly ionic compositions
| Sample Number | Polymer Composition | Polymer Structure |
|---|---|---|
| 7 | $(K^{P2}_{0.75}\text{-stat-}K_{0.25})_{170}L_{30}$ | 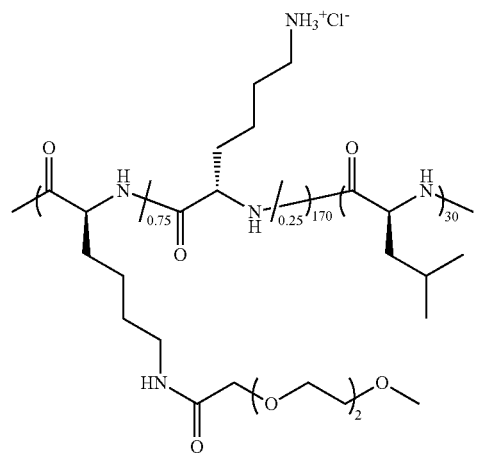 |
| 8 | $(K^{P2}_{0.5}\text{-stat-}K_{0.5})_{170}(L_{0.5}\text{-stat-}F_{0.5})_{30}$ | 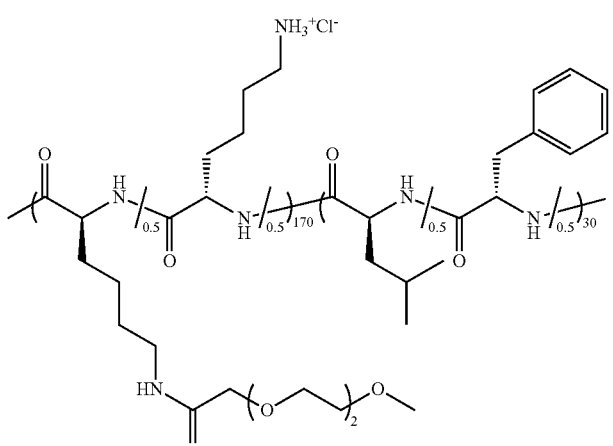 |
| 9 | $(K^{P2}_{0.75}\text{-stat-}K_{0.25})_{170}(L_{0.5}\text{-stat-}F_{0.5})_{30}$ | 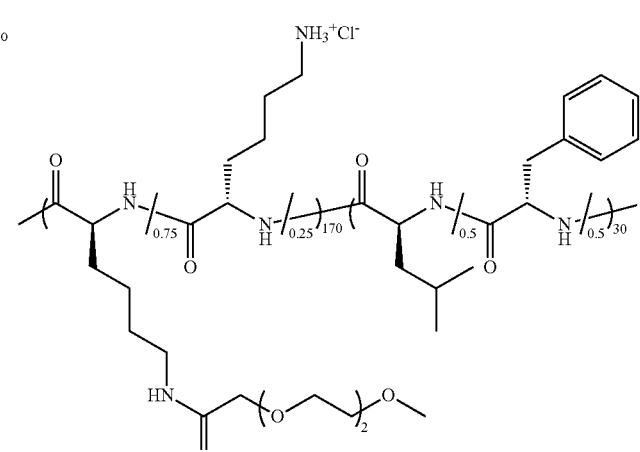 |

Embodiment 2: Compositions of Partially Ionic and Non-Ionic Copolypeptide Hydrogels and Hydrogel Blends Containing the Same The embodiment extends the utility of copolypeptide hydrogels (DCH) by providing new DCH compositions that provide a mechanism for DCH to switch between liquid and hydrogel states upon a change in temperature. All previously reported compositions of DCH are hydrogels in aqueous media that form stable hydrogels across a broad temperature range (ca. 0° C. to 100° C.); essentially all temperatures where water is in the liquid phase at 1 atm pressure. According to embodiments, the design of thermoresponsive copolypeptide segments (i.e. segments that undergo solubility transitions in response to changes in temperature) that are incorporated into copolypeptide compositions to generate thermoresponsive DCH, called $DCH_T$, which undergo full reversible, liquid to hydrogel transitions at temperatures ranging from 20° C. to 70° C. are described. These new $DCH_T$ compositions also retain all the favorable features of ionic SCH and non-ionic $SCH_{EO}$, as reported separately. The thermoresponsiveness of $DCH_T$ allows facile preparation of cell, particle, and molecule suspensions that are readily injectable or pourable as liquids at room temperature and then will self-assemble into rigid hydrogels above their transition temperature, which can be tuned to occur at body temperature after injection in vivo. $DCH_T$ viscosity at room temperature is also readily tuned to prevent cell or particle sedimentation and clumping over prolonged periods.

An innovation of this embodiment is development of a design element that allows for DCH to switch between liquid and hydrogel states upon a change in temperature, namely that a thermoresponsive segment is incorporated as pan of the copolypeptide composition, where this segment possesses a temperature induced reversible collapse-expansion transition (transition between high solubility and low solubility states) in aqueous media. When such thermoresponsive segments are incorporated into DCH-forming copolypeptide compositions in place of hydrophobic segments, $DCH_T$ are created. Prior art shows that use of purely hydrophobic segments in DCH compositions results in hydrogels that are stable as hydrogels across a wide range of temperatures (i.e. non-thermoresponsive). In addition, the combination of separate thermoresponsive segments and predominantly hydrophobic segments in DCH compositions does not yield materials that can switch between liquid and hydrogel states upon a change in temperature. This result shows that the design requirements for overall copolypeptide compositions that yield $DCH_T$ are non-obvious, and cannot be anticipated by simply combining known thermoresponsive polypeptides with known DCH compositions. As one embodiment of this invention, equimolar γ-[2-(2-methoxyethoxy)ethyl]-L-glutamate ($E^{P2}$) and L-leucine (L) residues were combined together in statistical sequences as thermoresponsive segments that were incorporated into copolymer compositions, e.g. poly(γ-[2-(2-methoxyethoxy)ethyl]-rac-glutamate)-block-poly(γ-[2-(2-methoxyethoxy)ethyl]-L-glutamate-stat-L-leucine), (rac-$E^{P2}$)$_{180}$($E^{P2}$/L)$_{30}$, to yield thermoresponsive $DCH_T$. The $E^{P2}$ component was chosen since homopolypeptides of $E^{P2}$ show temperature dependent solubility in water, where they have high solubility at ambient temperature (ca. 20° C.) and low solubility at temperatures above ca. 37° C. On the other hand, complete replacement of hydrophobic segments in DCH compositions with pure $E^{P2}$, or other thermoresponsive polypeptide, segments gave materials that did not form rigid hydrogels at elevated temperatures in water (See Examples).

The combination of $E^{P2}$ and L residues together in statistical copolypeptide sequences as single thermoresponsive segments was a newly developed design criterion for thermoresponsive $DCH_T$ formation.

$DCH_T$ can be prepared using a variety of natural and unnatural amino acid building blocks, including chemically modified amino acids, L-amino acids, D-amino acids and mixtures of D- and L-amino acids. They can also be diblock architectures, as well as triblock or multiblock architectures. The key compositional parameters of this embodiment are that the copolypeptide compositions (i) contain at least one hydrophilic polypeptide or copolypeptide segment (for example, where water solubility of chains corresponding to the composition of this segment, at lengths of more than 80 residues, is greater than 0.1 mg/mL within the temperature range of 4° C. and 90° C.), (ii) where the sum of the lengths of all hydrophilic segments in a copolymer composition is greater than 80 residues, (iii) contain at least one thermoresponsive copolypeptide segment, with length of more than 10 residues, composed of a mixture of both thermoresponsive and non-ionic (i.e. amino acids with uncharged sidechains at pH=7 in water) residues, (iv) where thermoresponsive residues are those whose corresponding homopolypeptides can undergo temperature induced transitions between high solubility and low solubility states in aqueous media, (v) where at least one thermoresponsive segment has a predominantly α-helical or β-sheet chain conformation in water above its transition temperature (for example, greater than 50% α-helical or β-sheet conformation content), (vi) where the sum of the lengths of all thermoresponsive segments in a copolymer composition is greater than 15 residues, and (vii) where the entire copolypeptide in aqueous media undergoes a temperature induced transition between liquid and transparent hydrogel states.

Some embodiments of the compositions described above are: (i) the sum of the lengths of all hydrophilic segments in a copolymer composition is between 120 and 600 residues, (ii) the sum of the lengths of all thermoresponsive segments in a copolymer composition is between 20 and 100 residues, (iii) the copolymer contains 1 hydrophilic segment and 1 thermoresponsive segment; (iv) the copolymer contains 2 hydrophilic segments and 1 thermoresponsive segment; (iv) non-ionic amino acid residues in a thermoresponsive segment may include, but are not limited to, leucine, alanine, phenylalanine, methionine, tyrosine, tryptophan, valine, isoleucine, serine, cysteine, glutamine, asparagine, γ-alkyl glutamate esters (e.g. γ-benzyl-glutamate), β-alkyl aspartate esters (e.g. β-benzyl-aspartate), ε-modified lysines (e.g. ε-trifluoroacetyl-lysine) and their mixtures; (v) a thermoresponsive segment possesses a predominantly α-helical conformation in water above its transition temperature; (vi) thermoresponsive amino acid residues in a thermoresponsive segment may include, but are not limited to, the examples shown in the Figures and Tables (Thermoresponsive residues), and their mixtures; (vii) amino acid residues in a hydrophilic segment may include, but are not limited to, lysine, glutamate, aspartate, arginine, ornithine, homoarginine, sulfonium derivatives of methionine, the examples shown in the attached page of structures (Non-ionic residues), and their mixtures; (viii) the temperature at which the copolypeptide in aqueous medium, at a concentration of <10 wt %, transitions between liquid and hydrogel states is between 30° C. and 45° C. Individual $DCH_T$ compositions can also be physically blended with other $DCH_T$, $DCH_{EO}$ or ionic DCH compositions in any proportion to yield new transparent hydrogel compositions of matter, which allows fine tuning of the resulting hydrogel properties. More specific preferred embodiments and other non-limiting examples of DCH$_T$ are attached to this record (Examples).

One significant limitation of other DCH is that they are rigid hydrogels at all temperatures in water, which limits their ability to be injected through small needles, or makes dispersion of cells or particles within the hydrogels difficult. Due to their thermal transition between liquid and hydrogel states and tunable and mild temperatures, DCH$_T$ exhibit numerous advantageous properties over other DCH, or other biomaterials, for suspension of cells or particles and their subsequent injection, either alone or in combination. with hydrophilic and hydrophobic molecules encapsulated within the gels. Example potential areas for their use are as injectable depots for local delivery of therapeutics in chronic wounds, for use in prevention/treatment of STDs and HIV infections, for applications in the eyes or lungs, in the brain for treatment of glioblastoma multiforme, or for more general local delivery in tumors. Other potential uses are for cell expansion/cell culture in vitro, drug testing in 3D in vitro cell cultures, or for grafting cells in vivo, such as delivery of neural stem cells into the CNS, as reported separately.

Examples of preferred thermoresponsive residues are shown in FIG. 2.

Examples of hydrogel forming thermoresponsive DCH$_T$ compositions are shown below in Table 3.

TABLE 3

Examples of hydrogel forming thermoreponsive DCH$_T$ compositions

| Sample Number | Polymer Composition | Polymer Structure | $T_G$ (° C.) |
|---|---|---|---|
| 1 | (rac-E$^{P2}$)$_{180}$(E$^{P2}$$_{0.5}$-stat-L$_{0.5}$)$_{30}$ | [chemical structure] | 37 |
| 2 | (rac-E$^{P2}$)$_{180}$(E$^{P2}$$_{0.5}$-stat-L$_{0.5}$)$_{40}$ | [chemical structure] | ND |
| 3 | (rac-E$^{P2}$)$_{180}$(E$^{P1}$$_{0.1}$-stat-E$^{P2}$$_{0.4}$-stat-L$_{0.5}$)$_{30}$ | [chemical structure] | 34 |
| 4 | (rac-E$^{P2}$)$_{180}$(E$^{P1}$$_{0.2}$-stat-E$^{P2}$$_{0.3}$-stat-L$_{0.5}$)$_{30}$ | [chemical structure] | 30.6 |

TABLE 3-continued
Examples of hydrogel forming thermoreponsive DCH$_T$ compositions
| Sample Number | Polymer Composition | Polymer Structure | $T_G$ (° C.) |
|---|---|---|---|
| 5 | (rac-E$^{P2}$)$_{180}$(E$^{P2}$$_{0.5}$-stat-A$_{0.5}$)$_{40}$ | 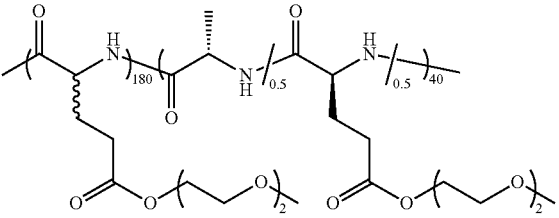 | 37.5 |
| 6 | (rac-E$^{P2}$)$_{180}$(E$^{P2}$$_{0.5}$-stat-A$_{0.5}$)$_{50}$ | 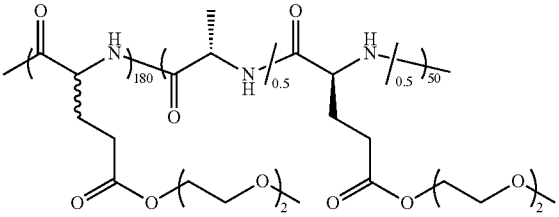 | ND |
| 7 | (rac-C$_H$$^{P4}$)$_{180}$(C$_H$$^{P4}$$_{0.5}$-stat-L$_{0.5}$)$_{30}$ | 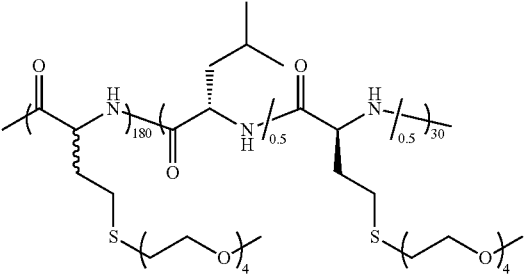 | 41 |
| 8 | (rac-C$_H$$^{P4}$)$_{180}$(C$_H$$^{P4}$$_{0.5}$-stat-L$_{0.5}$)$_{40}$ | 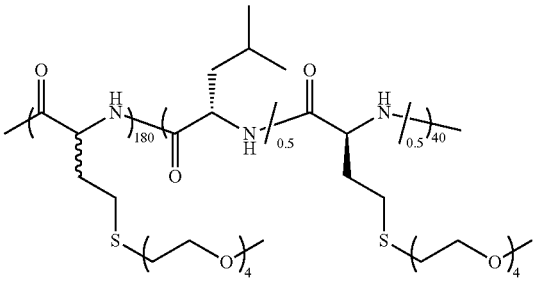 | ND |

TABLE 3-continued

Examples of hydrogel forming thermoresponsive $DCH_T$ compositions

| Sample Number | Polymer Composition | Polymer Structure | $T_G$ (° C.) |
|---|---|---|---|
| 9 | $(rac\text{-}C_H^{P4})_{180}(C_H^{P2}{}_{0.25}\text{-}stat\text{-}C_H^{P4}{}_{0.25}\text{-}stat\text{-}L_{0.5})_{30}$ | | 33 |
| 10 | $(rac\text{-}C_H^{P4})_{180}(C_H^{P2}{}_{0.25}\text{-}stat\text{-}C_H^{P4}{}_{0.25}\text{-}stat\text{-}L_{0.5})_{40}$ | | ND |
| 11 | $(rac\text{-}C_H^{P4})_{180}(C_H^{P3}{}_{0.5}\text{-}stat\text{-}L_{0.5})_{30}$ | | 35 |
| 12 | $K_{180}(C_H^{P3}{}_{0.5}\text{-}stat\text{-}L_{0.5})_{20}$ | | 33 |

TG = liquid to hydrogel transition temperature in DI water;
ND = Not Determined

TABLE 4

Examples of non-thermoresponsive compositions.

| Sample # | Polymer Composition | Polymer Structure | 25° C. | 40° C. |
|---|---|---|---|---|
| 1 | (rac-$E^{P2}$)$_{180}$$E^{P2}$$_{30}$L$_{20}$ | | L | L |
| 2 | (rac-$E^{P2}$)$_{180}$$E^{P2}$$_{20}$L$_{30}$ | | G | G |
| 3 | (rac-$E^{P2}$)$_{180}$$E^{P2}$$_{10}$L$_{30}$ | | G | G |
| 4 | (rac-$E^{P2}$)$_{180}$L$_{20}$$E^{P2}$$_{30}$ | | L | P |
| 5 | (rac-$E^{P2}$)$_{180}$L$_{30}$$E^{P2}$$_{20}$ | | G | P |

TABLE 4-continued

Examples of non-thermoresponsive compositions.

| Sample # | Polymer Composition | Polymer Structure | 25° C. | 40° C. |
|---|---|---|---|---|
| 6 | $(rac\text{-}E^{P2})_{180}L_{30}E^{P2}_{10}$ | | G | G |
| 7 | $(rac\text{-}E^{P2})_{180}(E^{P2}_{0.5}\text{-stat-}L_{0.5})_{20}$ | | L | L |
| 8 | $(rac\text{-}C_H^{P3})_{180}(C_H^{P2})_{30}$ | | L | L |
| 9 | $(rac\text{-}C_H^{P3})_{180}(C_H^{P2})_{40}$ | | L | L |
| 10 | $(rac\text{-}C_H^{P3})_{180}(C_H^{P2}_{0.5}\text{-stat-}C_H^{P3}_{0.5})_{30}$ | | L | L |

The descriptions under columns 25° C. and 40° C. above represent the characteristic of 3 wt % sample at given temperature in DI water.
L = liquid,
G = gel,
P = precipitate.

Embodiment 3: Non-Ionic and Thermoresponsive Diblock Copolypeptide Hydrogels for Delivery of Agents and Cells in Healthy and Injured Central Nervous System Non-ionic DCH, called $DCH_{EO}$, and thermoresponsive DCH, called $DCH_T$, are useful tools for delivery of agents and transplantation of cells into the CNS via injection in vivo. As used herein, agents can include any molecule that is desirable for introduction into an organism. Agents can include, but are not limited to, for example, a pharmaceutical substance, nucleic acid, peptide, hormone, or imaging agent. Agents include molecules used for diagnostic, therapeutic, preventative, supplementary or other desirable purposes. Non-ionic $DCH_{EO}$ supported the survival of fully immersed and suspended cells in vitro in a manner equivalent to cell culture media. Thermoresponsive elements were incorporated into $DCH_{EO}$ to yield $DCH_T$, which were engineered to undergo liquid to hydrogel transitions at a predetermined temperature between ambient room temperature at 22° C. and body temperature at 37° C. In vitro and in vivo experiments showed that $DCH_T$ retained the many advantageous features of ionic DCH, such as injectability, tunable stiffness and viscosity, as well as the ability to load and provide sustained release of both hydrophilic and hydrophobic molecules [9, 10, 14, 15]. In addition, non-ionic $DCH_T$ exhibits cytocompatibility of $DCH_{EO}$ and supports the survival of NSC injected through small-bore cannulae and transplanted into the CNS better than culture media. Non-ionic $DCH_T$ exhibit numerous advantageous properties for in vivo delivery of cells and molecules in the CNS for experimental investigations and potential therapeutic strategies.

Preparation and Tunability of Non-Ionic $DCH_T$

DCH are highly versatile hydrogels whose amino acid compositions can be altered in various ways to add features while retaining basic gel properties. Further modified compositions of DCH incorporate unprecedented properties into these materials. Specifically, cationic or anionic residues in DCH are replaced with non-ionic amino acids to make them compatible with cells, and also replaced the hydrophobic domains of DCH with thermoresponsive segments to yield materials that can undergo liquid to hydrogel transitions upon increasing temperature. Many nonionic, hydrophilic polypeptides composed of enantiomerically pure amino acids tend to adopt ordered chain conformations, e.g. α-helices [44-46], accordingly, the present invention uses non-ionic, hydrophilic polypeptides composed of racemic amino acids for the hydrophilic segments of $DCH_{EO}$. Previous work has shown that amphiphilic block copolypeptides with hydrophilic/hydrophobic compositions comparable to DCH, but containing α-helical, non-ionic hydrophilic segments, formed only sheet-like assemblies that did not form hydrogels [35]. Hence, a design element for successful formation of $DCH_{EO}$ was the use of a racemic, non-ionic hydrophilic segment, i.e. rac-$E^{P2}$, that possesses a disordered chain conformation in water, which allows the block copolypeptides to assemble into structures to yield the desired hydrogels [10].

The present invention incorporates thermoresponsive properties in to $DCH_{EO}$, creating non-ionic $DCH_T$, by replacing the conventional hydrophobic segments of DCH with a copolypeptide segment that possesses temperature sensitive water solubility (i.e. a lower critical solution temperature) [36]. Unlike rac-$E^{P2}$, enantiomerically pure $E^{P2}$ possesses thermoresponsive water solubility, similar to other polymers that contain short ethylene glycol side-chain substituents [21]. $E^{P2}$ copolymers have been reported to form thermoresponsive assemblies, but have not been previously used to form hydrogels [47]. A potential drawback of $E^{P2}$ segments are that they can form β-sheet structures at elevated temperatures that leads to irreversibility in their thermoresponsive behavior and polymer precipitation [21]. Hence, direct addition or incorporation of $E^{P2}$ segments into DCH compositions was not able to yield DCH with the desired thermoresponsive properties. One innovation is the use of statistical copolymerization of $E^{P2}$ residues with helicogenic hydrophobic residues, e.g. leucine or alanine, to prepare thermoresponsive segments that allowed the preparation of $DCH_T$. These materials possessed highly reversible thermal transitions and formed no precipitates at elevated temperatures. While other polypeptide containing thermoresponsive hydrogels have been prepared [48-50], none are block copolypeptides and none contain a comparable statistical copolypeptide thermoresponsive element. The unique design features of $DCH_T$ allow preparation of thermoresponsive hydrogels with sharp, tunable transition temperatures ($T_G$), thermal reversibility, high transparency, and all the other features of DCH.

Similar to ionic DCH, non-ionic $DCH_T$ gel stiffness (G') above $T_G$ was easily tuned by adjustment of copolypeptide concentration in aqueous media, or by varying the length of the assembling, thermoresponsive domain. The liquid to gel transition temperatures of $DCH_T$, $T_G$, could also be readily tuned either by incorporation of $E^{P1}$ residues within the thermoresponsive domain, or by physically blending aqueous samples of $DCH_T$ with $DCH_{EO}$. The use of the shorter ethylene glycol side-chain substituents in $E^{P1}$ residues to lower $T_G$ is effective since $E^{P1}$ residues are more hydrophobic compared to $E^{P2}$ residues, which lowers $DCH_T$ solubility in water as temperature is increased. Blends of $DCH_T$ with $DCH_{EO}$ were also found to possess lower $T_G$ compared to pure $DCH_T$, which is due to the addition of $DCH_{EO}$ that possesses greater hydrophobic content compared to $DCH_T$. One important requirement when blending different DCH is that the hydrophobic and/or thermoresponsive domains should be similar in length, otherwise, destabilization of the hydrogel structure can occur [13]. Even so, the physical blending of samples to fine tune $T_G$ does have a practical advantage since $T_G$ can be changed by simply varying the mixing ratio of previously prepared samples, as opposed to having to prepare new samples with different $E^{P1}$ to $E^{P2}$ ratios.

Efficient Molecular Delivery Via $DCH_T$

The ability to control and adjust rates of cargo release from biomaterial delivery vehicles is desirable. Sustained release of a bioactive protein growth factor from depots of ionic DCH for up to several weeks in vivo in the CNS has been previously reported [14]. Since significant modifications were made to the design of DCH in the present invention to create $DCH_T$, the release rates of both hydrophilic and hydrophobic cargos from non-ionic $DCH_T$ in vitro were studied, and compared to those for ionic DCH. Hydrophilic proteins were readily encapsulated within optimized $DCH_T$ formulations, and were released at rates comparable to those for ionic DCH. One notable difference was that in contrast with ionic DCH, rates of protein release from $DCH_T$ were insensitive to protein charge due to their non-ionic nature. This characteristic is beneficial since protein release rates from $DCH_T$ were found to be affected primarily by protein size as opposed to specific sequence, and could be tuned simply by varying $DCH_T$ concentration. For hydrophobic cargos, $DCH_T$ were found to be similar to ionic DCH [15] by effectively solubilizing small hydrophobic molecules, which is notable since this occurs even in the liquid state of $DCH_T$ at 20° C. where these copolypeptides are less hydrophobic. Under these conditions, it is likely that the permanently hydrophobic residues (i.e. leucine or alanine) within the thermoresponsive segments of the $DCH_T$ impart the copolypeptides with surfactant properties that can solubilize the molecules. Most hydrogels are unable to dissolve hydrophobic compounds, and typically can only suspend such compounds as insoluble precipitates [51]. The ability of DCH and $DCH_T$ to dissolve relatively large quantities of hydrophobic compounds is remarkable and makes them highly useful for local delivery of these molecules.

Non-Ionic $DCH_T$ are Efficient Vehicles for CNS Cell Transplantation

Transplantation of NSC and other cells is under intense investigation for potential therapeutic applications in numerous CNS disorders [3-7]. CNS cell transplantation would benefit from vehicles that enhance cell viability during the injection procedure, optimize cell distribution and deliver different types of molecules to regulate the maturation of transplanted cells and their integration with host cells. Various vehicles and carriers are being tested, including natural and synthetic materials. For example, fibrin matrix is a natural material formed by mixing fibrinogen and thrombin, which rapidly interact and entrap cells and added molecules in clot like structures that are reported useful in retaining grafted cells at injection sites [5]. Nevertheless, the rapid clotting of fibrin can complicate delivery procedures, and both thrombin and fibrin are endogenous blood borne molecules with powerful signaling properties that affect multiple cell types at sites of CNS injury [1]. Prolonged exposure to high levels of these or other natural materials used as transplant vehicles may result in effects that are unexpected or may not be desirable and could distort the function of graft or host cells. In this regard, fully synthetic biomaterials that are in themselves functionally inert but can be intentionally functionalized with well-characterized molecules for specific contexts offer advantages as vehicles and carriers for CNS cell transplantation. The ability to generate vehicles whose components are fully known and characterized is an important for clinical translational considerations. Non-ionic $DCH_T$ exhibit numerous properties that make them well suited to serve as vehicles for CNS NSC transplantation.

Cyto-Compatibility of Non-Ionic $DCH_T$

Non-ionic DCH of the invention overcome the drawback that highly charged ionic polypeptides can exhibit cytotoxicity to fully immersed or encapsulated cells [30, 31], and ionic DCH, $K_{180}L_{20}$ and $E_{180}L_{20}$, showed cytotoxicity towards cell suspensions in vitro. A likely explanation for the observations that ionic DCH exhibit no detectable toxicity in vivo [9] but are cytotoxic in vitro, is that DCH form discrete deposits in vivo that interface with host cells only along borders, whereas in cell suspensions in vitro, cells are fully immersed in and encapsulated by DCH. Under these full immersion conditions, the high charge density of the ionic DCH is likely to account for the cell toxicity [32]. Replacement of cationic hydrophilic segments with non-ionic hydrophilic segments results in materials with minimal in vitro cytotoxicity [18, 33, 34]. According to the present invention it was found that non-ionic $DCH_T$ supported the survival of fully immersed and suspended cells in vitro in a manner equivalent to cell culture media over prolonged periods of time, up to a week or longer in suspension cell cultures.

Improved Survival and In Vivo Distribution of NSC Injected in $DCH_T$

Local transplantation of exogenous cells into specific CNS sites is likely to require injection through small-bore cannulae that limit damage to host CNS tissue, Injection of cell suspensions in this manner can be hampered by simple physical factors such as cell sedimentation and clumping before or during the injection process, which in turn can restrict access to nutrients, decrease cell health and increase cell damage and death due to shear forces during injection [39, 40, 52]. All of these factors can contribute not only to poor yields of viable cells after injection, but can also lead to uneven and clumped together distribution of transplanted cells within the target host tissue. Non-ionic $DCH_T$ offer several advantages for increased efficiency of NSC transplantation ii the CNS. The thermo-responsive characteristics and facile tuning of $DCH_T$ physical properties allow for easy preparation of cell and molecule suspensions that are liquid and easily injected at room temperature (22° C.) and that self-assemble into well-formed hydrogels at body temperature (37° C.). In addition, the viscosity of $DCH_T$ at room temperature is easily tuned to prevent cell sedimentation over prolonged periods and can also protect cells and increase the survival of NSC during loading and passage through small-bore cannulae used for CNS injections. Whereas NSC sedimented rapidly in culture media, they remained suspended and viable for prolonged times in non-ionic $DCH_T$. NSC could be stored as cell suspensions in $DCH_T$ for long times, facilitating protracted delivery procedures. NSC suspended in $DCH_T$ exhibited significantly and substantially greater viability during injection through small-bore cannulae. Cells injected in $DCH_T$ also exhibited more even distribution of transplanted cells within the host tissue with a density that more closely approximated that of host tissue, whereas NSC injected in culture media only formed dense clumps of transplanted cells. NSC grafts transplanted at a delayed time after CNS injury dispersed well in lesion sites, and the grafted cells interfaced well and intermingled with host cells at lesion borders to form host-graft transition zones, thereby generating bridges of neural cells across non-neural lesion core tissue in a manner that might connect different regions of host neural tissue.

Potential for Simultaneous Manipulation In Vivo of Both Host and Grafted Cells Using $DCH_T$ One current limitation in transplantation of NSC into CNS is the lack of ability to regulate NSC maturation and integration with host cells. During neural development in vivo, NSC mature and organize into functional units over prolonged times in a manner that is regulated and guided by exposure to different molecules at different times. These molecular cues are lacking in the mature injured or diseased CNS that is the main target of NSC transplantation. As discussed above, $DCH_T$ exhibit good capacity for molecular delivery of both hydrophilic and hydrophobic molecules. Thus, $DCH_T$ have the potential to provide sustained and temporally regulated exposure of grafted cells to both hydrophilic growth factors [14] and hydrophobic manipulators of gene expression or epigenetic mechanisms [15] after transplantation in vivo and during the time when grafted cells are interacting with and integrating with host cells. In this manner, $DCH_T$ may help to regulate NSC maturation and facilitate appropriate integration of NSC with host cells.

In addition, $DCH_T$ offer the possibility of delivering molecules that may influence host cells to alter their interactions with grafted cells and to promote repair and recovery. For example, a number of different growth factors are now recognized as being able to stimulate and attract the growth of specific types of axons [4, 53, 54], and molecular regulators of intrinsic neuronal capacity for axon growth are being identified [55, 56]. Providing or modulating such factors via $DCH_T$ could improve regrowth of axons into, through and out of grafts of transplanted NSC. In this regard it is important to note that $DCH_T$ caused little detectable long-term effects after injection into healthy CNS tissue, indicating that $DCH_T$ depots (without cell grafts) could be injected into healthy CNS in an effort either to stimulate regeneration promoting genetic programs, or to attract regenerating axons into regions that have target neurons with which they might form new connections. It is noteworthy that $DCH_T$ have the potential to simultaneously deliver multiple molecules, including hydrophilic proteins and hydrophobic small molecules, which can be targeted at widely different cellular mechanisms. For example, $DCH_T$ can also simultaneously deliver molecules to stimulate effects together with function-blocking molecules that allow precise dissection of molecular mechanisms in vivo in a manner previously done primarily in vitro (Anderson et al, unpublished observations). Thus, DCH provide a powerful new tool for experimental investigation of cellular and molecular mechanisms during the study of CNS injury and repair in vivo.

Potential for $DCH_T$ to Facilitate Regrowth of Host Axons Along Grafted Cells Across CNS Lesions CNS lesions that form after severe tissue damage are characterized by non-neural lesion core tissue (also referred to as fibrotic scar) and fluid filled cysts that are all surrounded by compact borders of astroglial scar [1, 57]. Human SCI in particular is characterized by large areas of non-neural fibrotic scar tissue and cysts that can extend over long distances [58]. This non-neural scar tissue is exquisitely hostile to regrowth of damaged host axons. Facilitating host axon regrowth to re-establish connectivity across such lesions is a complex challenge. Although astrocyte scars are commonly regarded as inhibitory to axon regrowth after CNS injury [59], axons stimulated to grow by genetic manipulations appear to grow along astrocyte bridges when these are present in CNS lesions, but even these stimulated axons do not grow among non-neural lesion core cells [56]. Re-establishing neuronal connections across such CNS lesions is a long sought after research goal. There is growing evidence that formation of new relay circuits has the potential to re-establish certain forms of function after CNS injury, and that achieving even short distance axon regrowth can lead to formation of relay circuits [60, 61]. Grafts of NSC that generate either neurons or neural glial cells are being explored as potential means of facilitating the formation of new relay connections. There is evidence that NSC transplanted into lesions can generate new neurons that form new functional relays [3-5]. In addition, grafted NSC that generate neural glial cells have the potential to form bridges that can enable host axons to re-grow across tissue lesions and thereby form new relays [62, 63]. NSC in $DCH_T$ injected into lesion sites after SCI distribute well and give rise to astroglia throughout the non-neural lesion core as well as astroglia that intermingle with host neural cells at lesion edges, thereby forming potential bridges of neural cells across lesions. Grafted, NSC-derived astroglia in $DCH_T$ were found to support the transition of host axons from host astroglia to graft astroglia and support the growth of axons among grafted astroglia in otherwise hostile non-neural lesion core throughout the transplant. These findings add to other evidence that grafts of neural lineage cells, including astroglia can support the growth of axons in lesions that would otherwise present an environment hostile to such growth [62, 63]. Combining the ability of $DCH_T$ to simultaneously deliver cells and molecules Is a new approach to test for promoting axon regrowth across CNS lesions.

The utility of DCH for CNS applications is extended by developing non-ionic $DCH_{EO}$, and thermoresponsive $DCH_T$. Extensive in vivo and in vitro tests showed that non-ionic $DCH_T$ exhibit excellent cytocompatibility and support the long term viability of suspended cells in vitro while retaining the many advantageous features d previously studied ionic DCH, such as injectability, tunable rigidity and porosity, and the ability to load and provide sustained release of both hydrophilic and hydrophobic molecules. The thermoresponsiveness of $DCH_T$ allowed facile preparation of cell and molecule suspensions that are easily injected liquids at room temperature and that self-assembled into well-formed hydrogels at body temperature. The viscosity of $DCH_T$ at room temperature was easily tuned to prevent cell sedimentation over prolonged periods and increased the survival of NSC injection through small-bore cannulae used for CNS injections. $DCH_T$ can deliver both hydrophilic proteins and hydrophobic small molecules targeted at widely different cellular mechanisms, including function-blocking molecules that allow dissection of molecular mechanisms in vivo. Non-ionic $DCH_T$ will provide a powerful new tool for in vivo delivery of cells and molecules in the CNS for experimental investigations and potential therapeutic strategies.

Methods

In Vitro Cell Viability Assay

The viability of cells maintained under different conditions in vitro was quantified using the Cell Titer 96 Aqueous Nonradioactive Cell Proliferation Assay (MTS assay) (Promega, Madison Wis.) [18]. For cells cultured in 96 well plates, the culture plates were centrifuged briefly and the cell culture medium was aspirated. For cells cultured in dialysis cassettes, 100 μl of cell suspension was transferred into 96-well cell culture plate and centrifuged briefly to allow aspiration of the cell culture medium. Fresh medium containing 20% MTS solution was then added to the cells, which were then transferred to a humidified 5% $CO_2$ incubator at 37° C. for 1 hour. Absorbance at 490 nm (A490) was measured for each well using an Infinite F200 plate reader (Tecan Systems Inc., San Jose, Calif., USA). The background absorbance was read at 700 nm (A700) and subtracted from A490. The relative survival of the cells was quantified by taking the ratio of the (A490-A700) values and comparing between the experimental and control cells.

Cell Preparations

Cells for In Vitro Evaluations of DCH Cytotoxicity

The cytotoxicity of the different DCH was evaluated using HeLa cells and murine bone-marrow mesenchymal stem cells (MSCs). The HeLa cell line was maintained using standard tissue culture protocols [18]. MSCs were isolated from 6- to 8-week-old wild type mice [19]. Briefly, marrow cells, flushed out of tibias and femurs, were plated in 75 $cm^2$ tissue culture flasks at the concentration of 0.3 to $0.4 \times 10^6$ cells/$cm^2$ using Murine Mesencult as medium (Stem Cell Technologies, Vancouver, British Columbia, Canada). Cells were cultured in plastic plates as adherent cells and kept in a humidified 5% $CO_2$ incubator at 37° C., refreshing medium every 3 days until cells reached 80% confluence. For cytotoxicity evaluations, HeLa cells or MSCs were mixed into 2%, 3% or 4% DCH, (either $K_{180}L_{20}$ or $E_{180}L_{20}$ prepared as described previously [9]), or in serum-free medium containing DMEM/F12 (Invitrogen) and seeded onto wells of a 96-well tissue culture plates at a density of $8 \times 10^4$ cells/$cm^2$. Cells were cultured in a 37° C. humidified atmosphere with 5% $CO_2$, and at desired time points, cell viability was measured using the MTS assay.

Neural Stem Cells (NSC) for In Vitro Evaluations and In Vivo Transplantation.

Primary neural stem cells (NSCs) were prepared from forebrains of embryonic day 11 (E11) CD1 mice [20]. Telencephalon dissected from E11 embryos was first coarsely dissociated by mechanical force then treated with Papain (Worthington) for 5 minutes at 37° C. with constant shaking. 3×10⁶ dissociated cells were then plated onto a poly-ornithine (PO, Sigma) and fibronectin (FN, Sigma) coated 10 cm dishes in serum-free medium containing DMEM/F12 (Invitrogen), 1% B27 (Invitrogen), and penicillin-streptomycin (50 μg/ml and 50 U/ml, respectively). Cells were fed daily with basic fibroblast growth factor (bFGF, PeproTech) at a final concentration of 10 ng/ml. After reaching confluence, NSCs were passaged with enzymatic dissociation using StemPro Accutase (invitrogen) and re-plated on PO/FN coated tissue culture treated plastic at a density of 1-2×10⁶ cells per 10 cm dish and propagated until use in in vitro or in vivo experiments.

Preparation of $DCH_T$ and $DCH_E$

Materials and Instrumentation

Tetrahydrofuran (THF), hexanes, and methylene chloride were dried by purging with nitrogen and passage through activated alumina columns prior to use. $Co(PMe_3)_4$ and amino acid N-carboxyanhydride (NCA) monomers were prepared according to literature procedures [12, 21]. All other chemicals were purchased from commercial suppliers and used without further purification unless otherwise noted. Thin-layer chromatography (TLC) was conducted with EMD gel 60 F254 precoated plates (0.25 mm) and visualized using a combination of UV, anisaldehyde, and phosphomolybdic acid staining. Selecto silica gel 60 (particle size 0.032-0.063 mm) was used for flash column chromatography. Fourier Transform Infrared (FTIR) measurements were taken on a Perkin Elmer RX1 FTIR spectrophotometer calibrated using polystyrene film. $^1H$ NMR spectra were acquired on a Bruker ARX 400 spectrometer. Tandem gel permeation chromatography/light scattering (GPC/LS) was performed at 60° C. using an SSI Accuflow Series III pump equipped with Wyatt DAWN EOS light scattering and Optilab rEX refractive index detectors. Separations were achieved using $10^5$, $10^4$, and $10^3$ Å Phenomenex Phenogel 5 μm columns at 60° C. with 0.1 M LiBr in DMF as eluent and sample concentrations of 5 mg/mL. Pyrogen free deionized water (DI) was obtained from a Millipore Milli-Q Biocel A10 purification unit.

Figure 16:
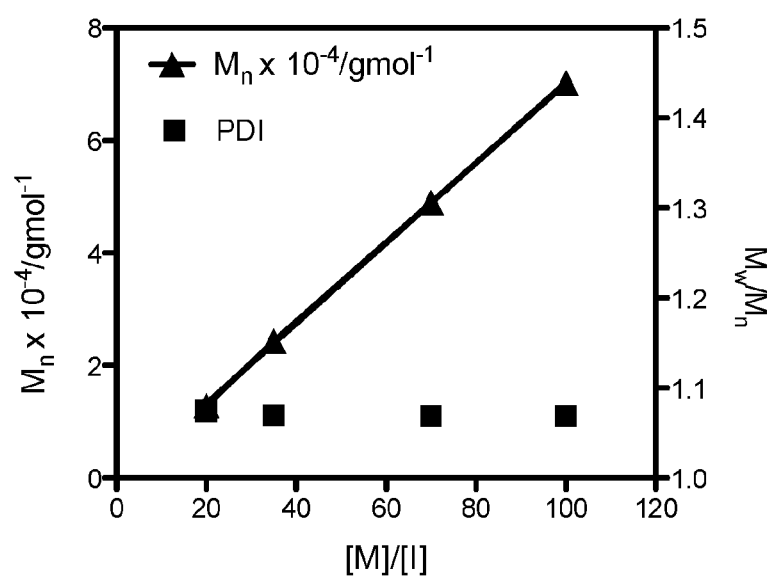
FIG. 16 shows the number average molecular weight ($M_n$, ▲) of poly(rac-$E^{P2}$) as a function of monomer to Co(PMe₃)₄ intiator ratio ([M]/[I]) in THF at 20° C. Polydispersity index (PDI) (■) was determined using GPC/LS.
Figure 17A:
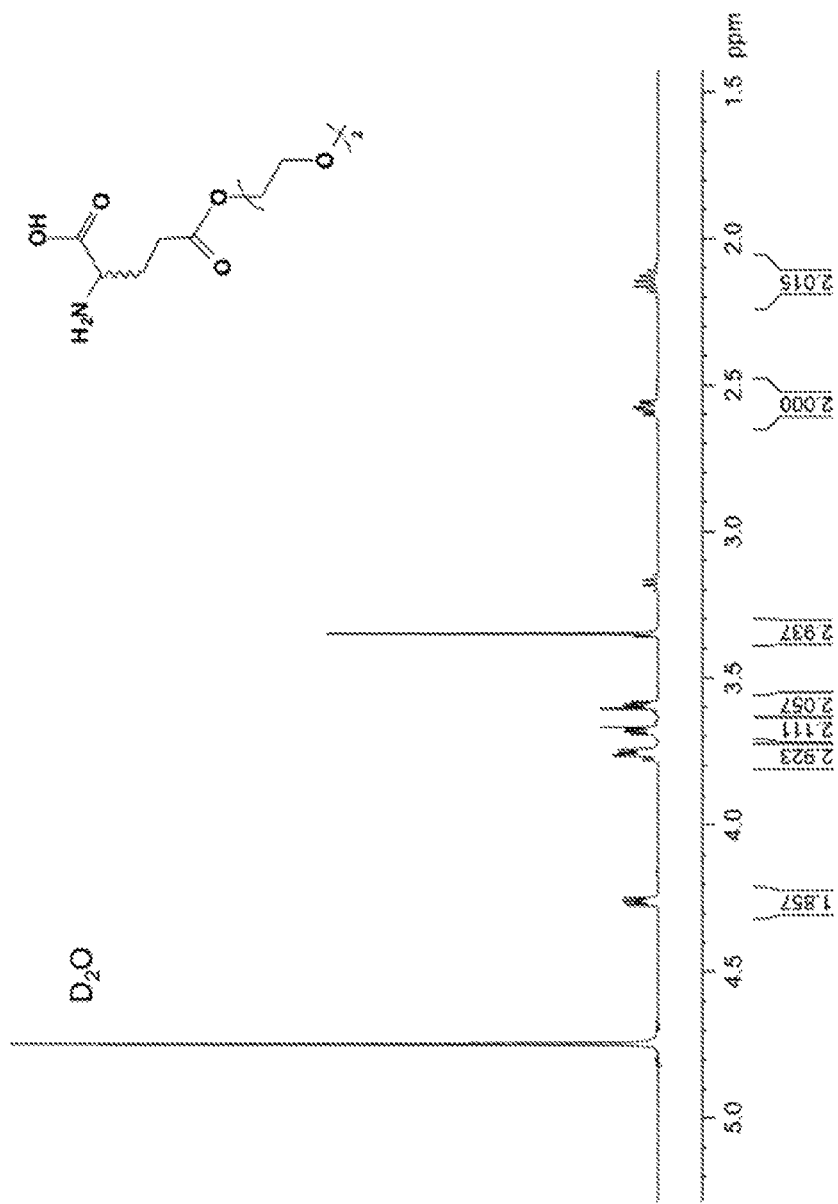
FIG. 17 shows NMR results of various compounds.
Figure 17B:
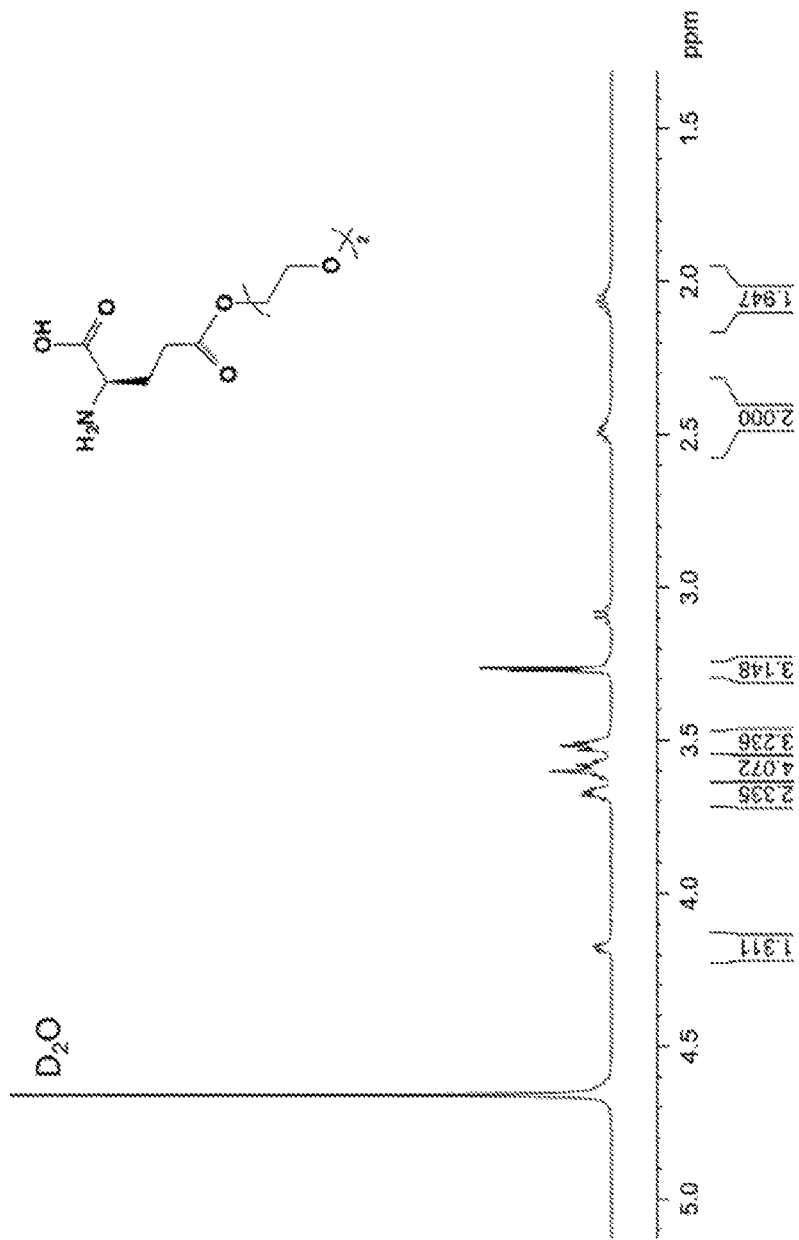
Figure 17C:
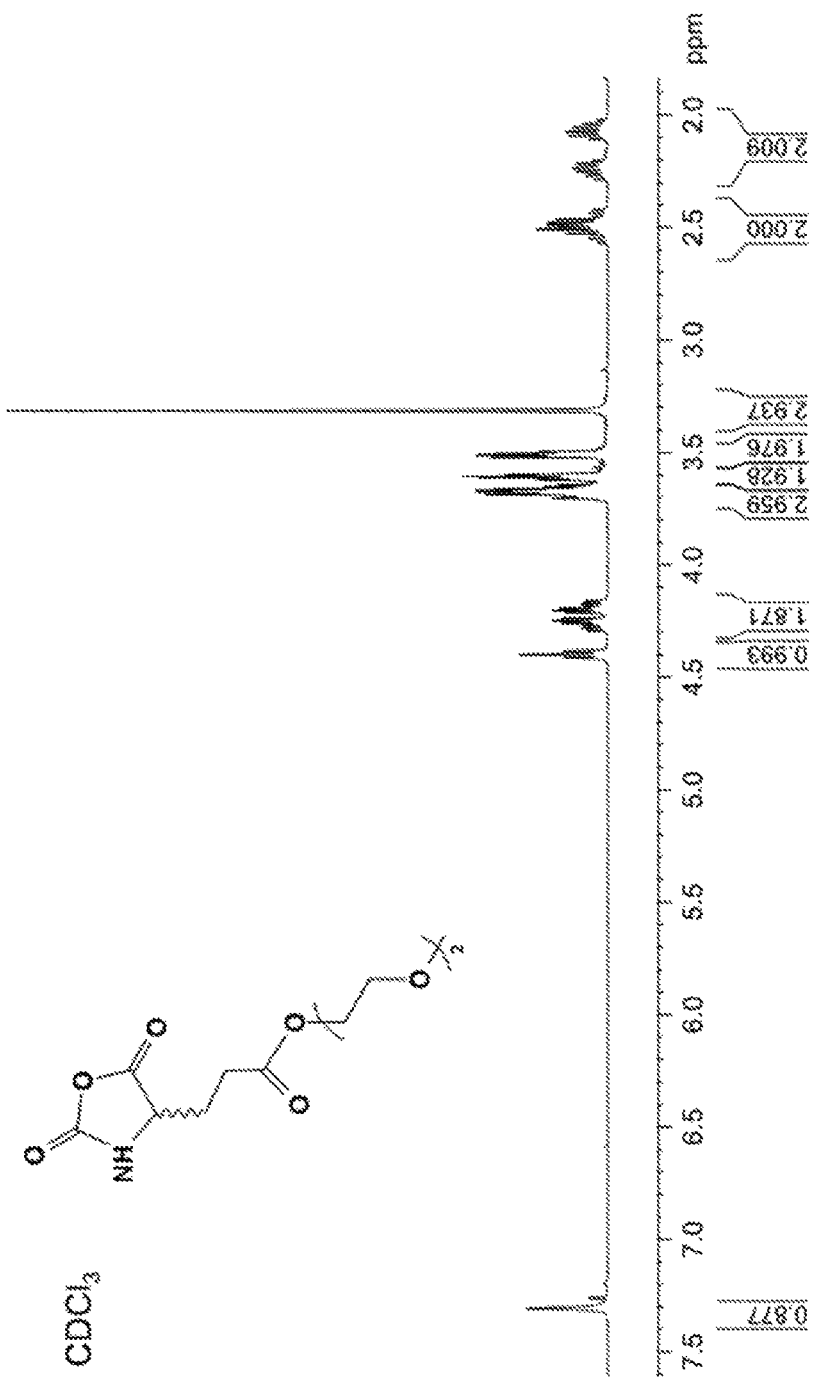
Figure 17D:
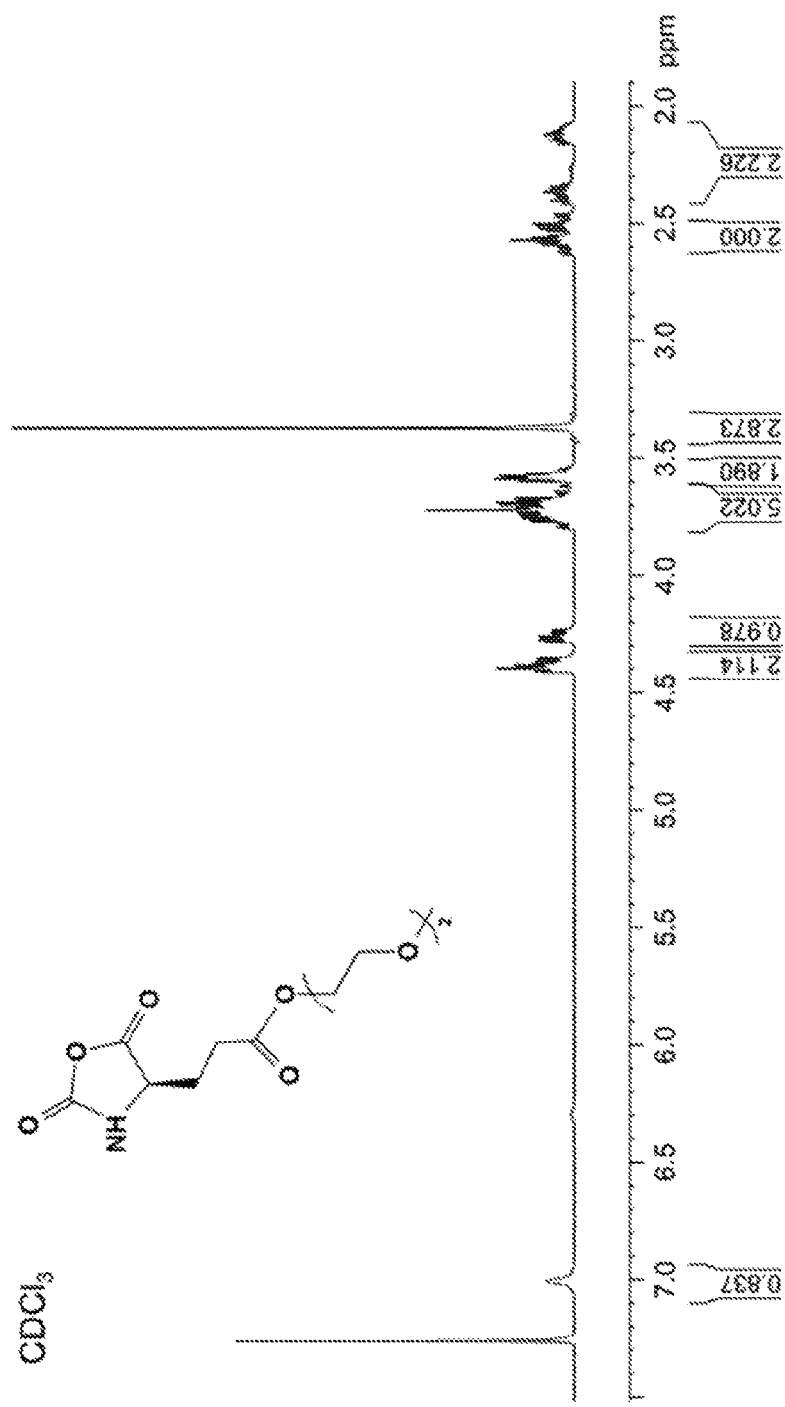
Figure 17E:
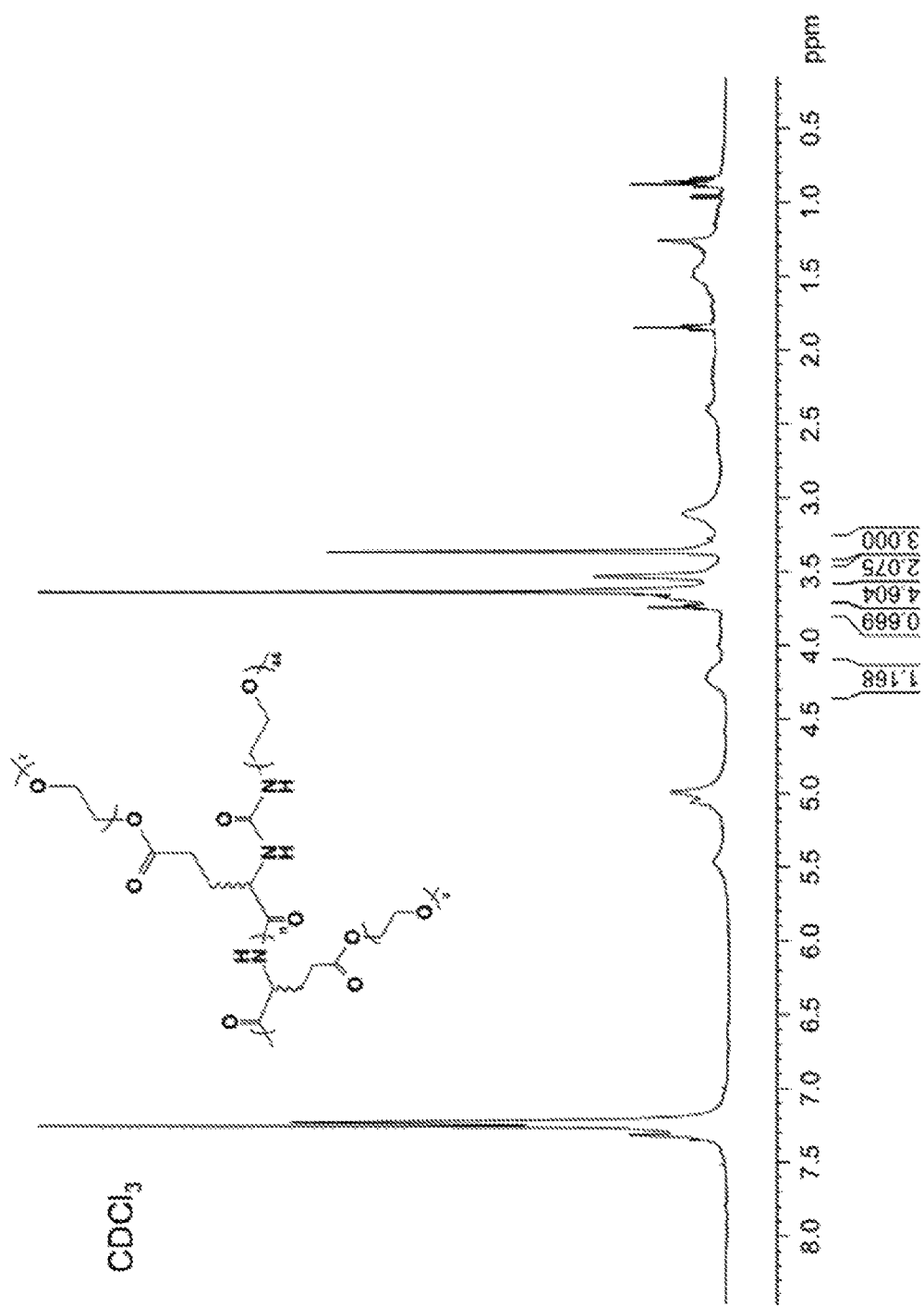
Figure 17F:
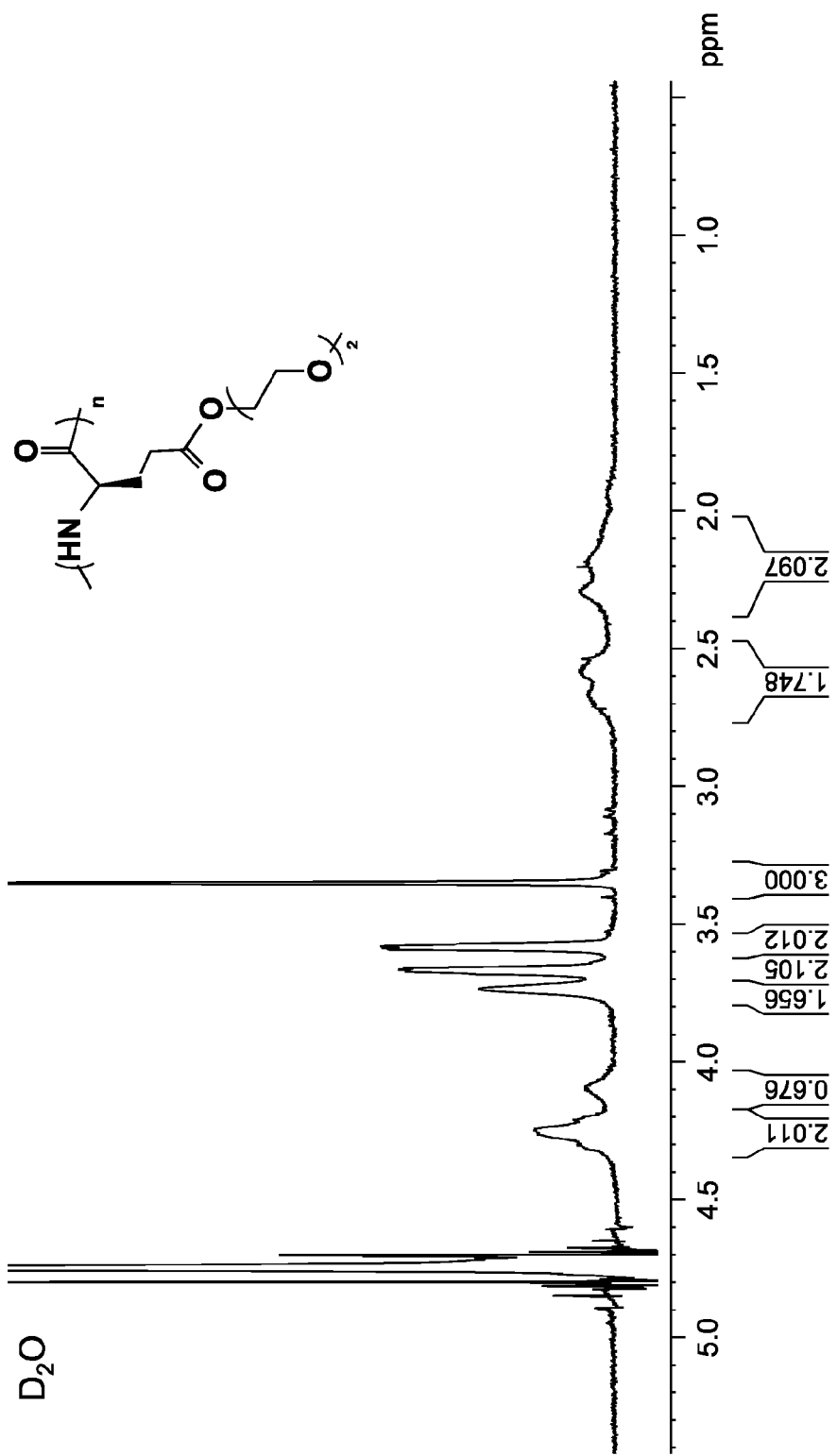
Figure 17G:
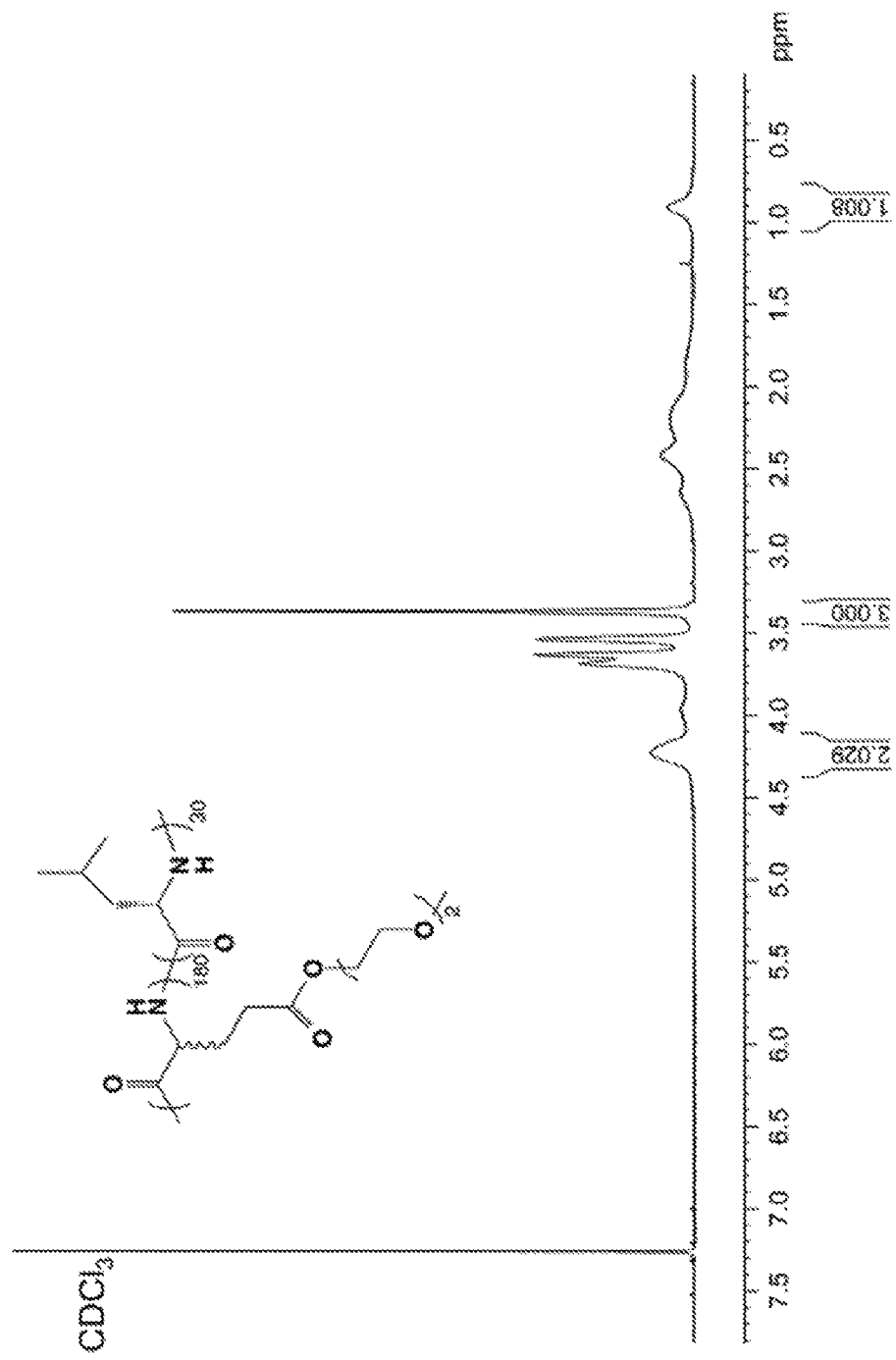
Figure 17H:
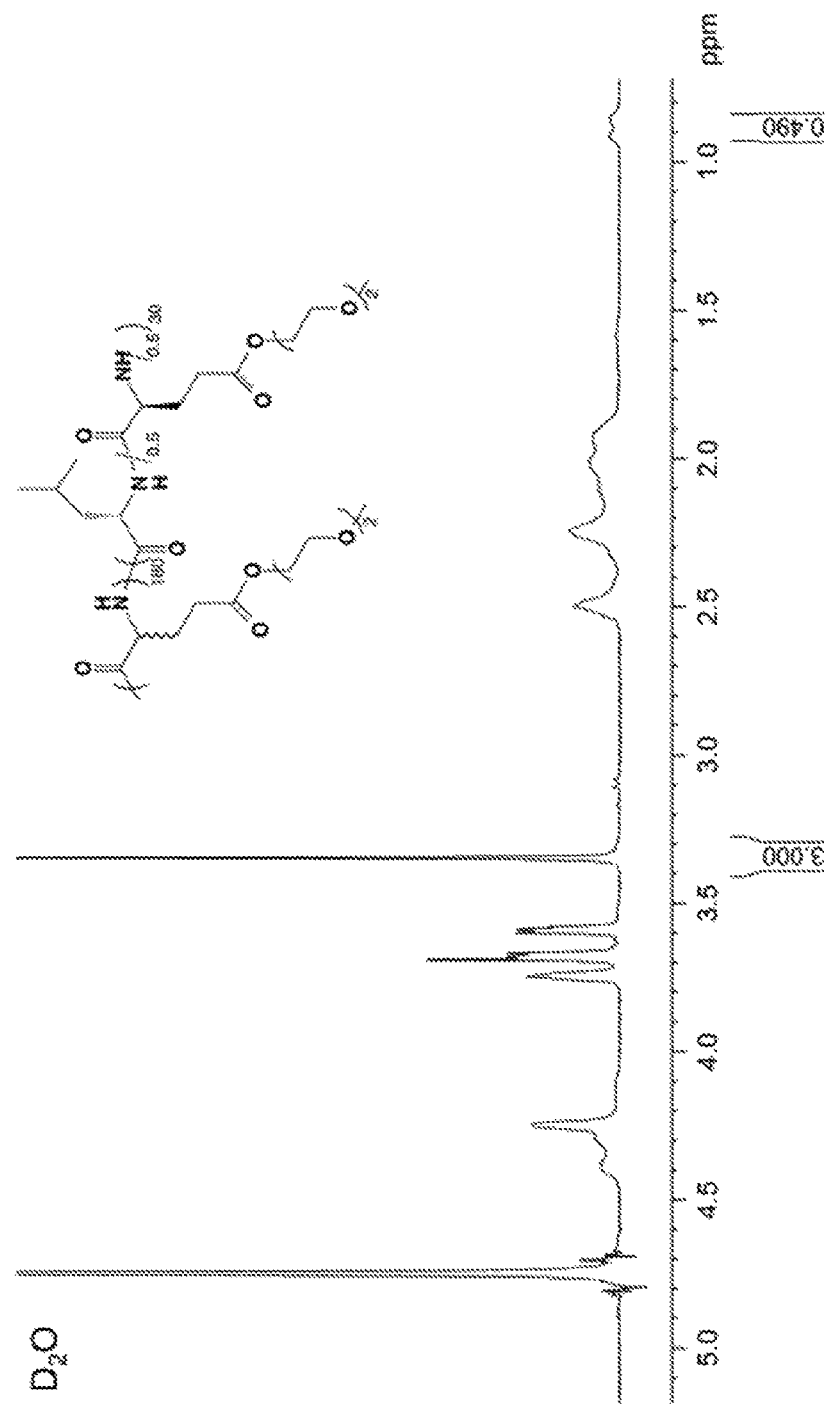

General Polypeptide Synthesis $DCH_T$ and $DCH_{EO}$ samples were designed with average total lengths of around 200 residues, and contained either poly(L-leucine), L, poly(γ-[2-(2-methoxyethoxy)ethyl]-L-glutamate-stat-L-leucine), ($E^{P2}$/L), or poly(γ-(2-methoxyethyl)-L-glutamate-stat-γ-[2-(2-methoxyethoxy)ethyl]-L-glutamate-stat-L-leucine), ($E^{P1}$/$E^{P2}$/L), as the hydrophobic domain, and poly(γ-[2-(2-methoxyethoxy)ethyl]-rac-glutamate), (rac-$E^{P2}$), as the hydrophilic domain (FIG. 3). $DCH_T$ and $DCH_{EO}$ were synthesized by sequential copolymerization of desired NCA monomers using the transition metal initiator $Co(PMe_3)_4$ in THF according to published procedures [12]. All copolymerization reactions were performed in a dinitrogen filled glovebox using anhydrous solvents. Isolated yields of the purified copolymers ranged between 90% and 95%. Relative copolypeptide compositions (FIG. 3) were determined using $^1H$ NMR and were found to be within 1% of predicted values. Chain lengths of initial poly(rac-$E^{P2}$) segments were determined using end-capping analysis (Table 5, FIG. 16) [22]. NMR results shown in FIG. 17.

TABLE 5

Homopolymerization data for poly(rac-$E^{P2}$), prepared using $Co(PMe_3)_4$ in THF at 20° C.

| Monomer[a] | $M_n$[b] | DP[c] | yield (%)[d] |
|---|---|---|---|
| 20 rac-$E^{P2}$ NCA | 12,900 | 56 | 96 |
| 35 rac-$E^{P2}$ NCA | 24,320 | 105 | 97 |
| 70 rac-$E^{P2}$ NCA | 48,960 | 212 | 99 |
| 100 rac-$E^{P2}$ NCA | 70,220 | 304 | 98 |

[a]Number indicates equivalents of monomer per $Co(PMe_3)_4$.
[b]Number average molecular weight of poly(rac-$E^{P2}$) determined by end-capping with polyethylene glycol (PEG44) ($M_n$ = 2000 Da) followed by $^1H$ NMR analysis. [1]
[c]Number average degree of polymerization of poly(rac-$E^{P2}$) determined from $^1H$ NMR analysis.
[d]Total isolated yield of poly(rac-$E^{P2}$). NMR results shown in FIG. 17.

Representative Synthesis of a $DCH_T$ Sample: (rac-$E^{P2}$)$_{180}$($E^{P2}_{0.5}$/$L_{0.5}$)$_{30}$ In a dinitrogen filled glovebox, a solution of $Co(PMe_3)_4$ (22 mg, 0.059 mmol) in THF (20 mg/ml) was rapidly added, via syringe, to a solution of rac-$E^{P2}$ NCA (1.0 g, 3.6 mmol) in THF (50 mg/ml). The reaction was stirred at 20° C. and polymerization progress was monitored by FTIR. Polymerization reactions were generally completed within 4 hours. Immediately upon polymerization completion, an aliquot was removed for end-capping analysis to determine the length of the poly(rac-$E^{P2}$) segment [22]. A solution of a 1:1 molar mixture of L-leucine NCA (47.7 mg, 0.31 mmol) and L-$E^{P2}$ NCA (83.3 mg, 0.31 mmol) in THF (50 mg/ml) was then added to the active poly(rac-$E^{P2}$) segment, and the reaction was monitored by FTIR. Copolymerization was generally complete within another 2 hours. After complete NCA consumption, the reaction was removed from the glovebox and diethyl ether (30 ml) was then added to precipitate the copolymer. The product was isolated by centrifugation and was washed with ether twice more before re-suspending in water. The copolymer was dispersed in DI water and then placed In a dialysis bag (MWCO=2000 Da) and dialyzed exhaustively against DI water for four days in a sterile container. Lyophilization of the resulting clear suspension gave 720 mg poly(rac-$E^{P2}$)$_{180}$-block-poly(L-$E^{P2}$-stat-L-leucine)$_{30}$, (rac-$E^{P2}$)$_{180}$($E^{P2}_{0.5}$/$L_{0.5}$)$_{30}$ (90% yield) as a fluffy white solid. $^1H$ NMR analysis of this material was used to determine the actual copolymer composition, which was found to be (rac-$E^{P2}$)$_{180}$($E^{P2}_{0.5}$/$L_{0.5}$)$_{28}$ (Table 6). NMR results shown in FIG. 17.

TABLE 6

Copolymerization data for diblock copolypeptide syntheses.

| Sample Number | Predicted composition | $M_n$[a] | $M_w/M_n$[b] | rac-$E^{P2}$ DP[a] | Found compostion[c] | Yield (%)[d] |
|---|---|---|---|---|---|---|
| 1 | (rac-$E^{P2}$)$_{180}$L$_{20}$ | 41,590 | 1.03 | 180 | (rac-$E^{P2}$)$_{180}$L$_{21}$ | 92 |
| | (rac-$E^{P2}$)$_{180}$L$_{30}$ | 41,590 | 1.03 | 180 | (rac-$E^{P2}$)$_{180}$L$_{30}$ | 95 |
| | (rac-$E^{P2}$)$_{180}$L$_{40}$ | 41,590 | 1.03 | 180 | (rac-$E^{P2}$)$_{180}$L$_{38}$ | 90 |

TABLE 6-continued

Copolymerization data for diblock copolypeptide syntheses.

| Sample Number | Predicted composition | $M_n^{(a)}$ | $M_w/M_n^{(b)}$ | rac-$E^{P2}$ $DP^{(a)}$ | Found compostion$^{(c)}$ | Yield (%)$^{(d)}$ |
|---|---|---|---|---|---|---|
| 2 | (rac-$E^{P2}$)$_{180}E^{P2}_{30}L_{20}$ | 42,040 | 1.08 | 182 | (rac-$E^{P2}$)$_{182}E^{P2}_{28}L_{19}$ | 92 |
| 3 | (rac-$E^{P2}$)$_{180}E^{P2}_{20}L_{30}$ | 42,040 | 1.08 | 182 | (rac-$E^{P2}$)$_{182}E^{P2}_{21}L_{30}$ | 94 |
| 4 | (rac-$E^{P2}$)$_{180}E^{P2}_{10}L_{30}$ | 42,040 | 1.08 | 182 | (rac-$E^{P2}$)$_{182}E^{P2}_{11}L_{29}$ | 90 |
| 5 | (rac-$E^{P2}$)$_{180}L_{20}E^{P2}_{30}$ | 41,350 | 1.10 | 179 | (rac-$E^{P2}$)$_{179}L_{20}E^{P2}_{29}$ | 93 |
| 6 | (rac-$E^{P2}$)$_{180}L_{30}E^{P2}_{20}$ | 41,350 | 1.10 | 179 | (rac-$E^{P2}$)$_{179}L_{30}E^{P2}_{21}$ | 95 |
| 7 | (rac-$E^{P2}$)$_{180}L_{30}E^{P2}_{10}$ | 41,350 | 1.10 | 179 | (rac-$E^{P2}$)$_{179}L_{30}E^{P2}_{11}$ | 93 |
| 8 | (rac-$E^{P2}$)$_{180}(E^{P2}_{0.5}/L_{0.5})_{20}$ | 41,810 | 1.07 | 181 | (rac-$E^{P2}$)$_{181}(E^{P2}_{0.5}/L_{0.5})_{19}$ | 94 |
| 9 | (rac-$E^{P2}$)$_{180}(E^{P2}_{0.5}/L_{0.5})_{30}$ | 41,810 | 1.07 | 181 | (rac-$E^{P2}$)$_{181}(E^{P2}_{0.5}/L_{0.5})_{28}$ | 90 |
| 10 | (rac-$E^{P2}$)$_{180}(E^{P2}_{0.5}/L_{0.5})_{40}$ | 41,810 | 1.07 | 181 | (rac-$E^{P2}$)$_{181}(E^{P2}_{0.5}/L_{0.5})_{40}$ | 97 |
| 11 | (rac-$E^{P2}$)$_{180}(E^{P1}_{0.1}/E^{P2}_{0.4}/L_{0.5})_{30}$ | 41,110 | 1.09 | 178 | (rac-$E^{P2}$)$_{178}(E^{P1}_{0.1}/E^{P2}_{0.4}/L_{0.5})_{30}$ | 92 |
| 12 | (rac-$E^{P2}$)$_{180}(E^{P1}_{0.2}/E^{P2}_{0.3}L_{0.5})_{30}$ | 41,110 | 1.09 | 178 | (rac-$E^{P2}$)$_{178}(E^{P1}_{0.2}/E^{P2}_{0.3}/L_{0.5})_{30}$ | 91 |
| 13 | (rac-$E^{P2}$)$_{180}(E^{P2}_{0.5}/A_{0.5})_{40}$ | 41,620 | 1.12 | 180 | (rac-$E^{P2}$)$_{180}(E^{P2}_{0.5}/A_{0.5})_{38}$ | 90 |
| 14 | (rac-$E^{P2}$)$_{180}(E^{P2}_{0.5}/A_{0.5})_{40}$ | 41,620 | 1.12 | 180 | (rac-$E^{P2}$)$_{180}(E^{P2}_{0.5}/A_{0.5})_{49}$ | 92 |

$^{(a)}M_n$ and DP (degree of polymerization) for initial poly(rac-$E^{P2}$) segments determined using end-capping analysis. [1]
$^{(b)}M_w/M_n$ = Polydispersity index determined using GPC/LS.
$^{(c)}$Determined from $^1$H NMR integrations.
$^{(d)}$Total isolated yield of purified block copolypeptides. NMR results shown in FIG. 17.

Preparation of Fluorescence-Tagged DCH (AMCA-X-$K_{180}L_{30}$)

For a few test cases, DCH$_T$ were mixed with a small amount of $K_{180}L_{30}$ conjugated with a fluorescent dye to track hydrogel location in vivo. Fluorescent tagging of lysine ε-amine groups was performed using AMCA-X [6-((7-Amino-4-methylcoumarin-3-acetyl)amino)hexanoic acid] (AnaSpec, Cat #81207) as a blue fluorescent tag, which was attached using NHS-EDC coupling chemistry. In this procedure, $K_{180}L_{30}$ powder (3.2 mmol) was dissolved in PBS buffer (pH=6.5, 30 ml, 0.1 M). To the polypeptide suspension, 2 equivalents of NHS (N-hydroxysuccinimide) in PBS buffer (pH=6.5), 10 equivalents of EDC (1-ethyl-3-(3-dimethylaminopropyl) carbodiimide) in PBS buffer (pH 1=6.5), and 1 equivalent of AMCA-X in DMSO per copolypeptide chain (corresponding to 2.8% of the available lysine amines) were added, and the mixture was stirred for 16 hours. For purification, the sample was covered in aluminum foil to protect from light, and then dialyzed (MWCO=2 kDa) for 5 days against pyrogen free water, with dialyzate changes every 12 hours. The tagged polymer (AMCA-X-$K_{180}L_{30}$) was isolated by lyophilization. For use in injections in vivo, AMCA-X-$K_{180}L_{30}$ was mixed with DCH$_T$ samples at a molar ratio of 1:10, respectively.

Rheology Measurements

DCH$_T$ were prepared by rehydrating freeze-dried samples in aqueous phosphate buffered saline pH=7.4 (PBS). Rheological measurements (dynamic) were performed on a strain controlled Reometrics fluids spectrometer RFS II in a cone-plate geometry with diameter of 25 mm and cone angle of 0.02 rad similar to previously described [13]. Strain was set at 10% and the sweep frequency was 1 rad/s. For each sample small-deformation linearity was checked before performing oscillatory measurements. Temperature was increased 0.4° C. every minute during temperature sweep measurements.

Gelation Temperature ($T_G$) Measurements 0.5 ml of 3% DCH$_T$ samples in PBS composed of different hydrophobic segments, or mixed with different amounts of DCH$_{EO}$, were injected into separate 1 cm diameter, flat-bottomed glass vials. All samples were then immersed n a large water bath and equilibrated at 25° C. The temperature of the water bath was increased at a rate of 0.5° C. per min, and the vials were repeatedly inverted to test if gelation (loss of sample flow) had occurred. Once gelation was observed, the bath temperature was defined as the gelation temperature ($T_G$) for that sample. All measurements were performed in triplicate.

Cell Settlement Measurements

NSC prepared as above (2.2.2) were suspended in media or in 2% or 3% DCH$_T$ at 200,000 cells/ml and transferred to 1 ml quartz cuvettes. The absorbance of light through the quartz cuvette at different time points was measured using a PerkinElmer Lambda EZ210 (λ=500 nm) Since suspended cells scatter visible light, a decrease in sample absorbance indicates settling of cells out of the light path due to gravity.

Release of Hydrophilic Molecules from $K_{180}L_{20}$ and DCH$_T$ 0.5 ml of $K_{180}L_{20}$ or DCH$_T$ in PBS containing a test protein (chicken egg white lysozyme (Sigma), chicken egg white ovalbumin (Sigma) or immunoglobin G from bovine serum (Sigma)) was injected into a dialysis cassette (Thermo Scientific) with a membrane molecular weight cut-off of 100 kDa for lysozyme, or 200 kDa for ovalbumin and IgG. The dialysate was PBS for all release studies. The dialysis cassettes containing protein loaded $K_{180}L_{20}$ or DCH$_T$ were warmed to 37° C. before immersing into 37° C. dialysate (200 ml in an amber bottle) without stirring. Aliquots of dialysate (1 ml each) were sampled for analysis after 0, 1, 2, 4, 6, 8, 10, 12, and 24 hours, and the dialysate was stirred briefly for one minute immediately prior to removal of aliquots. The concentrations of test proteins in dialyzate samples were determined by measurement of UV absorption and use of calibration curves for each protein. UV spectra were measured using a PerkinElmer LambdaEZ210 (λ=280 nm). Protein release data were fitted using methods described previously [14].

Anionic lysozyme and neutral lysozyme were prepared by literature procedures where lysine residues in native, cationic chicken egg white lysozyme (30 mg/ml in phosphate buffer at pH 8) were reacted with large excesses (more than 10 equivalents per lysine residue) of succinic anhydride or acetic anhydride, respectively [23, 24]. The reaction pH was kept between 8 and 9 by adding aliquots of 0.1 M NaOH until the pH remained constant. The solutions of modified lysozyme were then separately dialyzed against PBS for four days and then freeze-dried to obtain materials for subsequent studies. The modified lysozymes were both soluble at 10% n PBS buffer and showed no signs of aggregation.

Loading and Release of Hydrophobic Molecules from $DCH_T$

Cholesterol (Sigma, 386.65 g/mol) was used as a model hydrophobic test molecule for in vitro release studies. Cholesterol stock solutions were prepared by dissolving directly in 90% ethanol (3.5 mg/ml). $DCH_T$ was dispersed at 15 mg/ml in 90% ethanol to yield a clear fluid. The $DCH_T$ and cholesterol samples in ethanol were mixed together in the desired proportions and then transferred to 1 cm diameter, flat-bottomed vials. After evaporating the ethanol and water under vacuum to dryness, homogeneous transparent films formed on the bottom of the vials. Either DI water or PBS was added to rehydrate the film, which yielded transparent viscous solutions at room temperature containing the desired amount of cholesterol (up to 1.5 wt. %).

0.5 ml of $DCH_T$ prepared at different concentrations in PBS buffer that contained cholesterol at different concentrations were injected into dialysis cassettes (Thermo Scientific) with membrane molecular weight cut-offs of 20 kDa. The dialysis cassettes with cholesterol loaded $DCH_T$ were warmed to 37° C. before being immersed into 37° C. dialysate. The dialysate was PBS that contained 10 mg/ml BSA to help capture the released hydrophobic molecules. Aliquots of dialysate (1 ml each) were sampled for analysis after 0, 1, 2, 4, 8, 12, 24 and 48 hours. After 2 days, the time interval between sampling was adjusted according to the release kinetics of each sample. The concentrations of cholesterol in dialyzate samples were measured using a calibrated gas chromatography (GC) method [15].

The cholesterol was extracted from an aliquot of dialysate with toluene (0.5 ml×3), and its concentration was quantified using a Shimdazu 6890N gas chromatographic system with a DB-17 capillary column (30 m×0.250 mm×0.15 mm, Agilent Technologies Inc., CA, USA). The DB-17 column has mid-polarity and is suitable for analysis of free steroids. One microliter (1.0 µl) of analyte in toluene was injected into GC system with split/splitless injector and flame ionization detector. The inlet temperature was 250° C. and the split ratio was 10:1. The carrier gas was helium at 2.5 ml/min constant flow. The oven was programmed to start at 250° C., hold for 5 min, followed by increasing temperature at a rate of 5° C./min up to 260° C., and then hold again for 8 min. The total time for GC analysis was 15 min. The detector was set at 300° C. with 200 ml/min air flow, 80 ml/min hydrogen flow, and 40 ml/min helium makeup flow.

Three Dimensional Culture of NSC in $DCH_T$

Primary NSC prepared as above (2.2) were dissociated and re-suspended at a final concentration of $2\times10^5$ cells/µl in either serum-free culture medium (DMEM/F12, Invitrogen) or in 2% or 3% $DCH_T$ prepared in DMEM/F12. Re-suspended NSC were transferred to wells of 96-well cell culture plates or to dialysis cassettes with membrane molecular weight cut-off of 200 kDa and cultured in a 37° C. humidified atmosphere with 5% $CO_2$. Dialysis cassettes containing cells in $DCH_T$ or control cells were submerged n media at 37° C. and incubated for 7 days, and the external media was replaced every 2 days. At desired time points, NSC were harvested and cell viability determined using the MTS assay. For MTS assay of NSC cultured in dialysis cassettes, 100 µl of cell suspension was transferred into 96-well cell culture plate and centrifuged briefly to allow aspiration of the cell culture medium. Fresh medium containing 20% MTS was then added to the cells. The cells were returned to the 002 incubator for 1 hour and then the absorbance at 490 nm (A490) was measured for each well using an Infinite F200 plate reader (Tecan Systems Inc., San Jose, Calif., USA). The background absorbance was read at 700 nm (A700) and subtracted from A490. The relative survival of the cells was quantified by taking the ratio of the (A490-A700) values and comparing between the experimental and control cells.

In Vivo Injections of $DCH_T$ and Stem Cells to Healthy or Injured CNS

Preparation of Non-Ionic $DCH_T$ for In Vivo Injections.

Various DCH compositions that formed gels (FIG. 3) were selected for preliminary in vivo tests and were injected individually into mouse forebrain (see below). Based on numerous in vitro and in vivo observations described herein, an optimized $DCH_T$ formulation includes a blend of $DCH_T$ sample 9 (FIG. 1) admixed with $DCH_{EO}$ sample 1 (FIG. 1) in an equimolar ratio, i.e. 9+1 (1:1). This $DCH_T$ blend of 3% 9+1 (1:1) was used for extensive in vivo testing after injection alone or as a carrier for neural stem cell transplantation.

Preparation of NSC in $DCH_T$ for In Vivo Transplantation.

Primary NSC prepared as above were labeled with the reporter protein, green fluorescent protein (GFP), by using lentiviral vectors expressing fluorescent ZsGreen1 (pLVX, Clontech). For vivo transplantation, NSCs were dissociated and re-suspended at a final concentration of $2\times10^5$ cells/µl in either culture medium or in $DCH_T$ (3% 9+1 (1:1), FIG. 1) prepared as in 2.10.1, and kept on ice until transplantation.

Animals.

In vivo experiments were conducted using either wild-type or transgenic C57Bl6 mice from in house breeding colonies. The transgenic mice used expressed the reporter protein tdTomato (tdT) selectively in GFAP-expressing astroglial cells. These transgenic reporter mice were used as hosts for stem cell transplantation experiments in which all host GFAP-expressing cells were labeled with tdT, including normal, reactive and scar-forming astrocytes, so as to differentiate host from graft derived GFP-labeled astroglial cells. To generate these mice, the ROSA-tdT Cre-recombinase reporter strain was obtained from JAX Laboratories (Bar Harbor, Me.) (JAX strain B6.Cg-Gt(ROSA)26Sortm9 (CAG-tdTomato)HzelJ, stock #007909). These highly efficient ROSA-tdT mice [25] were crossed with mGFAP-Cre mice line 73.12, that selectively and specifically target Cre mediated loxP recombination to GFAP-expressing astroglia throughout the CNS, including after spinal cord injury [26-28]. Offspring of this cross that expressed both transgenes were referred to as mGFAP-Cre-tdT reporter mice. Mice were housed in a 12 hour light/dark cycle in an SPF facility with controlled temperature and humidity and allowed free access to food and water, and all surgical procedures and experiments were conducted according to protocols approved by the Chancellor's Animal Research Committee of the Office for Protection of Research Subjects at UCLA.

Surgical Procedures.

All surgical procedures were performed under sterile conditions with isoflurane in oxygen-enriched air as the general anesthesia and using an operating microscope (Zeiss, Oberkochen, Germany) and rodent stereotaxic apparatus (David Kopf, Tujunga, Calif.). Details of all surgical procedures have been published previously [9, 14, 15, 28, 29]. For injections into the caudate putamen nucleus, the skull was exposed and a burr hole was drilled with a high-speed dental drill. Sterile solutions of 2 µl of $DCH_T$ or PBS, or cells in $DCH_T$ or culture medium (prepared as above in 2.8.1 and 2.8.2). were injected stereotaxically into the center of the caudate putamen nucleus using the target coordinates of 0.5 mm anterior to Bregma, 2.0 mm lateral to Bregma and a depth of 3.0 mm below the cortical surface. For injections into the spinal cord, mice were first given severe crush spinal cord injuries (SCI) using procedures described in detail elsewhere [15, 27-29]. Briefly, after a dorsal laminectomy of a single vertebra, a severe crush injury was made at the level of the T9/T10 spinal cord by using No. 5 Dumont forceps (Fine Science Tools, Foster City, Calif.) that had been ground down to a tip width of 0.5 mm. These forceps were used without a spacer to fully compress the cord laterally from both sides for 5 seconds. Two days after SCI, cells in $DCH_T$ or culture medium (prepared as above in 2.8.2) were injected into single sites in the center of the clearly visible SCI lesions immediately lateral to the central dorsal vein and to a depth of 0.6 mm below the spinal cord surface. All injections into the brain or spinal cord were made at a speed of 0.1 µl per minute using pulled glass micropipettes ground to a beveled tip with 150 to 250 µm inside diameters) connected via specialized connectors and high-pressure tubing (Kopf and Hamilton) to a 10 µl syringe (Hamilton) under the control of a microinfusion pump (Harvard Instruments). All animals were given analgesic immediately prior to surgery and every 12 hours for at least 48 hours post-surgery, and thereafter as necessary. Some animals were given bromodeoxyuridine (BrdU, Sigma) to label dividing cells. BrdU was administered by intraperitoneal injections at 100 mg/kg dissolved in saline plus 0.007N NaOH as a single daily injection starting one day after cell transplantation and continuing for seven days.

Histological Procedures

At survival times of 7 or 21 days after forebrain or spinal cord injections, mice received terminal anesthesia by barbiturate overdose and were perfused transcardially with PBS followed by 10% formalin in PBS and processed for different types of histological procedures as described in detail elsewhere [9, 14, 15, 28, 29]. Brains or spinal cords were removed, post-fixed overnight and cryoprotected in buffered 30% sucrose for at least 2 days. Thirty or 40 µm coronal frozen sections were prepared using a cryostat microtome (Leica, Nussloch, Germany) and stained by immunohistochemistry. The primary antibodies used were rabbit anti-GFAP (1:2000 or 1:20,000; Dako, Carpinteria, Calif.), goat anti-GFP (1:1000, Novus, Littleton, Colo.), rat anti-mouse CD45 (1:2000; BD Pharmingen, San Jose, Calif.), sheep anti-BrdU (1:6000, Maine Biotechnology Services, Portland, Me.), rabbit anti-Iba1 (1:1000, Wako Chemicals, Richmond Va.), rabbit anti-GSM (1:150; BD Pharmingen); mouse anti-NeuN (1:400 or 1:4000 Millipore Biosciences), and rabbit anti-neurofilament M (1:10,000; BD Pharmingen). For brightfield microscopy, the developing agents used were biotinylated anti-rat and anti-rabbit secondary antibodies (Vector, Burlingame, Calif.), biotin-avidin-peroxidase complex (Vector) and diaminobenzidine (DAB, Vector). For cytoarchitecture, Nissl staining was conducted using cresyl violet according to standard procedures. For fluorescence microscopy, the developing agents used were anti-rat and anti-rabbit secondary antibodies conjugated to Alexa 488 (Molecular Probes) or to Cy3 or Cy5 (Vector Labs and Chemicon BD Pharmingen), and 4',6'-diamidino-2-phenylindole dihydrochloride (DAPI, 2 ng/ml; Molecular Probes) was used as a general nuclear stain. Sections were coverslipped using ProLong Gold anti-fade reagent (Invitrogen, Grand Island, N.Y.). Stained sections were examined and photographed using brightfield or fluorescence microscopy and scanning confocal laser microscopy (Zeiss, Oberkochen, Germany).

Solubility Studies on $DCH_T$ Using Thermal Cycling

3% 9+1 (1:1) in DI water was transferred into a sealed 1 ml glass vial and then heated slowly to 90° C. in a water bath to assess copolypeptide solubility as a function of temperature. After incubating at 90° C. for 5 min, the vial was then placed into a 4° C. refrigerator to slowly cool the hydrogel, and was let in the refrigerator for 30 min. This heating-cooling cycle was performed 10 times, and copolypeptide solubility was checked each half-cycle. After all the heating-cooling cycles, the vial was incubated in a 90° C. oven for two days. Under all these conditions, the copolypeptide solution or hydrogel remained clear with no evidence of copolypeptide precipitation.

General Procedure for Preparation of Methoxy Oligoethylene Glycol Glutamate, $E^{Px}$, Amino Acids A modified version of the literature procedure for synthesis of oligoethylene glycol glutamates was followed. To a suspension of L-, D- or rac-glutamate (5.0 g) in ethylene glycol monomethyl ether or diethylene glycol monomethyl ether (25 mL) at 80° C., 5 mL TMSCl (trimethylsilyl chloride) was added dropwise. After stirring for three hours, the viscous solution was poured slowly into a solution of triethylamine and isopropanol (250 mL, 1:1, v:v) to yield white precipitate. The white solid was collected by centrifugation and then reprecipitated from methanol into diethyl ether (1:10, v:v). The solvent was removed from the solid residue under vacuum to give the product ($E^{P1}$, $E^{P2}$, or rac-$E^{P2}$) as a white solid.

γ-(2-methoxyethyl)-L-glutamate ($E^{P1}$)

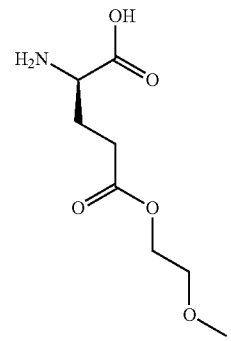

(82.3% yield). $^1$H NMR (400 MHz, $D_2O$): δ 4.30-4.23 (t, 2H), 3.80-3.73 (t, 1H), 3.72-3.66 (t, 2H), 3.40-3.33 (s, 3H), 2.66-2.49 (m, 2H), 2.25-2.07 (m, 2H). NMR results shown in FIG. 17, γ-[2-(2-methoxyethoxy)ethyl]-L-glutamate ($E^{P2}$)

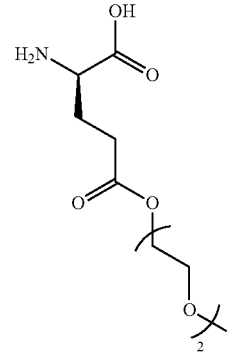

(87.2% yield). $^1$H NMR (400 MHz, D$_2$O): δ 4.31-4.22 (t, 2H), 3.82-3.72 (m, 3H), 3.72-3.64 (m, 2H), 3.63-3.56 (m, 2H), 3.39-3.32 (s, 3H), 2.66-2.49 (m, 2H), 2.25-2.07 (m, 2H). The yield and spectral data for rac-E$^{P2}$ were similar. NMR results shown in FIG. 17.

General Procedure for Preparation of E$^{Px}$ N-carboxyanhydrides

To a solution of E$^{P1}$ (1.00 g, 4.84 mmol) or E$^{P2}$ or rac-E$^{P2}$ (1.00 g, 4.01 mmol) in dry THF (0.15 M) in a Schlenk flask was added a solution of phosgene in toluene (20% (w/v), 2 equiv) via syringe. Caution! Phosgene is extremely hazardous and all manipulations must be performed in a well-ventilated chemical fume hood with proper personal protection and necessary precautions taken to avoid exposure. The reaction was stirred under dinitrogen at 50° C. for 3 hrs, then evaporated to dryness and the flask transferred to a dinitrogen filled glove box. The condensate in the vacuum traps was treated with 30 mL of concentrated aqueous NH$_4$OH to neutralize residual phosgene. Crude E$^{Px}$ NCA, a yellow oil, was purified by column chromatography in 40% THF in hexanes to give the product E$^{Px}$ NCA (0.91 g, 91%) or E$^{P2}$ or rac-E$^{P2}$ NCA (0.85 g, 85%) as a colorless viscous liquid. Spectral data were in agreement with literature values.

γ-(2-methoxyethyl)-L-glutamate N-carboxyanhydride (E$^P_1$ NCA)

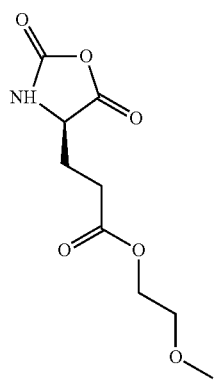 [SMILES: COCCOC(=O)CC[C@H]1NC(=O)OC1=O]

(91.0% yield). $^1$H NMR (400 MHz, CDCl$_3$): δ 7.29-7.14 (br, 1H), 4.46-4.36 (t, 1H), 4.36-4.09 (m, 2H), 3.70-3.51 (t, 2H), 3.49-3.34 (s, 3H), 2.62-2.46 (m, 2H), 2.39-2.03 (m, 2H). NMR results shown in FIG. 17.

γ-[2-(2-methoxyethoxy)ethyl]-L-glutamate N-carboxyanhydride (E$^{P2}$ NCA)

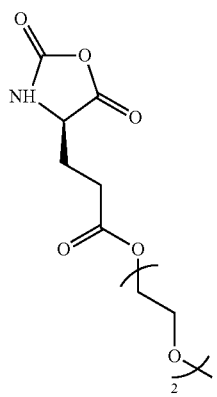

(85% yield). $^1$H NMR (400 MHz, CDCl$_3$): δ 7.30-7.17 (br, 1H), 4.48-4.36 (t, 1H), 4.35-4.13 (m, 2H), 3.76-3.65 (m, 2H), 3.65-3.56 (m, 2H), 3.56-3.46 (m, 2H), 3.39-3.25 (s, 3H), 2.62-3.39 (m, 2H), 2.34-2.01 (m, 2H). The yield and spectral data for rac-E$^{P2}$ NCA were similar. NMR results shown in FIG. 17.

Results

In Vitro Studies

Cytotoxicity of Ionic DCH.

To explore the potential of DCH to support cells for transplantation into the CNS, examined cell suspensions prepared in DCH and maintained in vitro were examined. Well characterized cationic and anionic DCH, $K_{180}L_{20}$ and $E_{180}L_{20}$ respectively, which previous studies had shown were well tolerated and caused no detectable cell damage or toxicity when injected into the CNS in vivo [9, 14, 15] were used. Both $K_{180}L_{20}$ and $E_{180}L_{20}$ exhibited pronounced and rapid toxicity towards suspensions of either HeLa cells or murine bone-marrow mesenchymal stem cells (MSCs) (Table 7). Compared with cells incubated in standard culture media, survival of cells suspended in DCH declined steadily and rapidly over time (Table 7) Toxicity increased with increasing concentration of ionic DCH (Table 7). The cationic DCH, $K_{180}L_{20}$, was substantially more toxic that the anionic DCH, $E_{180}L_{20}$ (Table 7). These results were not entirely surprising based on previous observations showing in vitro cytotoxicity of highly charged ionic polypeptides [30, 31]. A likely explanation for the contrasting observations with ionic DCH in vivo and in vitro, is that in vivo, DCH form discrete deposits that interface with host cells only along borders, whereas in cell suspensions in vitro, cells are fully immersed in and encapsulated by DCH. Under these full immersion conditions, the high charge of the ionic DCH is likely to account for the cell toxicity [32]. In work on other polypeptide assemblies, such as with vesicles and micelles, replacement of cationic hydrophilic segments with non-ionic hydrophilic segments resulted in materials with minimal in vitro cytotoxicity [18, 33, 34]. Therefore DCH were designed to improve their cell compatibility by focusing efforts on the development of non-ionic DCH.

TABLE 7

Viability of cells suspended in cationic ($K_{180}L_{20}$) and anionic ($E_{180}L_{20}$) DCH.

| | \multicolumn{6}{c}{DCH} | | | | |
|---|---|---|---|---|---|---|---|---|---|---|
| | 2% $K_{180}L_{20}$ | | | 2% $E_{180}L_{20}$ | | | 3% $K_{180}L_{20}$ | 3% $E_{180}L_{20}$ | 4% $K_{180}L_{20}$ | 4% $E_{180}L_{20}$ |
| Culture time | 3 hr | 24 hr | 48 hr | 3 hr | 24 hr | 48 hr | 24 hr | 24 hr | 24 hr | 24 hr |
| Hela cells | 0.82 | 0.35 | 0.034 | 0.97 | 0.71 | 0.19 | 0.14 | 0.30 | 0.05 | 0.19 |
| MSC | | 0.14 | | | 0.60 | | 0.02 | 0.26 | | |

Values indicate fraction of cells surviving in DCH compared with culture media at the same time points Design and Preparation of Non-Ionic $DCH_{EO}$ Previous work [18, 33-35] suggested a non-ionic DCH design strategy in which candidate non-ionic hydrophilic segments possess disordered chain conformations in order to promote hydrogel formation. Use of ordered hydrophilic segments (i.e. α-helical) in polypeptide assemblies generally results in formation of rigid sheets that will not form hydrogels [35]. With this in mind, poly(γ-[2-(2-methoxyethoxy)ethyl]rac-glutamate), (rac-$E^{P2}$), was used as a hydrophilic segment to prepare non-ionic DCH (FIG. 1), since this polypeptide is non-ionic, highly water soluble, and possesses a disordered chain conformation due to its racemic residue composition [21].

Diblock copolypeptides were prepared containing hydrophilic (rac-$E^{P2}$) and hydrophobic poly(L-leucine), L, segments with compositions similar to those of ionic DCH, e.g. (rac-$E^{P2}$)$_{180}L_x$, x=20, 30, or 40, and designated this family of copolymers as $DCH_{EO}$ (FIG. 1). These samples formed hydrogels upon direct dissolution in aqueous media at concentrations greater than ca. 2-3 wt %, and were found to possess gel stiffness (storage modulus, G') that increased with hydrophobic L segment chain lengths, similar to ionic DCH (Table 8). These results show that the molecular design criteria used for tuning properties of ionic DCH also apply to formation and tuning of non-ionic $DCH_{EO}$ [10]. This feature allows the straightforward preparation of non-ionic DCH with tunable properties that should have improved cell compatibility, and also retain the desirable characteristics of ionic DCH, such as injectability, tunable rigidity and porosity.

TABLE 8

Storage modulus (G', 1 rad/s) of (rac-$E^{P2}$)$_{180}L_{20}$, (rac-$E^{P2}$)$_{180}L_{30}$ and (rac-$E^{P2}$)$_{180}L_{40}$ at 3% in DI water.

| 3% | (rac-$E^{P2}$)$_{180}L_{20}$ | (rac-$E^{P2}$)$_{180}L_{30}$ | (rac-$E^{P2}$)$_{180}L_{40}$ |
|---|---|---|---|
| G' (Pa) | 47 | 153 | 1362 |

Design and Preparation of Thermoresponsive $DCH_T$

While $DCH_{EO}$ are expected to be more cyto-compatible compared to ionic DCH, the one area they do not improve upon is injectability of the hydrogels into tissues. As demonstrated, many DCH formulations are readily injected into CNS tissues through small bore cannulae. However, there are physical limitations on injectability where DCH that are very stiff can be difficult to extrude through small bore needles due to the high stresses required. The injection of materials as fluids that can then transform into hydrogels in vivo is a strategy that has been used to overcome this issue [17, 36, 37], and would allow the introduction of DCHs with increased stiffness into the CNS. Such materials would also provide advantages in the encapsulation of live cells for grafting into tissues, due to the ease of dispersing cells within a fluid as opposed to a hydrogel. One way to obtain such properties is with a thermoresponsive formulation that would exist as a viscous liquid at ambient temperature (below ca. 30° C.), yet would transform into a rigid hydrogel at physiological temperatures (above ca. 30° C.). If such a formulation could also retain the other desirable characteristics of $DCH_{EO}$, it would be potentially valuable for delivery of molecules and cells into CNS tissues.

Enantiomerically pure poly(γ-[2-(2-methoxyethoxy)ethyl]-glutamate), $E^{P2}$, is α-helical and displays temperature sensitive solubility, (i.e. a lower critical solution temperature) in water, where it is soluble at ambient temperature and precipitates at temperatures above ca. 37° C. [21, 38]. Thus, $E^{P2}$ could be a suitable component to use in development of thermoresponsive DCH, and so triblock copolypeptide designs where $E^{P2}$ residues were incorporated as additional segments either before or after the hydrophobic L segments of $DCH_{EO}$ type copolypeptides were explored (FIG. 1). When dispersed n aqueous media, none of these triblock copolypeptide designs displayed the desired thermoresponsive hydrogel formation characteristics, and instead either formed hydrogels or liquids that did not respond to temperature changes (FIG. 1 samples 2-4, 7), or formed precipitates when temperature was increased to 40° C. (FIG. 1 samples 5, 6).

Figure 4:
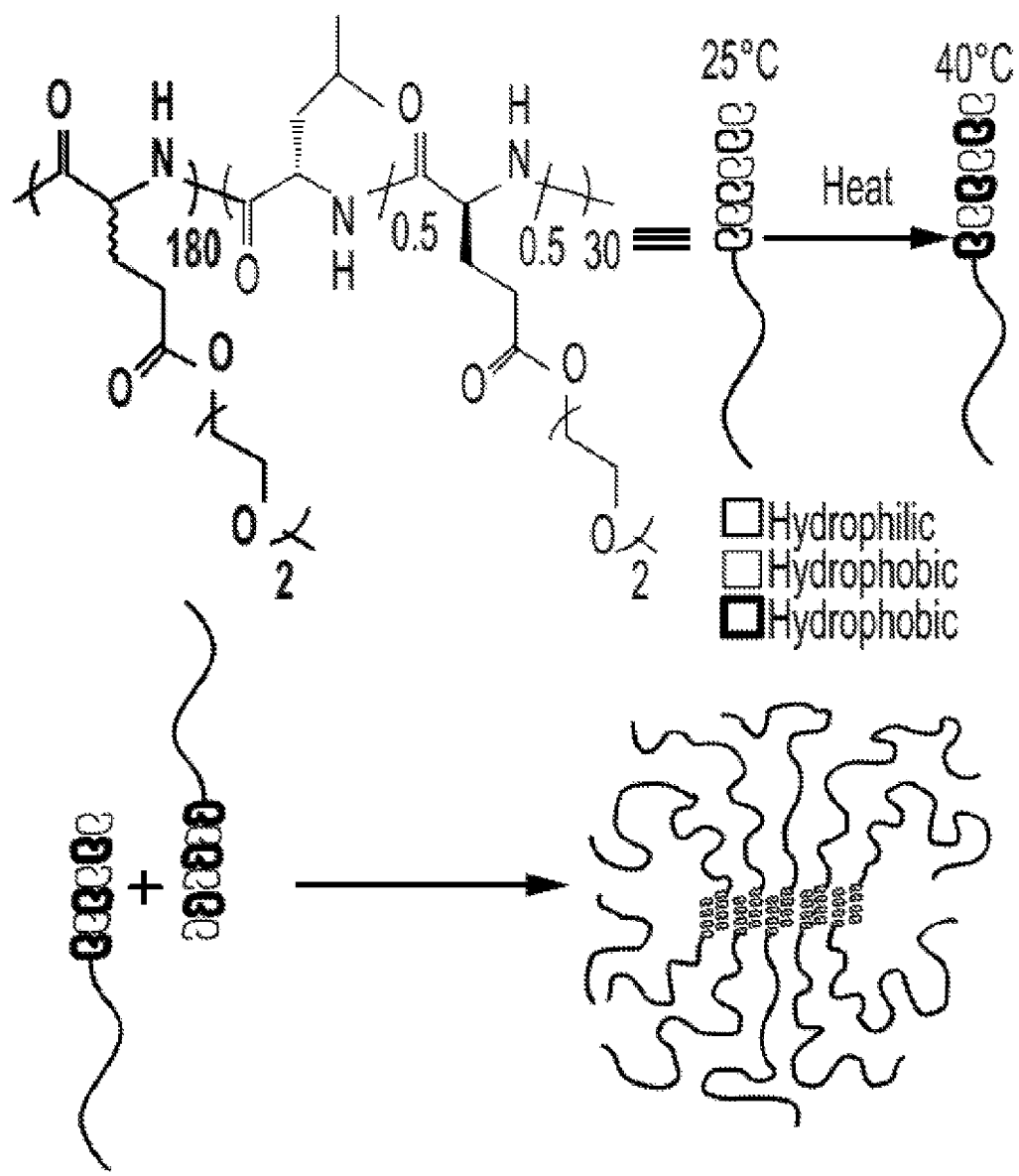
FIG. 4 is a schematic representation, structure, and thermoresponsive gelation process for $DCH_T$ 9. $E^{P2}$ residues in 9 are hydrophilic at <25° C. (blue) and are hydrophobic at >35° C. (orange). In aqueous solutions at >35° C., the hydrophobic thermoresponsive segments in 9 associate to form elongated fibrillar tape-like assemblies that branch and entangle to form 3D hydrogel networks with hydrophilic rac-$E^{P2}$ segments exposed.

In order to encourage better cooperatively between thermosensitive $E^{P2}$ residues and permanently hydrophobic L residues, the copolypeptides were redesigned as diblock copolymers where equimolar $E^{P2}$ and L residues were combined together in statistical sequences as single thermoresponsive segments, e.g. poly(γ-[2-(2-methoxyethoxy)ethyl]-rac-glutamate)-block-poly(γ-[2-(2-methoxyethoxy)ethyl]-L-glutamate-stat-L-leucine), (rac-$E^{P2}$)$_{180}(E^{P2}/L)_x$, x=20, 30, or 40, (FIG. 1 samples 8-10). With thermoresponsive segments 30 residues or longer this design proved successful and gave materials that, when dispersed in aqueous media, flow as liquids at 25° C., and rapidly form rigid hydrogels at 40° C. (FIG. 4). As with other DCH, the properties of these thermoresponsive hydrogels, designated as $DCH_T$, are readily tuned (vide infra) by straightforward synthesis of samples with different hydrophobic segment lengths (FIG. 1 samples 9,10), or with different amino acid compositions (FIG. 1 samples 11,12). All $DCH_T$ samples in FIG. 1 formed completely transparent liquids and gels over a temperature range of 4 to 90° C. when dispersed in aqueous media, and all transitions between liquid and hydrogel states were fully reversible over many heating and cooling cycles (see SI). Also, in either liquid or gel state, all $DCH_T$ (3 wt %) could be injected through 30 Ga needles without difficulty (vide infra), similar to other DCH.

Tuning Properties of $DCH_T$

As noted previously, an advantage of DCH as synthetic biomaterials is the ease at which their physical properties, such as gel stiffness (G') and porosity, are predictably, and often independently, adjusted. In $DCH_T$, gel stiffness is readily adjusted over a wide range by variation of the length of the thermoresponsive segments (FIG. 3A), where increasing segment length results in increased stiffness above the gelation temperature ($T_G$). Alternatively, adjustment of $DCH_T$ concentration can also be used to broadly tune gel stiffness above $T_G$ (FIG. 5B), and also modify gel porosity. These characteristics of $DCH_T$ are similar to properties observed with other ionic DCH [10], indicating that $DCH_T$ are able to incorporate thermoresponsive properties while retaining the other features of DCH. $DCH_T$ are able to respond quickly to temperature changes, with rapid formation of rigid hydrogels occurring within seconds of heating above $T_G$.

In addition to the tuning of properties described above, another important parameter to adjust in $DCH_T$ samples is their transition temperature $T_G$. For biomaterial applications in vivo, it is desirable to fine-tune $T_G$ to both control the rate of gel formation and for use in tissues at different temperatures. The temperature of internal tissues in animals will be close to 37° C., however, exposed tissues, as would be encountered during a surgery may be at temperatures significantly lower than 37° C. The $T_G$ of $DCH_T$ sample 9 was ca. 37° C. in DI water, which may not result in complete gel formation in tissues at or below that temperature. In order to control and lower $T_G$ in $DCH_T$, new samples were prepared where some of the $E^{P2}$ residues in the thermoresponsive segments in $DCH_T$ were replaced with γ-(2-methoxyethyl)-L-glutamate, $E^{P1}$, residues (FIG. 3 samples 11,12).

Figure 5:
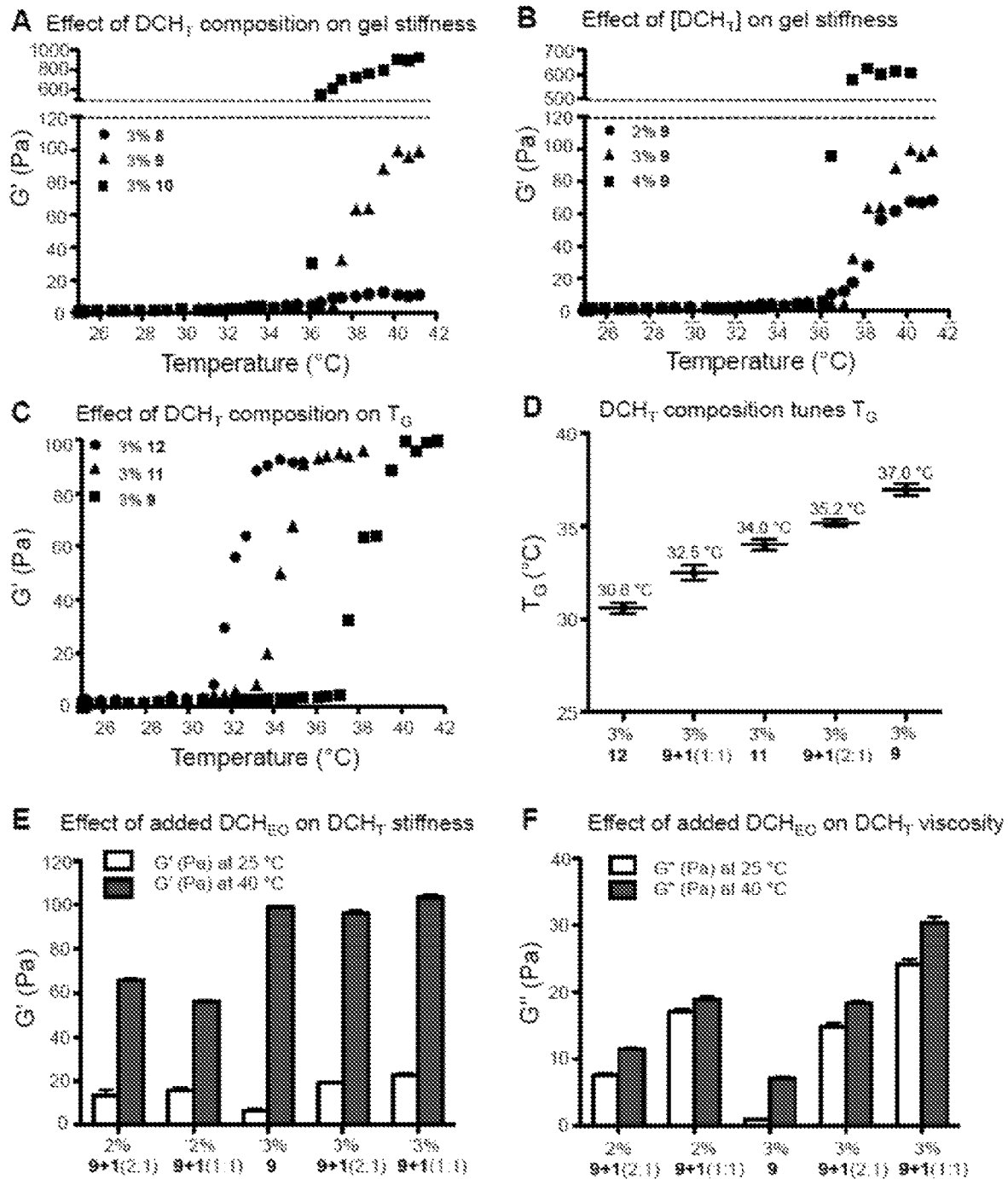
FIG. 5 is shows tuning physical properties of non-ionic $DCH_T$. (A) Graph shows the effects of $DCH_T$ with different thermoresponsive segment lengths in PBS buffer on sample stiffness in PBS buffer (storage modulus, G') as temperature was increased (0.4° C./min). (B) Graph shows the effects of different concentrations of $DCH_T$ 9 in PBS buffer on sample stiffness as temperature was increased (0.4° C./min). (C) Graph shows the effects of different $DCH_T$ compositions in PBS buffer on sample stiffness as temperature was increased (0.4° C./min). (D) Graph shows fine adjustment of gelation temperature ($T_G$) using different compositions or formulations of $DCH_T$ in PBS. (E) Graph of stiffness (G° at 25° C. and 40° C. for different compositions, formulations, and concentrations of $DCH_T$ in PBS. (F) Graph of viscosity (loss modulus, G') at 25° C. and 40° C. for different compositions, formulations, and concentrations of $DCH_T$ in PBS. All G' and G" values measured at 1 Hz. Pa=Pascal units.

The number of ethylene glycol repeats in the side-chains of thermoresponsive polymers is known to affect their thermoresponsive temperatures (i.e. cloud point temperatures) [36-38], with transition temperatures generally lower in samples with fewer ethylene glycol repeats. Hence, incorporation of increasing amounts of $E^{P1}$ residues into $DCH_T$ was expected to result in progressively lower $T_G$ values, which was observed in samples 9, 11, and 12 where $E^{P1}$ content increased from 0 to 20 to 40% of the total $E^{P1}$ and $E^{P2}$ present, respectively (FIG. 5C, 5D). While 40% substitution of $E^{P1}$ for $E^{P2}$ in sample 12 resulted in a significant decrease in $T_G$ (30.6° C.) compared to 9 (37.0° C.), the effect of this substitution on $DCH_T$ stiffness (G) above $T_G$ was minimal (FIG. 5C). These results show that $T_G$ in $DCH_T$ can be adjusted essentially independently of hydrogel stiffness. An alternative method to adjust $T_G$ in $DCH_T$ was also developed, where thermoresponsive $DCH_T$ 9 was physically mixed in different proportions in aqueous media with non-thermoresponsive $DCH_{EO}$ 1 These copolypeptide blends were found to possess lower $T_G$ compared to 9, with $T_G$ decreasing as the fraction of more hydrophobic 1 was increased (FIG. 5D). This approach utilizes the increased hydrophobicity of $DCH_{EO}$ compared to $DCH_T$ to decrease $T_G$ in the blends, and is advantageous in that $T_G$ can be finely tuned by simply varying the mixing ratio of pre-made 9 and 1. Together, both methods described above provide ample means to fine-tune $T_G$ to desired values over a broad temperature range useful for in vivo applications (FIG. 5D).

The formation of blends containing $DCH_{EO}$ and $DCH_T$ also affects other physical properties of the resulting materials, in particular their viscosities, which can be gauged by their loss moduli (G"). To study these physical changes in more detail, storage modulus or stiffness (G') between 9 and its blends with 1 at 25° C. and 40° C. at 3 wt % total DCH concentration were compared (FIG. 5E). These data show that while G' of the samples does not vary significantly above $T_G$, the G' of the blends are different from 9 in the viscous fluid state at 25° C., due to the incorporation of 1, which associates strongly at this temperature. The loss moduli (G"), which are more sensitive to the liquid (i.e. viscous) properties of the samples, show even greater differences between 9 and its blends with 1 (FIG. 5F). At both 25° C. and 40° C., the G" values of the blends of 9 and 1 are much greater that those for pure 9, indicating significantly greater viscosity in the blends, especially at 25° C. Similar data for the blends at 2 wt % total DCH concentration (FIG. 5E, 3F) show these trends persist at different sample concentrations and thus allow precise tuning of $DCH_T$ viscosity at 25° C., and stiffness above $T_G$. Overall, blending of increasing amounts of 1 with 9 resulted in $DCH_T$ with lower $T_G$, as well as increased viscosity at 25° C. Increasing $DCH_T$ viscosity at ambient temperature can be beneficial for preparation of stable suspensions of cells or micro particles within $DCH_T$ (vide infra), which is not possible in pure 9 since it has a viscosity similar to pure water in the liquid state.

Release of Hydrophilic Molecules from $DCH_T$

Figure 6:
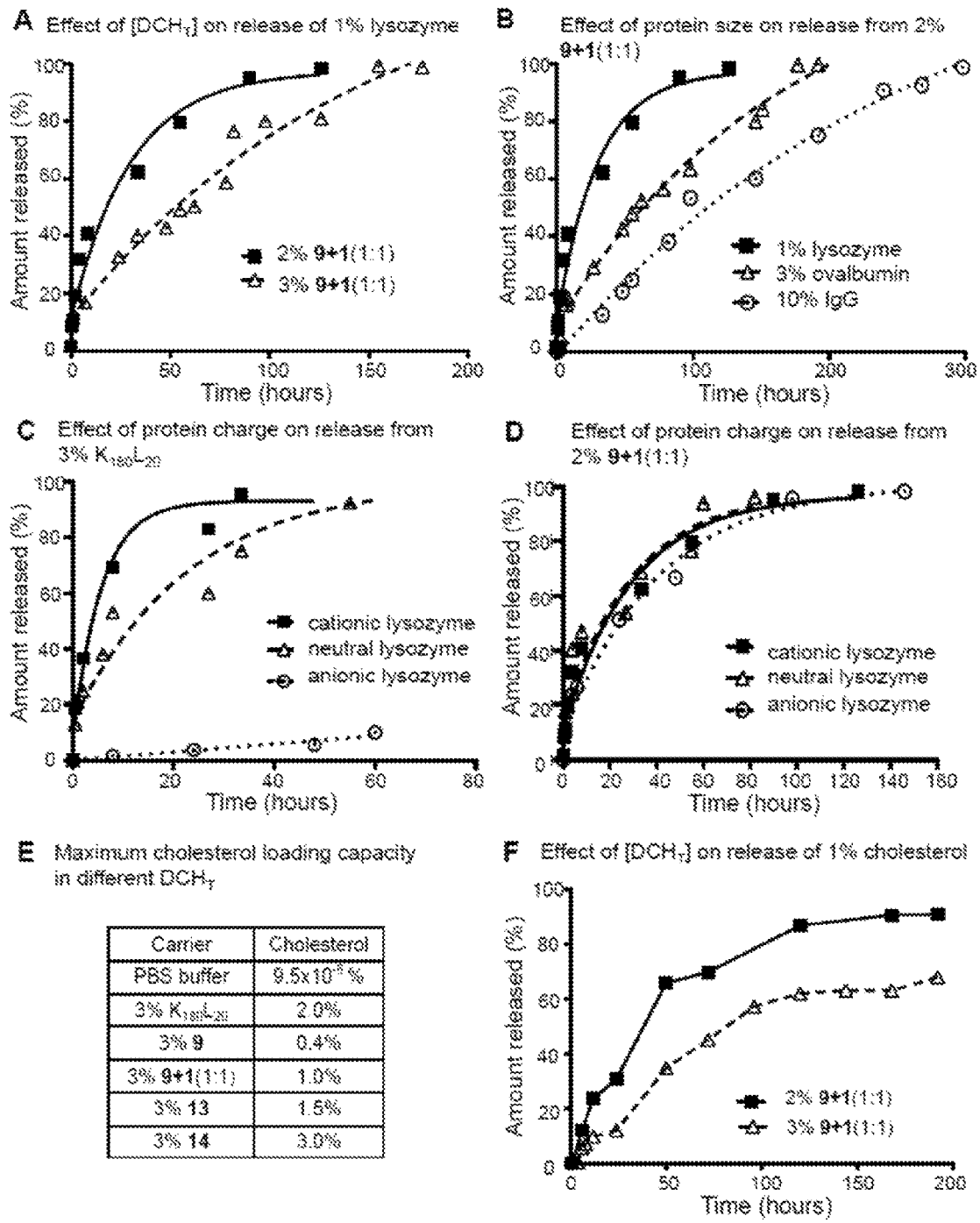
FIG. 6 shows hydrophilic or hydrophobic molecule release kinetics from $DCH_T$ in vitro. (A) Graph shows the effects of optimized $DCH_T$ 9+1 (1:1) concentration on release of model protein 1% lysozyme. (B) Graph shows the effect of molecular weight of model proteins (all at the same molar concentration) on their release from 2% $DCH_T$ 9+1 (1:1). (C) Graph shows the effect of different overall charge on proteins, modeled using native and chemically modified lysozymes, on their release from cationic 3% $K_{180}L_{20}$. (D) Graph shows the effect of different overall charge on proteins, modeled using native and chemically modified lysozymes, on their release from 2% $DCH_T$ 9+1 (1:1). (E) Data showing the effect of different compositions or formulations of $DCH_T$ on their maximum cholesterol loading capacity. (F) Graph shows the effects of $DCH_T$ 9+1 (1:1) concentration on release of model hydrophobic molecule cholesterol. All release studies conducted in PBS buffer at 37° C.

It has been shown that hydrophilic and/or hydrophobic molecules can be loaded into ionic DCH and then released over time either in vitro or in vivo [14, 15]. Here, the ability of $DCH_T$ to perform similar functions was studied, how adjustment of $DCH_T$ or cargo properties affected release was evaluated, and the results with those described earlier for ionic $K_{180}L_{20}$ DCH are compared. To examine the release dynamics of a protein from $DCH_T$, The model protein lysozyme (m.w. 14.7 kDa) dissolved in different concentrations of the optimized $DCH_T$ formulation composed of 9 blended with 1 in an equimolar ratio, i.e. 9+1 (1:1) was used (FIG. 6A). Samples were prepared in PBS, placed into dialysis cassettes and warmed to 37° C., and then suspended in a large reservoir of PBS at 37° C. PBS media was used for these experiments to better mimic physiological conditions. Sampling of the dialyzate at different time intervals allowed measurement of released lysozyme concentrations over time, and these data were fit as described previously [14].

Different $DCH_T$ concentrations were compared to examine how alteration of $DCH_T$ G' and G", which vary in relation to concentration, affect release dynamics. Similar to results for ionic $K_{180}L_{20}$, increased $DCH_T$ concentrations resulted in slower lysozyme release from the hydrogels (FIG. 6A). The effect of protein size on rate of release was also examined by use of soluble model proteins ovalbumin (m.w. ca. 45 kDa) and immunoglobulin G (m.w. ca. 150 kDa) in addition to lysozyme. These three proteins were each dissolved at equimolar concentrations into $DCH_T$ 9+1 (1:1) and their release monitored over time (FIG. 6B). Protein release from $DCH_T$ was found to become slower as protein size increased, as would be consistent with release of different sized molecules from a hydrogel mesh of fixed porosity. These results show that $DCH_T$ concentration, as well as protein size, can both significantly affect release rates of proteins from $DCH_T$ formulations.

Since charged proteins are expected to interact strongly with ionic DCH (i.e. $K_{180}L_{20}$) via polyion complexation [14], a study was conducted to determine how overall protein charge affected their rate of release from $DCH_T$. In this study, proteins of similar size, but different overall charge at pH 7 were prepared by chemical modification of lysozyme. The majority of cationic ammonium groups in native "cationic" lysozyme (isoelectric point (pI) of 11.4) were converted to either anionic carboxylate or neutral acetamide groups, by reaction with excess succinic anhydride or acetic anhydride, respectively, using well characterized methods [23, 24]. The carboxylate modification yields an "anionic" lysozyme (reported pI 4.5) [23], and acetamide modification yields a "neutral" lysozyme (reported pI 10) [24], both of which were found to have good water solubility in PBS media with no signs of aggregation over time. The different overall charges present on these cationic, anionic, and neutral test proteins were found to strongly affect their rates of release from cationic $K_{180}L_{20}$ DCH (FIG. 6C). The slow release of the anionic protein and the fast release of the cationic protein can be explained by polyionic interactions with these highly cationic polyelectrolyte DCH [14]. With non-ionic $DCH_T$, the overall charges of the test proteins had no significant effect on their rates of release (FIG. 6D), with cationic, anionic and neutral lysozymes all releasing at essentially the same rates. These data show that with non-ionic $DCH_T$, rates of protein release are predominantly controlled by gel porosity and protein molecular weight, and their non-ionic nature allows release rates to be decoupled from overall charges present on different cargos.

Release of Hydrophobic Molecules from $DCH_T$

The ability to dissolve and release hydrophobic therapeutic molecules is an attractive feature of traditional DCH that utilizes the hydrophobic segments of the polypeptides as reservoirs for these compounds [15]. However, $DCH_T$ differ from other DCH since they incorporate hydrophilic $E^{P1}$ and $E^{P2}$ components in their thermoresponsive domains that only become hydrophobic above $T_G$. As such, it was advantageous to test if $DCH_T$ were also able to dissolve and provide prolonged release of hydrophobic molecules similar to previously studied ionic DCH [15]. It has been shown that cholesterol is a suitable test molecule for such studies, and now is found that cholesterol is readily dissolved in 3 wt. $DCH_T$ 9+1 (1:1) up to concentrations of 1.0 wt. % n DI water, which is lower than that found for $K_{180}L_{20}$ DCH (FIG. 6E). It is particularly noteworthy that the amount of cholesterol solubilized by $DCH_T$ is substantially greater than the amount soluble in water alone, and it is solubilized both in the gel state at 37° C., as well as in the liquid state at 20° C.

To increase the loading capacity of $DCH_T$, new $DCH_T$ compositions based on L-alanine, A, as opposed to L residues, e.g. poly(γ-[2-(2-methoxyethoxy)ethyl]-rac-glutamate)-block-poly(γ-[2-(2-methoxyethoxy)ethyl]-L-glutamate-stat-L-alanine), $(rac-E^{P2})_{180}(E^{P2}/A)_x$, x=40 or 50 were prepared (FIG. 3 samples 13,14). These samples were prepared since it has been shown that A based hydrophobic segments in DCH are more effective than L segments for solubilization of hydrophobic molecules [15]. Samples 13 and 14 were both found to behave as $DCH_T$ that are liquids at 25° C. and transform to rigid gels at ca. 37° C. With samples 13 and 14 at 3 wt. % in DI water, cholesterol is readily dissolved up to concentrations of 1.5 and 3.0 wt %, respectively (FIG. 6E). These loading capacities are comparable with those previously found for ionic DCH, and show that $DCH_T$ can be tuned to retain advantageous capacity to dissolve hydrophobic molecules while also incorporating thermoresponsive properties.

Once dissolved in $DCH_T$ 9+1 (1:1), cholesterol (1.0 wt %) was found to be released over time when the hydrogels were placed in constant volume dialysis cassettes and dialyzed against PBS buffer containing BSA at 37° C., which is above the $T_G$ for these samples. BSA was added to the dialyzate to capture released cholesterol, which would otherwise precipitate in the aqueous media. Cholesterol release from different concentration $DCH_T$ 9+1 (1:1) samples was monitored over time, and in all cases ca. 65-90% of the loaded cholesterol was released into the dialysate over a period of days, with the remainder still encapsulated in the DCH (FIG. 6F). Similar to results previously obtained for ionic DCH [15], increasing the $DCH_T$ carrier concentration resulted in slower release of cholesterol, which can be advantageous for avoiding a "burst" type release of molecules. Overall, these data show that the adjustable parameters available within $DCH_T$ can be used to predictably tune both loading capacity and release profiles of cholesterol in these hydrogels. In view of the present description, persons skilled in the art can thus make suitable adjustments of these parameters.

In Vitro Viability of Cells Suspended in $DCH_T$

Figure 7:
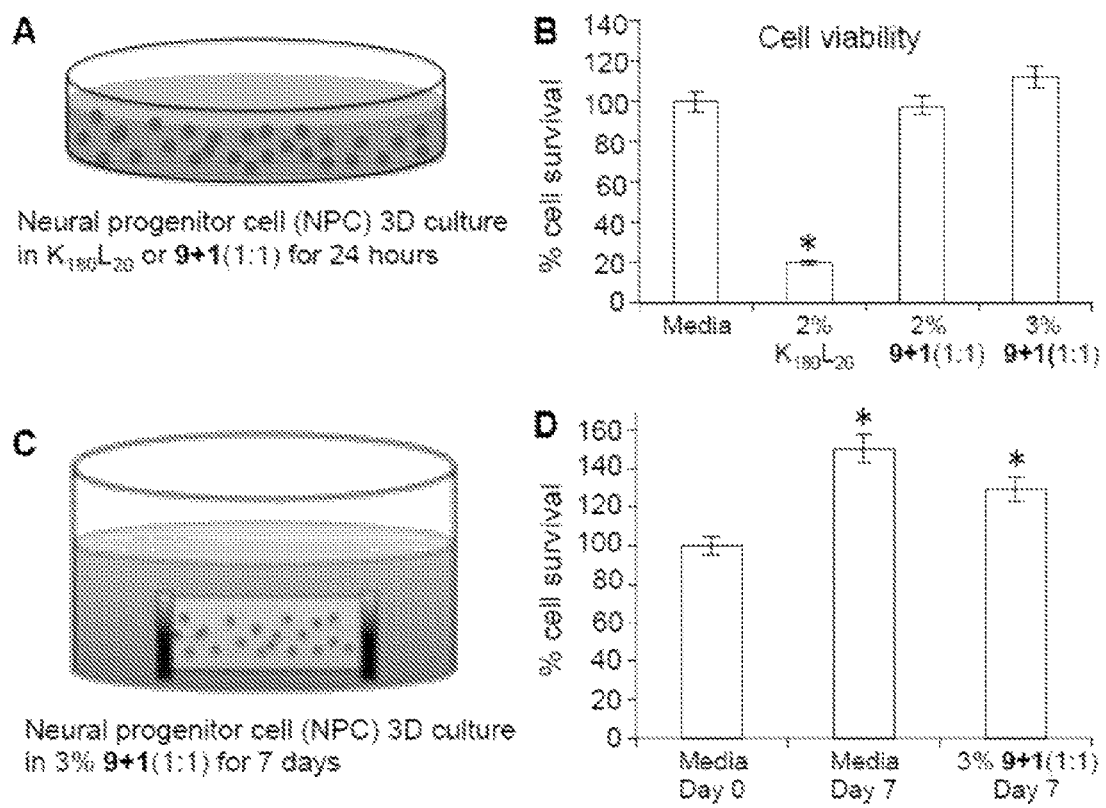
FIG. 7 shows the viability of NPC suspended in $DCH_T$ in vitro. (A) Schematic representation of NPC suspended in $DCH_T$ 9+1 (1:1) for 3D culture in a 24 hour study. (B) Graph shows that the viability of NPC did not differ after culturing for 24 hours in cell culture media or $DCH_T$ 9+1 (1:1), whereas viability was significantly reduced to less than 20% after incubation in cationic 3% $K_{180}L_{20}$. *p<0.001 (ANOVA with post-hoc Newman-Keuls) (n=3 cultures) (C) Schematic representation of NPC suspension within $DCH_T$ 9+1 (1:1) for 3D culture in a 7 day study. (D) Graph shows significant increases in the numbers of NPC after culturing for 7 days in either cell culture media or 3% $DCH_T$ 9+1 (1:1) relative to the starting number of NPC. There was no significant difference in the number of NPC after culturing in cell culture media or 3% $DCH_T$ 9+1 (1:1) for 7 days. *p<0.001 (ANOVA with post-hoc Newman-Keuls) (n=3 cultures).

Preliminary experiments indicated that the viability of HeLa cells was equivalent in $DCH_{EO}$ or $DCH_T$ compared with cell culture media over 48 hours in vitro at 37° C. (data not shown). Additional studies were conducted to compare the viability of NSC in $DCH_T$ versus ionic DCH in vitro. NSC were suspended in either $K_{180}L_{20}$ DCH or $DCH_T$ 9+1 (1:1) in culture medium (FIG. 7A) and incubated at 37° C., which is above the $T_G$ for this $DCH_T$. After 24 hours, cell viability was measured using the MTS assay relative to NSC in media only (FIG. 7B). Cationic $K_{180}L_{20}$ DCH was highly toxic to NSC, consistent with earlier studies and with the properties of cationic polymers in general [30, 31]. In contrast, both 2% and 3% $DCH_T$ 9+1 (1:1) samples displayed no significant cytotoxicity (FIG. 7B) at this time point.

To assess cell viability in $DCH_T$ over longer time periods, NSC were suspended in 3% $DCH_T$ 9+1 (1:1) in culture medium and transferred into dialysis cassettes with a membrane molecular weight cut-off of 200 kDa (FIG. 7C). The use of dialysis cassettes allowed the exchange of cell culture media at different time points without loss of $DCH_T$ material, which can disperse into the media. The high molecular weight cut-off of the membrane allowed small molecules and most proteins to pass through, but did not allow release of the $DCH_T$, which associated into a network. Dialysis cassettes containing cells in $DCH_T$ or control cells were incubated in media at 37° C. for 7 days, after which cell viability was measured using the MTS assay. NSC incubated in both media and 3% $DCH_T$ 9+1 (1:1) increased significantly in number over 7 days relative to the starting number of cells (FIG. 7D) indicating continued proliferation of NSC, as expected. In addition, there was no significant difference in the number of cells after incubation in either media or 3% $DCH_T$ 9+1 (1:1) over 7 days (FIG. 7D). These data demonstrate equivalent survival and proliferation of NSC suspended in $DCH_T$ compared with culture media alone.

Sedimentation and Survival of NSC Suspended in $DCH_T$ During Injections

CNS transplantation requires injection of cells through fine-bore cannulae, which can be hampered by the rapid sedimentation of cells suspended in low viscosity aqueous vehicles. Cell sedimentation and clumping can lead to uneven grafting and can compromise cell viability by increasing shear stress during injection [39, 40]. Grafting vehicles that have sufficient viscosity to delay sedimentation may be advantageous. As described herein, $DCH_T$ can be tuned to have a desired viscosity at ambient temperature by using blends, such as of 9 and 1, without altering their ability to form rigid gel networks above Ta Therefore the ability of various $DCH_T$ blends to delay the sedimentation of suspended NSC was tested, and the viscosity of $DCH_T$ 9+1 (1:1) prepared in culture media at ambient temperature (22° C.) was found sufficient to delay NSC sedimentation at both 2% and 3% concentrations (FIG. 8A). Cell sedimentation was quantified by monitoring absorbance of scattered light, which decreases as cells settle out of the light path. NSC suspended in standard culture media rapidly settled out of suspension, whereas NSC suspended in $DCH_T$ 9+1 (1:1) at 22° C. gave stable suspensions that showed negligible sedimentation for up to one hour. Cell transplantation procedures often require the storage of cells on ice for prolonged periods prior to CNS injection. NSC viability did not diminish over six hours while stored on ice while suspended in $DCH_T$ 9+1 (1:1) prepared in culture media, and that viability of NSC stored in this manner was at least as good or better in comparison with NSC storage in culture media alone (FIG. 8B).

The sedimentation of NSC after loading into the cannulae used for CNS injections as also examined. NSC suspended in culture media alone already began to settle during the process of drawing up the cell suspension into the glass micropipettes used for cell injections into the mouse CNS in vivo. These micropipettes are beveled to pointed tips with inner diameters of about 150 to 250 μm. By the end of the 10 minutes required to load 2 μl of injection volume at the rate of 0.2 μl/minute used to load pipettes for in vivo injections, the NSC had routinely sedimented substantively about halfway down the injection volumes and formed large visible clumps (Time 0 in FIG. 8C). After a further 8 minutes, which is less than the time required to correctly place and then complete a CNS injection in vivo, the majority of the NSC had sedimented into large visible clumps at the bottom of micropipettes (FIG. 8C). In striking contrast, NSC suspended in 3% $DCH_T$ 9+1 (1:1) prepared in culture media remained evenly dispersed throughout the entire injection volume and exhibited no detectable evidence of cell sedimentation throughout the period of loading micropipettes and for up to at least 30 minutes thereafter (FIG. 8C), which would allow for ample time to position the micropipettes and complete injections in the absence of sedimentation.

The survival of NSC after passing through the injection micropipettes while suspended in either cell culture media alone or in 3% $DCH_T$ 9+1 (1:1) prepared in culture media was evaluated. Micropipettes were loaded with 2 μl of cell suspensions as above, and cell suspensions were then immediately injected into cell culture wells at a rate of 0.1 μl/minute, using the same conditions followed for in vivo injections. Injected cells were re-suspended in culture media and cell viability was determined immediately and after incubation for an additional six hours. The viability of NSC loaded and injected in culture media alone decreased by over 50% immediately after injection, and fell further after incubation for six hours on ice (FIG. 8D). In striking contrast, the survival of NSC loaded and injected $DCH_T$ was significantly higher by 40% immediately after injection and by almost double after incubation for a further six hours (FIG. 8D). Thus, $DCH_T$ can substantively protect and enhance the survival of NSC during the process of loading and injection through small-bore cannulae.

In Vivo Experimental Design.

The next objectives were (i) to characterize the appearance, properties and effects on host CNS tissue of non-ionic $DCH_T$ injected into healthy CNS, and (ii) to test in a proof-of-concept manner whether these DC $H_T$ could serve as vehicles for transplanting NSC injected into the healthy or injured CNS. As hosts, wild-type (WT) mice or transgenic mGFAP-Cre-tdT mice that expressed the reporter protein tdTomato (tdT) selectively in astroglia were used. Using these transgenic reporter mice as hosts for stem cell transplantation experiments allowed differentiation of host astroglia labeled with tdT from graft derived astroglia labeled with GFP. Based on the in vitro observations described above, and on pilot in vivo injections of $DCH_{EO}$ and $DCH_T$ samples that formed gels (FIG. 3), an optimized non-ionic $DCH_T$ formulation for in vivo use was found to include a blend of $DCH_T$ sample 9 (FIG. 3) admixed with $DCH_{EO}$ sample 1 (FIG. 3) in an equimolar ratio, i.e. 9+1 (1:1). This $DCH_T$ blend of 3% 9+1 (1:1) gave (i) optimal consistency for ease of injection at room temperature (FIG. 5E,F), (ii) optimal survival and delayed sedimentation of suspended cells during transplantation (FIG. 7,8), (iii) efficient loading and sustained release of both hydrophilic and hydrophobic cargo (FIG. 6,), and (iv) gelation at just below normal body temperature (FIG. 5D,E). For these reasons, 3% $DCH_T$ 9+1 (1:1) was used for extensive in vivo testing and characterization and was injected either alone or as a carrier for NSC transplantation into healthy or injured CNS.

Properties of Non-Ionic $DCH_T$ Injected into Mouse Forebrain

Figure 9:
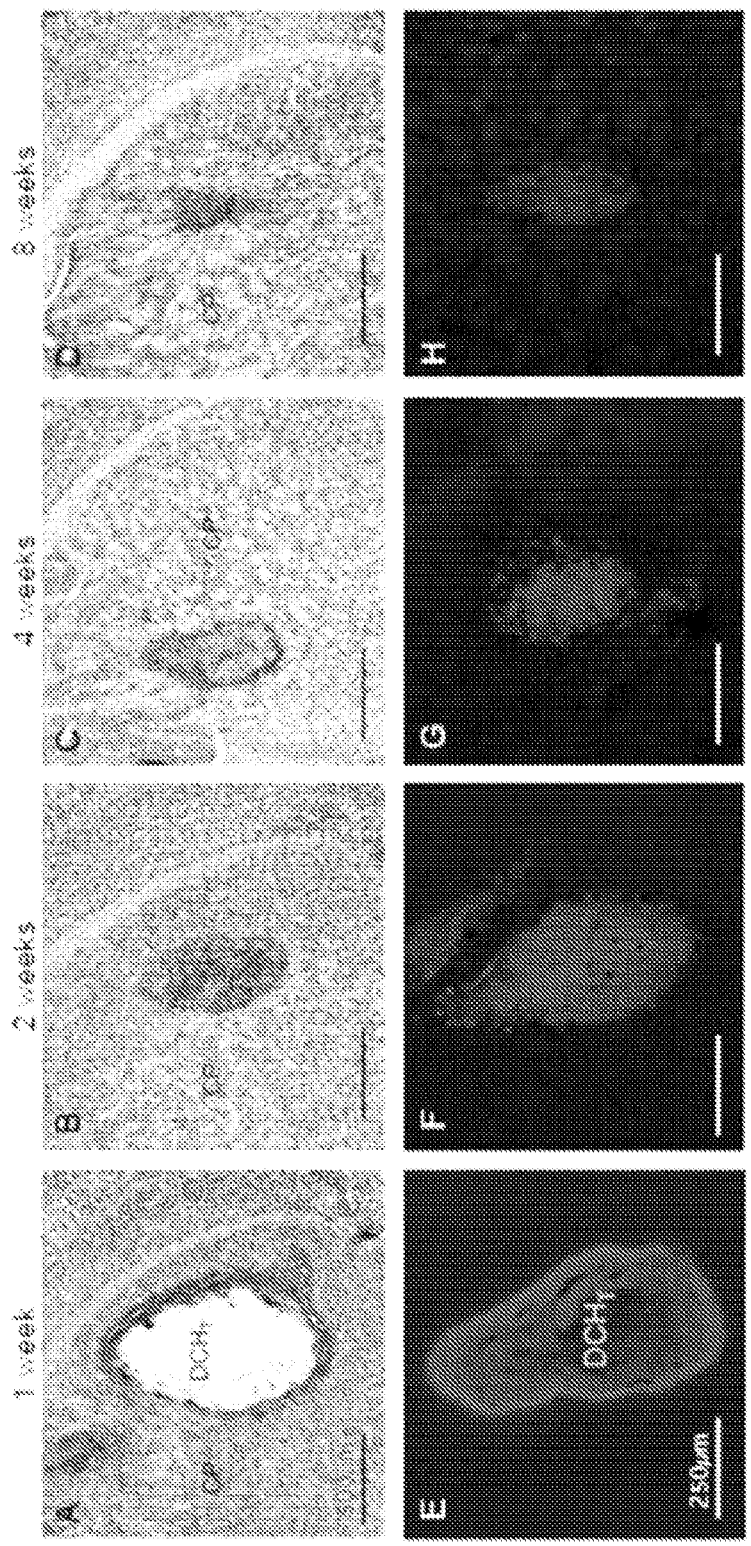
FIG. 9 shows $DCH_T$ injected into mouse forebrain self-assemble into well-formed deposits that are gradually absorbed over time. (A-D) Survey images of Nissl (cresyl violet) stained mouse forebrain show typical deposits of 3% $DCH_T$ 9+1 (1:1) at one to eight weeks after injection into the caudate putamen (CP) nucleus. Note the extensive intermingling of host cells with the $DCH_T$ deposits between one (A) and two (B) weeks after injection. (E-H) Higher magnification images taken at the same time points show $DCH_T$ deposits mixed with a small amount of blue fluorescent dye-labeled $K_{180}L_{30}$. Note the gradual diminution of deposit size (A-D) and loss of blue fluorescence labeling (E-H) over time, which are both indicative of gradual biodegradation and absorption of the $DCH_T$. Scale bars A-D=500 µm, E-H=250 µm.
Figure 10:
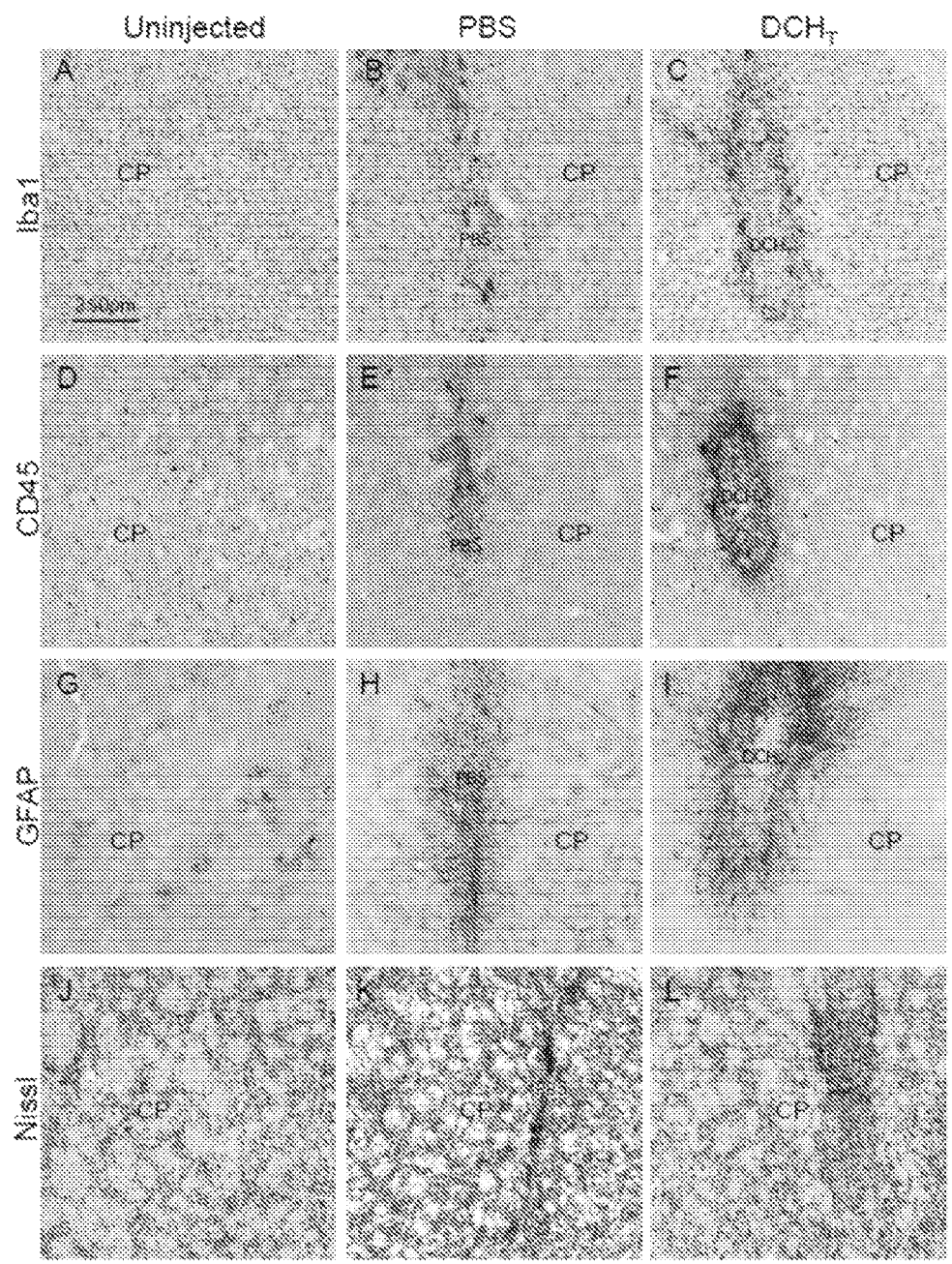
FIG. 10 shows reactive gliosis and inflammation are minimal and similar after injection of $DCH_T$ or PBS into mouse forebrain. (A-L) Images show tissue sections through the caudate putamen (CP) nucleus either uninjected (A,D,G,J), or 8 weeks after local injection of PBS (B,E,H,K) or 3% $DCH_T$ 9+1 (1:1) (C,F,I,L), and immunohistochemically stained for multiple markers of gliosis and inflammation (A-I) or tissue architecture (J-L). Note that compared with uninjected tissue, the reactive responses of different host cell types including microglia stained for Iba1 (A-C), infiltrating inflammatory cells stained for CD45 (D-F) and astrocytes stained for GFAP (G-I) are all mild and similar in tissue immediately adjacent to injections of PBS (B,E,H) or $DCH_T$ (C,F,I). Note also that the architecture of CP tissue immediately adjacent to injection sites of either PBS (K) or $DCH_T$ (L) is indistinguishable in appearance from the characteristic appearance of normal uninjured CP tissue (J) Scale bar=250 µm for all images.

To evaluate $DCH_T$ properties such as gelation and deposit formation in vivo, and to test the effects on surrounding CNS tissue, 2 μl volumes 3% $DCH_T$ 9+1 (1:1) were injected into the mouse forebrain and examined tissue after survival times of one to eight weeks (FIG. 9,10). Injections were made into the center of the caudate putamen nucleus, a large homogenous forebrain structure that is easily targeted and contains neuronal cell bodies intermingled with bundles of myelinated axons and therefor provides a good site to evaluate $DCH_T$ integration with, and effects on, host CNS tissue. In some cases $DCH_T$ was mixed with small amounts of DCH conjugated with fluorescent blue dye to track hydrogel spread and degradation. Examination at one week after injection showed that 3% $DCH_T$ 9+1 (1:1) injected as liquids at room temperature had self-assembled into single, small, well-formed ovoid deposits with a somewhat porous internal structure (FIG. 9A,E). At one week, $DCH_T$ deposits contained few cells (FIG. 9A), but by two weeks had become filled with cells (FIG. 9B) and were well vascularized. Host cells present within the deposits included microglia and astroglia (FIG. 10C,F,I), as well as NG2 cells and endothelia (data not shown). From one to eight weeks after injection, $DCH_T$ deposits gradually diminished both in size (FIG. 9A-D), and fluorescence labeling (FIG. 9E-H). At 4 weeks, deposits were small but clearly still present (FIG. 9C,G), and by eight weeks there was little of the deposits remaining (FIG. 9D,H). At all time points, $DCH_T$ deposits caused little disturbance to host tissue cytoarchitecture (FIG. 9A-D, 10L). At eight weeks, when $DCH_T$ deposits had been mostly degraded and absorbed (FIG. 9D,H), the appearance of adjacent tissue appeared normal and was indistinguishable from tissue adjacent to injections of PBS or from uninjured tissue (FIG. 10J-L). Host tissue gliosis and inflammatory responses to $DCH_T$ deposits were minimal at all times and were indistinguishable from responses to injections of PBS as demonstrated by staining for Iba1, CD45 and GFAP as markers of microglia, inflammatory white blood cells and astrocytes (FIG. 10A-I). Accordingly, $DCH_T$ injected into healthy CNS tissue self-assemble into well-formed deposits that cause minimal reactive gliosis and are gradually absorbed over time with little residual disturbance to the surrounding normal CNS tissue cytoarchitecture.

Non-Ionic $DCH_T$ Support NSC Transplanted into Healthy CNS

Figure 11:
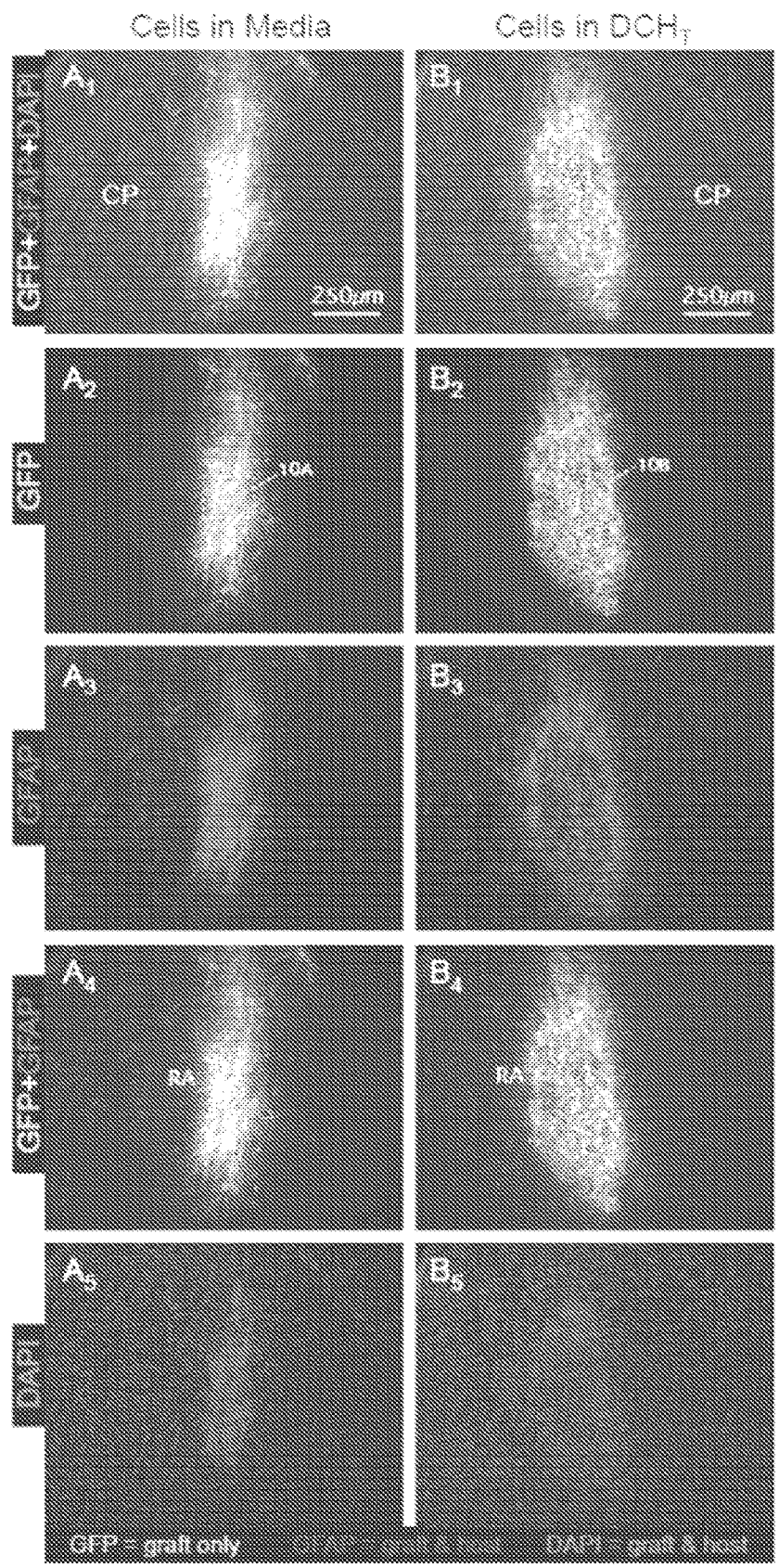
FIG. 11 shows NSC-derived grafts transplanted into uninjured forebrain survive as well or better when injected in $DCH_T$ compared with culture media. ($A_{1-5}$,$B_{1-5}$) Images show grafts derived from NSC transplanted into the caudate putamen (CP) nucleus in either culture media ($A_{1-5}$) or 3% $DCH_T$ 9+1 (1:1) ($B_{1-5}$). The grafts have been stained by triple histofluorescence labeling for the transgenic reporter protein GFP (green), which is expressed only by grafted cells, and the astroglial and progenitor cell marker GFAP (red) and the nuclear marker DAPI, both of which are present in both graft and host cells. Images in $A_{1-5}$ and $B_{1-5}$ show the same fields using different filter combinations. Note that grafts transplanted in $DCH_T$ are larger, more evenly spaced and more closely approximate the density of host cells ($B_{1-5}$) compared with grafts transplanted in media that form a densely packed cluster ($A_{1-5}$). Most grafted cells express both GFP and GFAP under both transplantation conditions ($A_4$,$B_4$). Note also that the reactive astrocyte (RA) response is equivalent adjacent to grafts transplanted in media ($A_4$) or $DCH_T$ ($B_4$). Boxes in $A_2$, $B_2$ indicate areas shown n FIGS. 12A, B. Scale bar=250 µm for all images.
Figure 12:
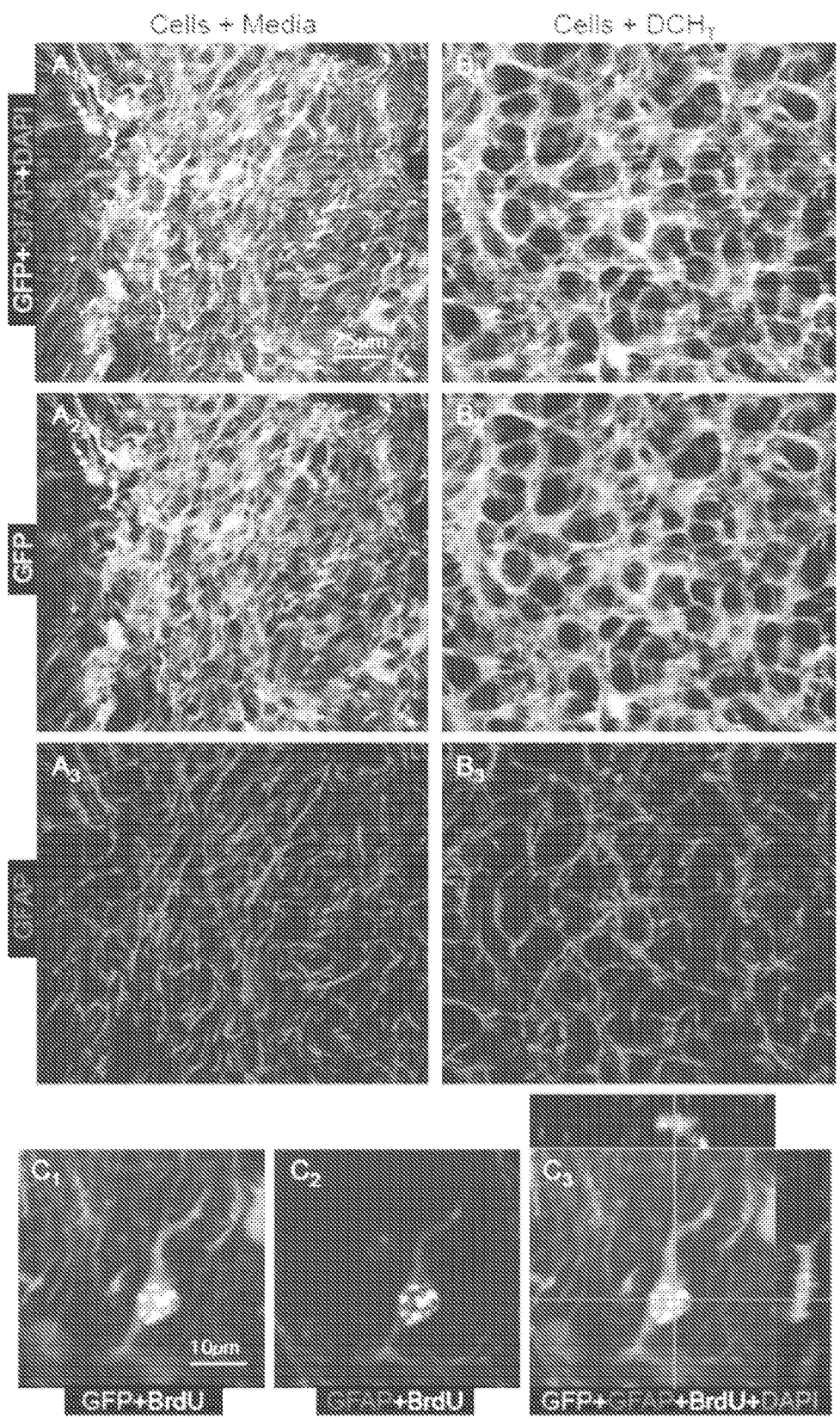
FIG. 12 shows NSC-derived grafts transplanted into uninjured forebrain in $DCH_T$ without added bioactive cargos consist primarily of GFAP-expressing astroglia, some of which retain proliferative potential in vivo. ($A_{1-3}$,$B_{1-3}$) Detail images of the boxed areas in FIGS. 9 $A_2$,$B_2$ show that the cells in grafts transplanted in media form densely packed clusters with lithe or no space between cells ($A_{1-3}$), whereas cells transplanted in 3% DCH-9+1 (1:1) are more evenly distributed with spaces between cells ($B_{1-3}$) in a manner that more closely approximates the distribution of cells in adjacent host CNS tissue. Note that most grafted cells express both GFP and GFAP under both transplantation conditions ($A_{1-3}$,$B_{1-3}$). ($C_{1-3}$) Oil-immersion images of the same cell using different filter combinations show a GFP-labeled, GFAP-expressing, graft-derived cell that exhibits dense nuclear labeling with BrdU, indicating that this cell proliferated sometime between two and six days after transplantation during which time BrdU was administered to the host. Scale bars A,B=50 µm, C=10 µm.

The effects of transplanting NSC into healthy CNS while suspended either in culture medium or in $DCH_T$ (FIG. 11,12) were compared as an initial test of $DCH_T$ as carriers for NSC grafts in vivo. NSC derived from E11 embryos were expanded in vitro as neurospheres and labeled with GFP. For transplantation, NSC were suspended in either culture medium or in 3% $DCH_T$ 9+1 (1:1). Cells suspended in culture medium settled rapidly in the injection cannula and formed concentrated clumps and sedimented rapidly to the bottom of the injection fluid well before the midway point of the injection time (FIG. 8C). In contrast, cells remained evenly suspended in the viscous medium of the $DCH_T$ for the entire injection time (FIG. 8C). As discussed above, injections were made into the center of the caudate putamen nucleus, which provides a good site to evaluate graft integration with, and effects on, host CNS tissue. At three weeks after injection, NSC transplanted in medium had formed small grafts of densely packed cells that often formed clumps with little or no space between cells (FIG. $11A_{1-5}$, $12A_{1-3}$). In contrast, NSC transplanted in $DCH_T$ consistently formed larger deposits in which cells were more evenly distributed and less densely packed with spaces between cell somata in a manner that more closely approximated the cell density of host tissue (FIG. $11B_{1-5}, 12B_{1-3}$). Double label staining indicated that most GFP-positive, NSC-derived cells in grafts transplanted either in medium or $DCH_T$ also expressed GFAP, a marker that labels both astrocytes and neural progenitors (FIG. $11A_{1-5},B_{1-5},12A_{1-5},12B_{1-3}$). NSC-derived Taft transplanted either in medium or $DCH_T$ interacted equally well with host tissue and caused no evidence of degenerative changes and provoked only minimal reactivity of host astrocytes (FIG. $11A_4,B_4$) or microglia (data not shown). No double labeling was found with markers of mature neurons (NeuN) or oligodendrocytes ($GST_\pi$) in grafts transplanted either n medium or $DCH_T$ (data not shown). Because GFAP is a marker found in NSC as well as in mature astrocytes, it is not possible to distinguish among these cells based only on GFAP staining [26, 41]. It was therefore investigated for evidence of proliferative activity in NSC-derived grafts in vivo to test whether some of the GFAP-positive cells in the grafts might have retained NSC potential after transplantation. To do so, BrdU, which is taken up selectively by cells during the S phase of cell division and is commonly used to label proliferating cells in the CNS [28] was used. BrdU was administered to hosts from two to seven days after transplantation. Multiple labeling immunohistochemistry showed that a number of GFP and GFAP-positive cells were also BrdU positive, indicating that at least some NSC-derived cells transplanted in $DCH_T$ continued to proliferate and retained some progenitor properties for at least several days in vivo (FIG. $12C_{1-3}$). These findings show that $DCH_T$ can efficiently serve as vehicle carriers for transplantation of neural stem cells into CNS tissue and that at least some NSC derived cells transplanted in $DCH_T$ continue to proliferate in vivo for days after transplantation.

Figure 8:
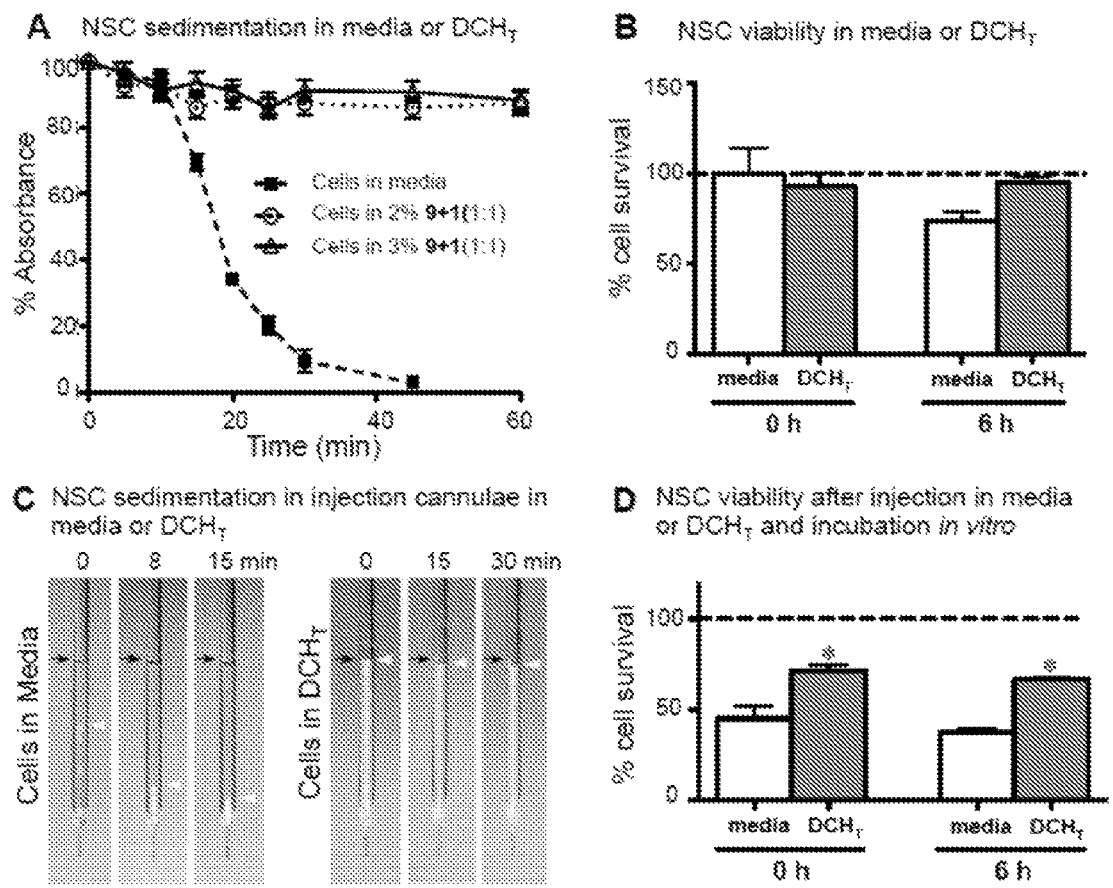
FIG. 8 shows the sedimentation and viability of NSC in $DCH_T$ after injection in vitro. (A) Graph shows NSC (200,000 cells/µl) sedimentation in media or in different concentrations of optimized $DCH_T$ 9+1 (1:1) as determined by scattered light absorbance (λ=500 nm) at room temperature (22° C.). Time zero was measured immediately after achieving suspension of NSC in either vehicle. (B) Graph compares viability of NSC in either media or 2% $DCH_T$ 9+1 (1:1) after incubation on ice for 6 hours to mimic normal handling conditions prior to in vivo injections. Time zero was measured immediately after harvesting of cell cultures and suspension of NSC in either vehicle. (C) Photographic images compare NSC (200,000 cells/µl) sedimentation in 2 µl of either media or 3% $DCH_T$ 9+1 (1:1) after loading injection cannulae (glass micropipettes) to model the in vivo injection procedure. Time zero was measured immediately after the 10 minutes required to load the pipettes with NSC in either vehicle. Note that considerable cell dumping and sedimentation occurred during the loading period with NSC in media. Black arrows indicate top of loaded vehicle. White arrowheads indicate top of suspended NSC. (D) Graph compares viability of NSC (200,000 cells/µl) suspended in either media or 3% $DCH_T$ 9+1 (1:1) after ejection through pulled glass micropipettes (with beveled ground tips of 150-250 µm internal diameter) over a 10 minute period followed by incubation on ice for 0 or 6 hours.
Figure 13:
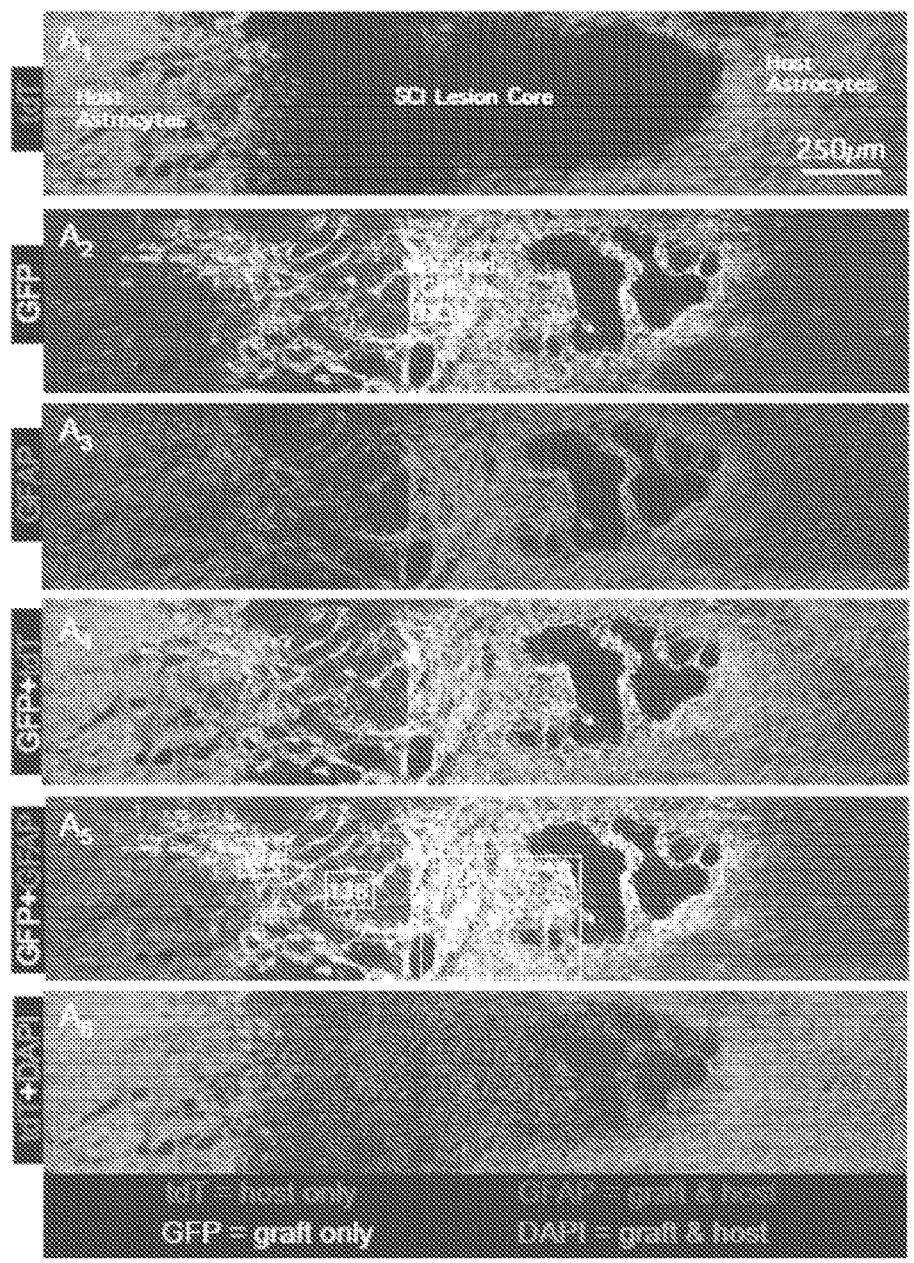
FIG. 13 shows NSC transplanted in $DCH_T$ into a single site in the center of severe spinal cord injury (SCI) can spread throughout large areas of non-neural lesion core tissue and form bridges of graft-derived neural tissue that connect separated areas of host neural tissue. ($A_{1-6}$) Images show a graft derived from NSC transplanted in 3% $DCH_T$ 9+1 (1:1) into the non-neural lesion core of a SCI at the clinically realistic time of 2 days after injury. The graft has been stained by quadruple histofluorescence labeling for multiple markers including the transgenic reporter protein tdT (violet), which is expressed only by host astrocytes, the transgenic reporter protein GFP (green), which is expressed only by grafted cells, the astroglial and progenitor cell marker GFAP (red) and the nuclear marker DAPI, which are present in both graft and host cells. Images $A_{1-6}$ show the same field using different filter combinations. Note the large SCI lesion that is devoid of host astrocytes but is filled with NSC-derived grafted cells. Note that GFAP is expressed by both grafted and host astroglial cells. Note also the overlap of host and graft-derived astroglia at the borders of the lesion. Boxes in As indicate areas shown at higher magnification in FIGS. 12A and 13A,B. Scale bar=250 µm.
Figure 14:
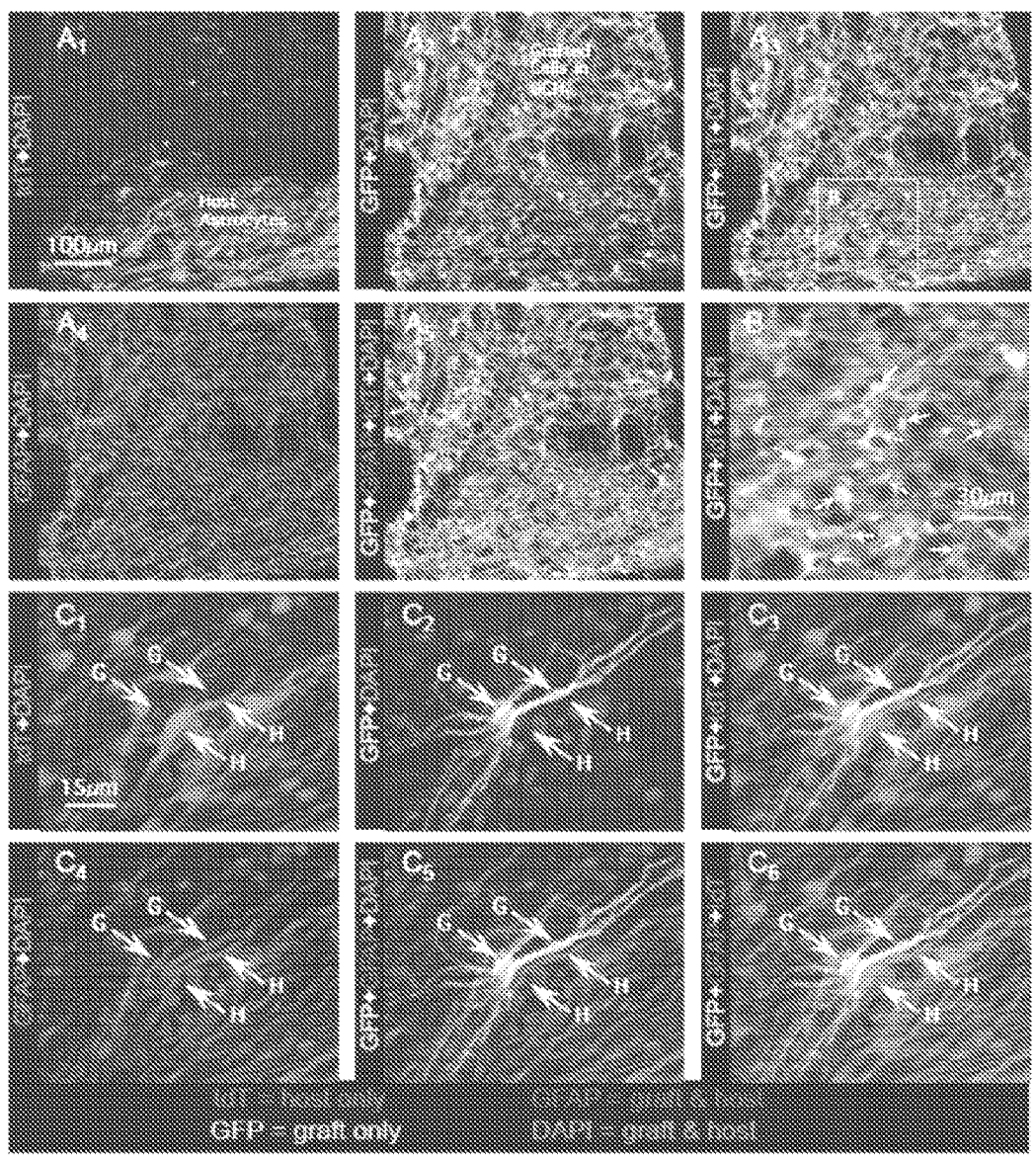
FIG. 14 shows GFAP-positive astroglia derived from NSC transplanted in $DCH_T$ into a single site in the center of severe spinal cord injury (SCI) lesions migrate to intermingle with host astroglia and thereby establish overlapping interfaces of graft and host neural tissue. ($A_{1-5}$) Images of the area in box labeled 14A in FIG. $13A_5$ show the overlap of GFP- and GFAP-positive graft-derived cells with tdT- and GFAP-positive host astroglia in host tissue bordering the graft in the SCI lesion. Images $A_{1-5}$ show the same field using different filter combinations. Box in $A_3$ indicates area shown at higher magnification in B. (B) Detail of boxed area in $A_3$ shows intermingling of GFP and tdT positive cells. ($C_{1-6}$) Oil-immersion images of the same field using different filter combinations show the close juxtaposition of a GFP- and GFAP-positive graft-derived (G) astroglia with a tdT- and GFAP-positive host (H) astroglia in host tissue adjacent to the graft. Scale bars A=100 µm, B=30 µm, C=15 µm.
Figure 15:
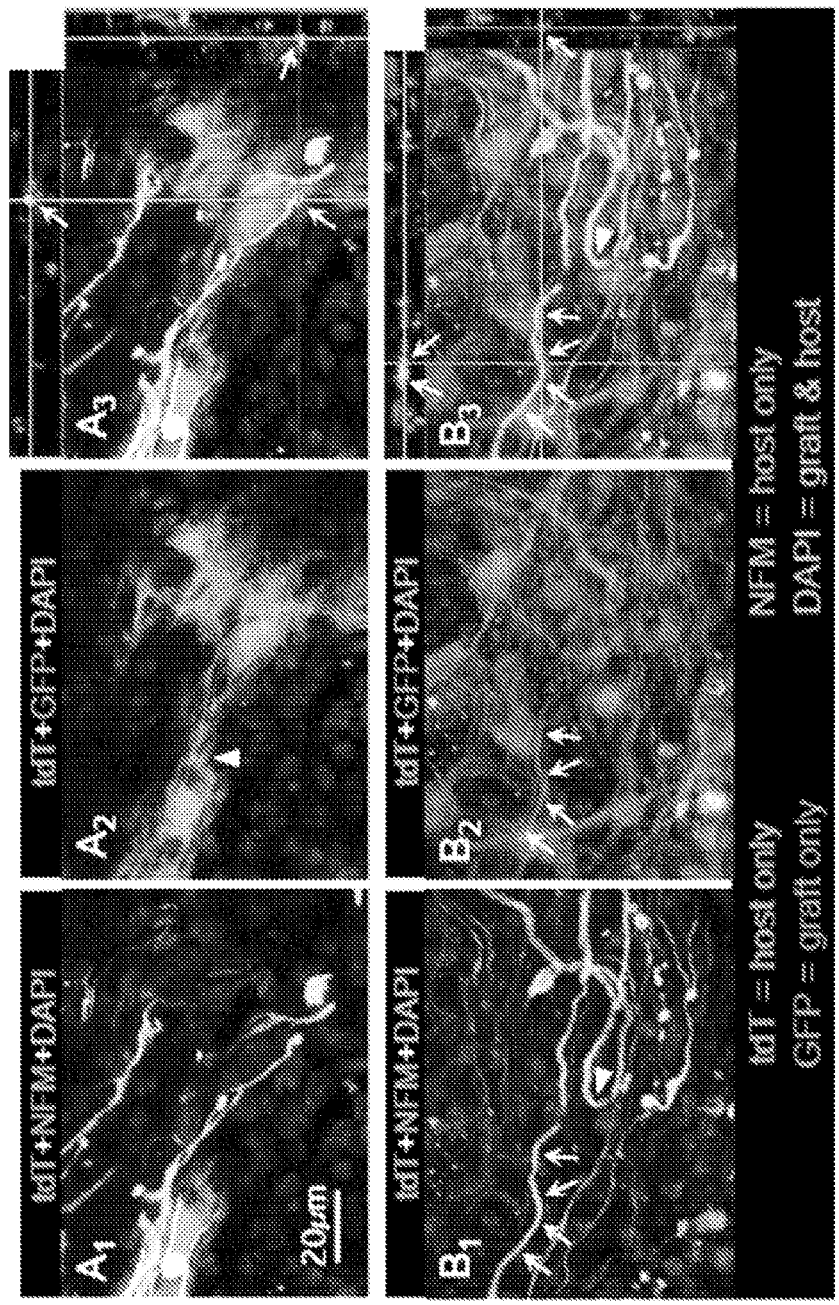
FIG. 15 shows astroglia derived from NSC transplanted in $DCH_T$ into a single site in the center of severe spinal cord injury (SCI) lesions can support the regrowth of host axons that transition from endogenous astroglia to graft-derived astroglia at SCI lesion borders and grow along graft-derived astroglia in SCI lesion core areas devoid of host neural cells. ($A_{1-3}$) Oil-immersion images of the same field using different filter combinations show NFM-positive host axons that are in direct contact with both host tdT-positive astroglia and graft-derived GFP-positive astroglia in a transition zone where there is overlap of host and graft-derived astroglia at the border to the SCI lesion demarcated by the box labeled 15A in FIG. $13A_5$. Arrowhead in $15A_2$ indicates transition point of an axon from a host astroglia to a graft-derived astroglia. Arrows in the three-dimensional ortho-image $15A_3$ indicate the direct contact of a host axon with the surface of a graft-derived astroglia. ($B_{1-3}$) Oil-immersion images of the same field using different filter combinations show NFM-positive host axons that are in direct contact with graft-derived GFP-positive astroglia in the center of an SCI lesion demarcated by the box labeled 15B in FIG. $13A_5$. Arrowhead indicates a host axon that reverses its direction, which is regarded a hallmark of regenerating axons. Arrows indicate the direct contact of a host axon with the surface of a graft-derived astroglia. Scale bar=20 µm for all images.

Non-Ionic $DCH_T$ Support Neural Stem Cells Transplanted into Spinal Cord Injury Lesions The effects of $DCH_T$ on NSC transplanted into non-neural lesion core tissue after SCI (FIG. 13,14, 15) was tested. After traumatic injury in the CNS, lesions form that have different compartments, including central areas of non-neural lesion core tissue, which is surrounded by astrocyte scar that rapidly transitions to a perimeter of hypertrophic reactive astrocytes [1]. The central lesion cores of non-neural tissue represent major barriers across which damaged axons do not regrow, thus disconnecting areas of neural tissue. Non-neural lesion core tissue can be targeted by injections of cell grafts or biomaterials, alone or in combination, in an effort to improve neural repair by facilitating host axon regrowth along matrix or cellular bridges, or potentially by providing new neural cells that may form or facilitate relay connections [1]. Here, the survival and distribution of NSC suspended in 3 $DCH_T$ 9+1 (1:1) and injected at single sites n the centers of large SCI lesions at two days after severe crush SCI was investigated. As discussed above, cells in $DCH_T$ remained suspended evenly in this viscous medium for the entire injection time (FIG. 8). Transplantation of GFP-positive grafts into transgenic hosts that expressed the reporter protein tdTomato in astrocytes allowed clear discrimination of host and graft-derived cells (FIG. $13A_{1,2,4}$, $14A_{1-3},B,C_{1-6}$). This type of double labeling showed GFP-labeled NSC transplanted in $DCH_T$ at single sites into the center of large SCI lesions consistently formed grafts that spread across the entire span of large areas of lesion core that contained no host neural tissue (i.e. no host neurons, oligodendrocytes or astrocytes) (FIG. $13A_{1-6}$). As in the case of forebrain grafts, most graft-derived cells were GFAP positive (FIG. $13A_{2,3,5}, 14A_{2,4,5}$). Double labeling with GFP and tdTomato also showed that graft-derived GFP-positive astroglia migrated for short distances into host tissue (FIG. $13A_{1,2,4}, 14A_{1-3}$) where they intermingled with host astrocytes ($12B, C_{1-6}$). This intermingling of graft with host cells occurred around the entire circumference of the graft (FIG. $13A_4, 14A_3$). Thus, NSC transplanted in $DCH_T$ formed contiguous bridges of graft-derived neural tissue that connect widely separated areas of host neural tissue (FIG. $13A_{1-6}$). To test whether such bridges of grafted neural cells might support the regrowth of transected host axons, immunohistochemical staining for neurofilament M (NFM), which labels axons attempting to grow into SCI lesions [42] was used. In the interface regions between host and graft, host-derived NFM-positive (and GFP-negative) axons were found in close contact with, and that appeared to have regrown along the edges of tdT-positive host astroglia and then transitioned from close contact with the host astroglia to close contact with GFP-positive graft-derived astroglia (FIG. $15A_{1-3}$). Such NFM-positive axons then passed into and through SCI lesion core areas that were devoid of host neural cells, where they were in close contact with, and appeared to have regrown along, GFP-positive NSC graft-derived astroglia (FIG. $15B_{1-3}$). These NFM-positive axons appeared to follow along graft-derived astroglia surfaces and exhibited erratic and tortuous courses that sometime completely reversed direction to double back on themselves (FIG. $15B_{1-3}$), in a manner that has been used as a criterion for regrowing, as opposed to spared, axons after SCI [43]. These findings show that astroglia derived from NSC transplanted in $DCH_T$ into the center of severe SCI lesions can support the regrowth of host axons that transition from endogenous astroglia to graft-derived astroglia at SCI lesion borders and grow along graft-derived astroglia in SCI lesion core areas that are devoid of host neural lineage cells.

REFERENCES

[1] Burda J E, Sofroniew M V. Reactive gliosis and the multicellular response to CNS damage and disease. Neuron. 2014; 81:229-48.
[2] Nagahara A H, Tuszynski M H. Potential therapeutic uses of BDNF in neurological and psychiatric disorders. Nature reviews Drug discovery. 2011; 10:209-19.
[3] Abematsu M, Tsujimura K, Yamano M, Saito M, Kohno K, Kohyama J, et al. Neurons derived from transplanted neural stem cells restore disrupted neuronal circuitry in a mouse model of spinal cord injury. J Clin Invest. 2010; 120:3255-66.
[4] Bonner J F, Connors T M, Silverman W F, Kowalski D P, Lemay M A, Fischer I. Grafted neural progenitors integrate and restore synaptic connectivity across the injured spinal cord. J Neurosci. 2011; 31:4675-86.

[5] Lu P, Wang Y, Graham L, McHale K, Gao M, Wu D, et al. Long-distance growth and connectivity of neural stem cells after severe spinal cord injury. Cell. 2012; 150:1264-73.

[6] Lemmens R, Steinberg G K. Stem cell therapy for acute cerebral injury: what do we know and what will the future bring? Current opinion in neurology. 2013; 26:617-25.

[7] Dunnett S B, Rosser A E. Challenges for taking primary and stem cells into clinical neurotransplantation trials for neurodegenerative disease. Neurobiol Dis. 2014; 61:79-89.

[8] Pakulska M M, Bathos B G, Shoichet M S. Injectable hydrogels for central nervous system therapy. Biomed Mater. 2012; 7:024101.

[9] Yang C Y, Song B, Ao Y, Nowak A P, Abelowitz R B, Korsak R A, et al. Biocompatibility of amphiphilic diblock copolypeptide hydrogels in the central nervous system. Biomaterials. 2009; 30:2881-98.

[10] Deming T J. Polypeptide hydrogels via a unique assembly mechanism. Soft Matter. 2005; 1:28-35.

[11] Deming T J. Facile synthesis of block copolypeptides of defined architecture. Nature. 1997; 390:386-9.

[12] Nowak A P, Breedveld V, Pakstis L, Ozbas B, Pine D J, Pochan D, et al. Rapidly recovering hydrogel scaffolds from self-assembling diblock copolypeptide amphiphiles. Nature. 2002; 417:424-8.

[13] Breedveld V, Nowak A P, Sato J, Deming T J, Pine D J. Rheology of block copolypeptide solutions: hydrogels with tunable properties. Macromolecules. 2004; 37:3943-53.

[14] Song B, Song J, Zhang S, Anderson M A, Ao Y, Yang C Y, et al. Sustained local delivery of bioactive nerve growth factor in the central nervous system via tunable diblock copolypeptide hydrogel depots. Biomaterials. 2012; 33:9105-16.

[15] Zhang S, Anderson M A, Ao Y, Khakh B S, Fan J, Deming T J, et al. Tunable diblock copolypeptide hydrogel depots for local delivery of hydrophobic molecules in healthy and injured central nervous system. Biomaterials. 2014:35:1989-2000.

[16] Peppas N A, Huang Y, Torres-Lugo M, Ward J H, Zhang J. Physicochemical foundations and structural design of hydrogels in medicine and biology. Annu Rev Biomed Eng. 2000; 2:9-29.

[17] Hoare T R, Kohane D S. Hydrogels in drug delivery: Progress and challenges. Polymer. 2008; 49:1993-2007.

[18] Kramer J R, Rodriguez A R, Choe U J, Kamei D T, Deming T J. Glycopolypeptide conformations in bioactive block copolymer assemblies influence their nanoscale morphology. Soft Matter. 2013; 9:3389-95.

[19] Gerdoni E, Gallo B, Casazza S, Musio S, Bonanni I, Pedemonte E, et al. Mesenchymal stem cells effectively modulate pathogenic immune response in experimental autoimmune encephalomyelitis. Ann Neurol. 2007; 61:219-27.

[20] Conti L, Pollard S M, Gorba T, Reitano E, Toselli M, Biella G, et al. Niche-independent symmetrical self-renewal of a mammalian tissue stem cell. PLoS Biol. 2005:3:e283.

[21] Chen C, Wang Z, Li Z. Thermoresponsive polypeptides from pegylated poly-L-glutamates. Biomacromolecules. 2011; 12:2859-63.

[22] Brzezinska K R, Curtin S A, Deming T J. Polypeptide end-capping using functionalized isocyanates: Preparation of pentablock copolymers. Macromolecules. 2002; 35:2970-6.

[23] van der Veen M, Norde W, Stuart M C. Effects of succinylation on the structure and thermostability of lysozyme. Journal of agricultural and food chemistry. 2005; 53:5702-7.

[24] Masuda T, Ide N, Kitabatake N. Effects of chemical modification of lysine residues on the sweetness of lysozyme. Chemical senses. 2005; 30:253-64.

[25] Madisen L, Zwingman T A, Sunkin S M, Oh S W, Zariwala H A, Gu H, et al. A robust and high-throughput Cre reporting and characterization system for the whole mouse brain. Nat Neurosci. 2010; 13:133-40.

[26] Garcia A D R, Doan N B, Imura T, Bush T G, Sofroniew M V. GFAP-expressing progenitors are the principle source of constitutive neurogenesis in adult mouse forebrain, Nature Neurosci. 2004; 7:1233-41.

[27] Herrmann J E, Imura T, Song B, Qi J, Ao Y, Nguyen T K, et al. STAT3 is a critical regulator of astrogliosis and scar formation after spinal cord injury. J Neurosci. 2008; 28:7231-43.

[28] Wanner I B, Anderson M A, Song B, Levine J, Fernandez A, Gray-Thompson Z, et al. Glial scar borders are formed by newly proliferated, elongated astrocytes that interact to corral inflammatory and fibrotic cells via STAT3-dependent mechanisms after spinal cord injury. J Neurosci. 2013; 33:12870-86.

[29] Faulkner J R, Herrmann J E, Woo M J, Tansey K E, Doan N B, Sofroniew M V. Reactive astrocytes protect tissue and preserve function after spinal cord injury. J Neurosci. 2004; 24:2143-55.

[30] Pakstis L M, Ozbas B, Hales K D, Nowak A P, Deming T J, Pochan D. Effect of chemistry and morphology on the biofunctionality of self-assembling diblock copolypeptide hydrogels. Biomacromolecules. 2004; 5:312-8.

[31] Choe U J, Rodriguez A R, Li Z, Boyarskiy S, Deming T J, Kamei D T. Characterization and minimization of block copolypeptide vesicle toxicity using different hydrophobic chain lengths. Macromolecular Chem Phys. 2013; 214:994-9.

[32] Sela M, Katchalski E. Biological properties of poly-alpha-amino acids. Advances in protein chemistry. 1959; 14:391-478.

[33] Rodriguez A R, Choe U J, Kamei D T, Deming T J. Fine tuning of vesicle assembly and properties using dual hydrophilic triblock copolypeptides. Macromolecular bioscience. 2012; 12:805-11.

[34] Rodriguez A R, Kramer J R, Deming T J. Enzyme-triggered cargo release from methionine sulfoxide containing copolypeptide vesicles. Biomacromolecules. 2013; 14:3610-4.

[35] Bellomo E G, Wyrsta M D, Pakstis L, Pochan D J, Deming T J. Stimuli-responsive polypeptide vesicles by conformation-specific assembly. Nat Mater. 2004; 3:244-8.

[36] Ruel-Gariepy E, Leroux J C. In situ-forming hydrogels—review of temperature-sensitive systems. European journal of pharmaceutics and biopharmaceutics: official journal of Arbeitsgemeinschaft fur Pharmazeutische Verfahrenstechnik eV. 2004; 58:409-26.

[37] Qui Y, Park K. Environment-sensitive hydrogels for drug delivery. Adv Drug Deliv Rev. 2012, 64:49-60.

[38] Schmaljohann D. Thermo- and pH-responsive polymers in drug delivery. Adv Drug Deliv Rev. 2006; 58:1655-70.

[39] Aguado B A, Mulyasasmita W, Su J, Lampe K J, Heilshorn S C. Improving viability of stem cells during syringe needle flow through the design of hydrogel cell carriers. Tissue Eng Part A. 2012; 18:806-15.

[40] Yan C, Mackay M E, Czymmek K, Nagarkar R P, Schneider J P, Pochan D J. Injectable solid peptide hydrogel as a cell carrier: effects of shear flow on hydrogels and cell payload. Langmuir: the ACS journal of surfaces and colloids. 2012; 28:6076-87.

[41] Kriegstein A, Alvarez-Buylla A. The glial nature of embryonic and adult neural stem cells. Annu Rev Neurosci. 2009; 32:149-84.

[42] Inman D M, Steward O. Ascending sensory, but not other long-tract axons, regenerate into the connective tissue matrix that forms at the site of a spinal cord injury in mice. J Comp Neurol. 2003; 462:431-49.

[43] Tuszynski M H, Steward O. Concepts and methods for the study of axonal regeneration in the CNS. Neuron. 2012; 74:777-91.

[44] Yu M, Nowak A P, Pochan D J, Deming T J. Methylated mono- and diethyleneglycol functionalized polylysines: Nonionic, helical, water soluble polypeptides. 1999; 121:12210-1.

[45] Kramer J R, Deming T J. Glycopolypeptides via living polymerization of glycosylated-L-lysine N-carboxyanhydrides. J Am Chem Soc. 2010; 132:15068-71.

[46] Kramer J R, Deming T J Glycopolypeptides with a redox-triggered helix-to-coil transition. J Am Chem Soc. 2012; 134:4112-5.

[47] Shen J, Chen C, Fu W, Shi L, Li Z. Conformation-specific self-assembly of thermo-responsive poly(ethylene glycol)-b-polypeptide diblock copolymer. Langmuir: the ACS journal of surfaces and colloids. 2013; 29:6271-8.

[48] Huang J, Hastings C L, Duffy G P, Kelly H M, Raeburn J, Adams D J, et al. Supramolecular hydrogels with reverse thermal gelation properties from (oligo)tyrosine containing block copolymers. Biomacromolecules. 2013; 14:200-6.

[49] Sanchez-Ferrer A, Kotharangannagari V K, Ruokolainen J, Mezzenga R. Thermo-responsive peptide-based triblock copolymer hydrogels. Soft Matter. 2013; 9:4304-11.

[50] Cheng Y, He C, Xiao C, Ding J, Cui H, Zhuang X, et al. Versatile biofunctionalization of polypeptide-based thermosensitive hydrogels via click chemistry. Biomacromolecules. 2013; 14:468-75.

[51] Cheng Y, He C, Ding J, Xiao C, Zhuang X, Chen X. Thermosensitive hydrogels based on polypeptides for localized and sustained delivery of anticancer drugs. Biomaterials. 2013; 34:10338-47.

[52] Lu H D, Charati M B, Kim I L, Burdick J A. Injectable shear-thinning hydrogels engineered with a self-assembling Dock-and-Lock mechanism. Biomaterials. 2012; 33:2145-53.

[53] Iannotti C, Li H, Yan P, Lu X, Wirthlin L, Xu X M. Glial cell line-derived neurotrophic factor-enriched bridging transplants promote propriospinal axonal regeneration and enhance myelination after spinal cord injury. Exp Neurol. 2003; 183:379-93.

[54] McCall J, Weidner N, Blesch A. Neurotrophic factors in combinatorial approaches for spinal cord regeneration. Cell and tissue research. 2012; 349:27-37.

[55] Liu K, Tedeschi A, Park K K, He Z. Neuronal intrinsic mechanisms of axon regeneration. Annu Rev Neurosci. 2011; 34:131-52.

[56] Zukor K, Belin S, Wang C, Keelan N, Wang X, He Z. Short hairpin RNA against PTEN enhances regenerative growth of corticospinal tract axons after spinal cord injury J Neurosci. 2013, 33:15350-61.

[57] Fernandez-Klett F, Priller J. The fibrotic scar in neurological disorders. Brain Pathol. 2014; 24:404-13.

[58] Norenberg M D, Smith J, Marcillo A. The pathology of human spinal cord injury: defining the problems. J Neurotrauma. 2004; 21:429-40.

[59] Silver J, Miller J H. Regeneration beyond the glial scar. Nature Rev Neurosci. 2004; 5:146-56.

[60] Bareyre F M, Kerschensteiner M, Raineteau O, Mettenleiter T C, Weinmann O, Schwab M E. The injured spinal cord spontaneously forms a new intraspinal circuit in adult rats. Nat Neurosci. 2004; 7:269-77.

[61] Courtine G, Song B, Roy R R, Zhong H, Herrmann J E, Ao Y, et al. Recovery of supraspinal control of stepping via indirect propriospinal relay connections after spinal cord injury. Nature Med. 2008; 14:69-74.

[62] Williams R R, Henao M, Pearse D D, Bunge M B. Permissive Schwann cell graft/spinal cord interfaces for axon regeneration. Cell Transplant. 2013.

[63] Chu T, Zhou H, Li F, Wang T, Lu L, Feng S. Astrocyte transplantation for spinal cord injury: Current status and perspective. Brain research bulletin. 2014; 107C:18-30.

The following claims are thus to be understood to include what is specifically illustrated and described above, what is conceptually equivalent, what can be obviously substituted and also what essentially incorporates the essential idea of the invention. Those skilled in the art will appreciate that various adaptations and modifications of the just-described preferred embodiment can be configured without departing from the scope of the invention. The illustrated embodiment has been set forth only for the purposes of example and that should not be taken as limiting the invention. Therefore, it is to be understood that, within the scope of the appended claims, the invention may be practiced other than as specifically described herein.

The invention claimed is:

1. A composition comprising:

an aqueous medium; and a copolypeptide hydrogel forming composition, wherein said copolypeptide composition comprises at least one hydrophilic polypeptide segment or hydrophilic copolypeptide segment and at least one hydrophobic polypeptide segment or hydrophobic copolypeptide segment, wherein the hydrophilic polypeptide segment or hydrophilic copolypeptide segment consists of residues selected from lysine, glutamate, aspartate, arginine, ornithine, homoarginine, a residue of Formula I, a residue of Formula II, a residue of Formula III, a residue of Formula IV, a residue of Formula V, a residue of Formula VI, and combinations thereof; and wherein the hydrophilic polypeptide segment or hydrophilic copolypeptide segment contains less than 50 mol % ionic amino acid residues, wherein an ionic amino acid residue is an amino acid residue having a charged side-chain at pH=7 in water;

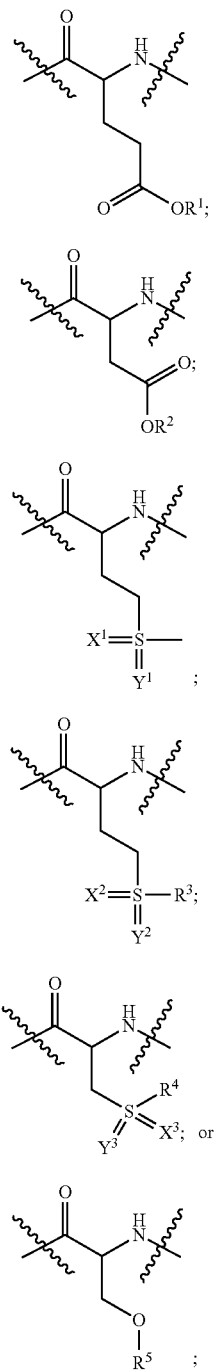

wherein:

R¹ is, independently at each occurrence, —(CH₂CH₂O)ₙCH₃ or

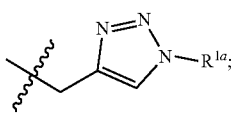

$R^{1a}$ is —(CH₂CH₂O)ₙCH₃;
$R^2$ is, independently at each occurrence, —(CH₂CH₂O)ₙCH₃ or

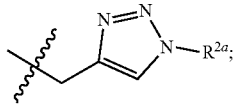

$R^{2a}$ is —(CH₂CH₂O)ₙCH₃;
$X^1$ is O;
$Y^1$ is, independently at each occurrence, absent or O;
$R^3$ is, independently at each occurrence, selected from —(CH₂CH₂O)ₘCH₃, —CH₂CH₂CH₂(sugar), and -sugar;
$X^2$ is, independently at each occurrence, absent or O;
$Y^2$ is, independently at each occurrence, absent or O;
$R^4$ is, independently at each occurrence, selected from —(CH₂CH₂O)ₙCH₃, —CH₂CH₂CH₂(sugar), —CH₂CHR$^{4a}$C(O)OR$^{4b}$, and —CH₂CH₂SO₂CH₂CH₂SR$^{4c}$;
$R^{4a}$ is, independently at each occurrence, —H or —CH₃;
$R^{4b}$ is —(CH₂CH₂O)CH₃;
$R^{4c}$ is —(CH₂CH₂O)ₙCH₃;
$X^3$ is, independently at each occurrence, absent or O;
$Y^3$ is, independently at each occurrence, absent or O;
$R^5$ is, independently at each occurrence, —(CH₂CH₂O)ₙCH₃ or -sugar;
n is an integer from 1-4;
m is an integer from 1-6; and
p is an integer from 1-9.

2. The composition of claim 1, further comprising an agent or a cell.

3. The composition of claim 1, further comprising:
a second copolypeptide hydrogel forming composition,
wherein said second copolypeptide composition comprises at least one hydrophilic polypeptide segment or hydrophilic copolypeptide segment and at least one thermoresponsive polypeptide segment or thermoresponsive copolypeptide segment,
wherein said second copolypeptide composition undergoes a temperature induced transition between a liquid and a transparent hydrogel in said aqueous medium.

4. The composition of claim 3, wherein the at least one thermoresponsive copolypeptide segment comprises at least one thermoresponsive residue and at least one non-ionic residue.

5. The composition of claim 3, further comprising an agent or a cell.

6. A method of delivering an agent or a cell into an organism comprising:
a) creating a mixture comprising:
the agent or the cell,
an aqueous medium, and
a copolypeptide hydrogel forming composition, wherein said copolypeptide composition comprises at least one hydrophilic polypeptide segment or hydrophilic copolypeptide segment and at least one hydrophobic polypeptide segment or hydrophobic copolypeptide segment; wherein the hydrophilic polypeptide segment or hydrophilic copolypeptide segment consists of residues selected from lysine, glutamate, aspartate, arginine, ornithine, homoarginine, a residue of Formula I, a residue of Formula II, a residue of Formula III, a residue of Formula IV, a residue of Formula V, a residue of Formula VI, and combinations thereof; and wherein the hydrophilic polypeptide segment or hydrophilic copolypeptide segment contains less than 50 mol % ionic amino acid residues, wherein an ionic amino acid residue is an amino acid residue having a charged side-chain at pH=7 in water; and b) introducing the mixture into the organism;

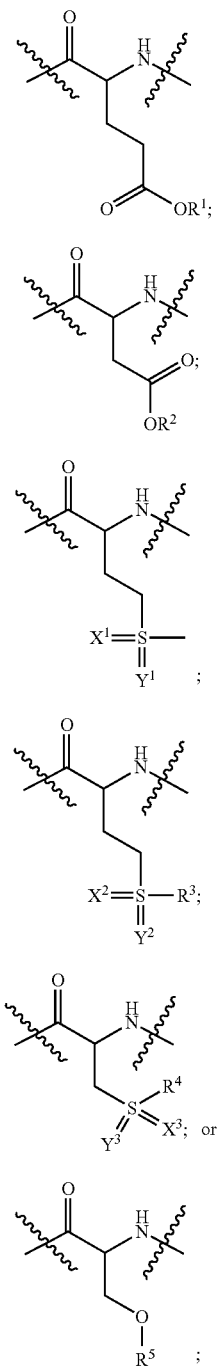

(I)

(II)

(III)

(IV)

(V)

(VI)

wherein:

$R^1$ is, independently at each occurrence, —(CH$_2$CH$_2$O)$_n$CH$_3$ or

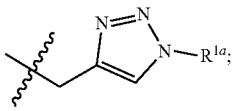

$R^{1a}$ is —(CH$_2$CH$_2$O)$_n$CH$_3$;
$R^2$ is, independently at each occurrence, —(CH$_2$CH$_2$O)$_n$CH$_3$ or

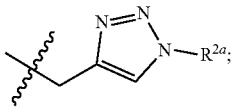

$R^{2a}$ is —(CH$_2$CH$_2$O)$_n$CH$_3$;
$X^1$ is O;
$Y^1$ is, independently at each occurrence, absent or O;
$R^3$ is, independently at each occurrence, selected from —(CH$_2$CH$_2$O)$_m$CH$_3$, —CH$_2$CH$_2$CH$_2$(sugar), and -sugar;
$X^2$ is, independently at each occurrence, absent or O;
$Y^2$ is, independently at each occurrence, absent or O;
$R^4$ is, independently at each occurrence, selected from —(CH$_2$CH$_2$O)$_p$CH$_3$, —CH$_2$CH$_2$CH$_2$(sugar), —CH$_2$CHR$^{4a}$C(O)OR$^{4b}$, and —CH$_2$CH$_2$SO$_2$CH$_2$CH$_2$SR$^{4c}$;
$R^{4a}$ is, independently at each occurrence, —H or —CH$_3$;
$R^{4b}$ is —(CH$_2$CH$_2$O)$_p$CH$_3$;
$R^{4c}$ is —(CH$_2$CH$_2$O)$_p$CH$_3$:
$X^3$ is, independently at each occurrence, absent or O;
$Y^3$ is, independently at each occurrence, absent or O;
$R^5$ is, independently at each occurrence, —(CH$_2$CH$_2$O)$_n$CH$_3$ or -sugar;
n is an integer from 1-4;
m is an integer from 1-6; and
p is an integer from 1-9.

7. The method of delivering an agent or a cell into an organism according to claim 6, wherein the mixture further comprises:
a second copolypeptide hydrogel forming composition,
wherein said second copolypeptide composition comprises at least one hydrophilic polypeptide segment or hydrophilic copolypeptide segment and at least one thermoresponsive polypeptide segment or thermoresponsive copolypeptide segment, and
wherein said second copolypeptide composition undergoes a temperature induced transition between a liquid and a transparent hydrogel in said aqueous medium.

8. The composition of claim 1, wherein a plurality of residues in the hydrophilic polypeptide segment or hydrophilic copolypeptide segment are selected from a residue of Formula I, a residue of Formula II, a residue of Formula III, a residue of Formula IV, a residue of Formula V, and a residue of Formula VI.

9. The composition of claim 1, wherein the hydrophilic polypeptide segment or hydrophilic copolypeptide segment consists of residues selected from a residue of Formula I, a residue of Formula II, a residue of Formula III, a residue of Formula IV, a residue of Formula V, and a residue of Formula VI.

10. The composition of claim 1, wherein the hydrophobic polypeptide segment or hydrophobic copolypeptide segment comprises residues selected from leucine, alanine, phenylalanine, methionine, tyrosine, tryptophan, valine, isoleucine, serine, cysteine, glutamine, asparagine, a γ-alkyl glutamate ester, a β-alkyl aspartate ester, and a ε-modified lysine.
11. The composition of claim 1, wherein the copolypeptide composition is selected from:
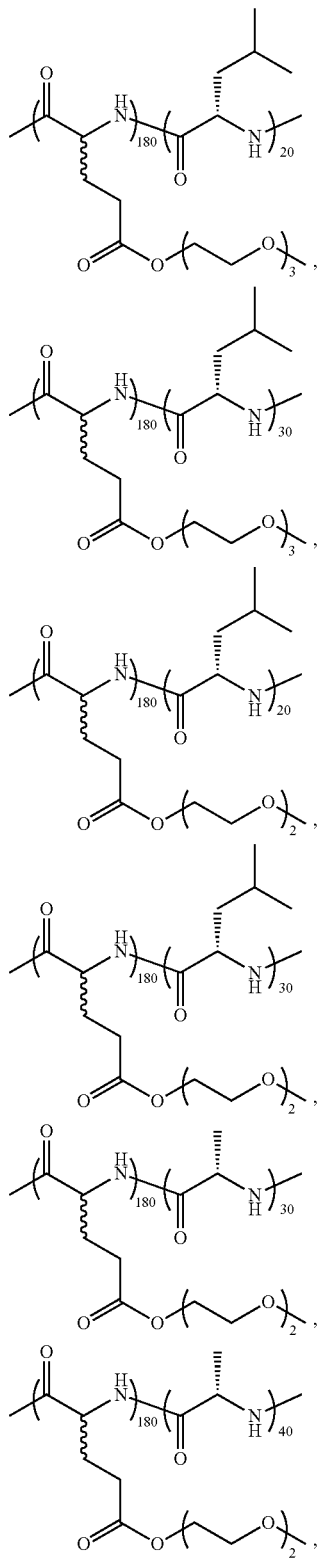
-continued
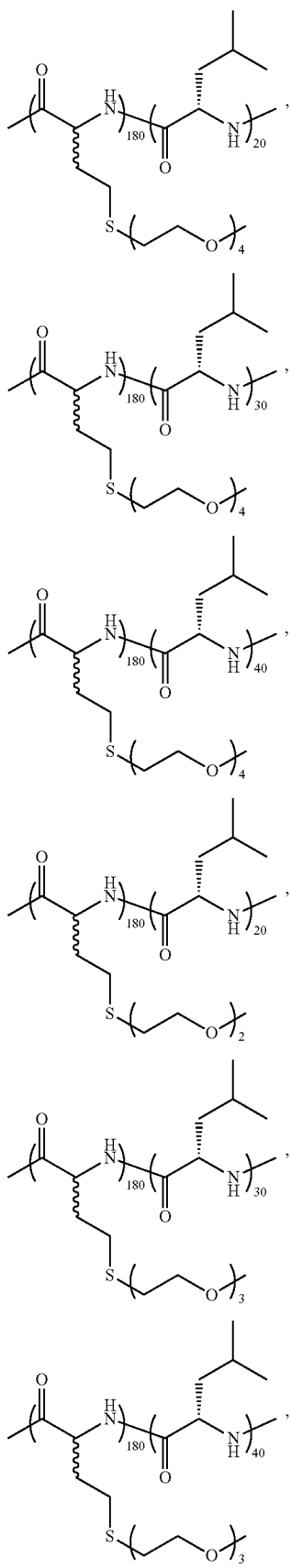

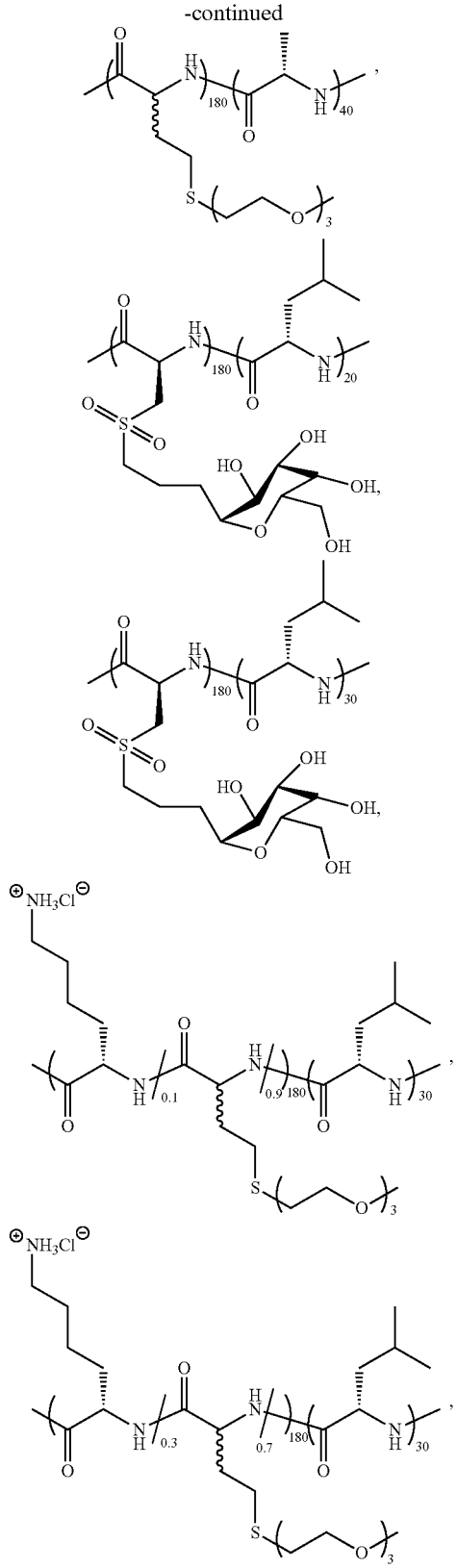
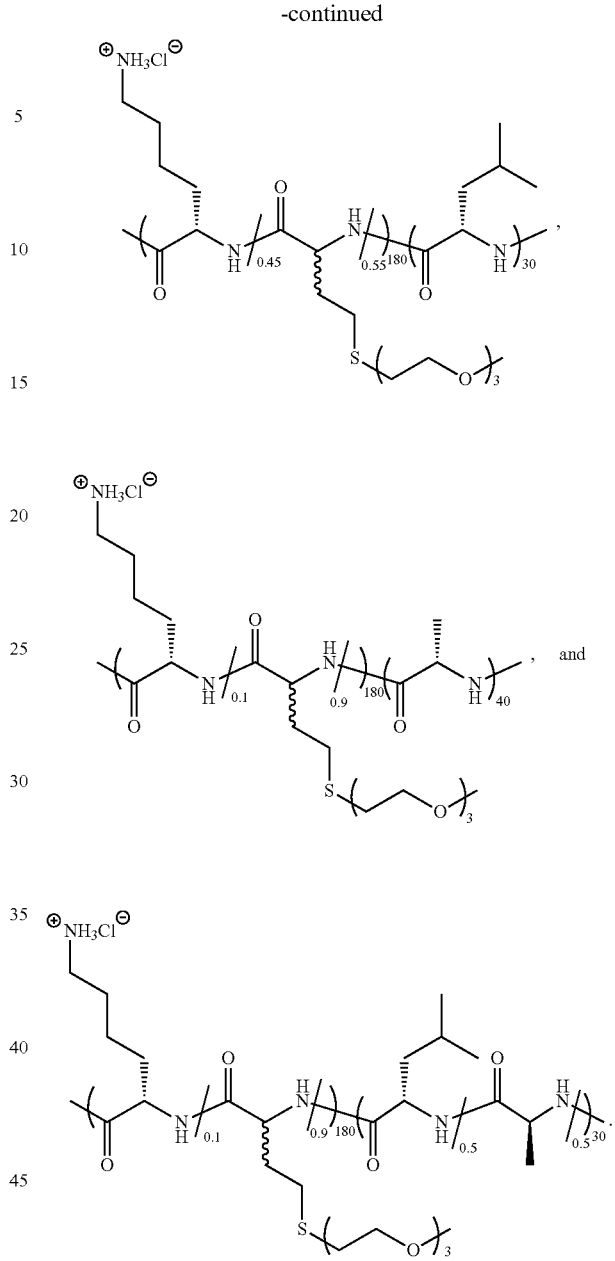

12. The composition of claim 1, wherein the copolypeptide contains less than 50 mol % ionic amino acid residues.

13. The composition of claim 1, wherein, after exposure of a suspension of HeLa cells to the composition at a concentration of 2% for 24 hours, greater than 71% of the HeLa cells are viable.

14. The composition of claim 1, wherein sugar is selected from galactose, glucose, and mannose.

15. The method of claim 6, wherein sugar is selected from galactose, glucose, and mannose.

* * * * *